(12) United States Patent
Haupts

(10) Patent No.: US 10,808,042 B2
(45) Date of Patent: Oct. 20, 2020

(54) IMMUNOGLOBULIN-BINDING PROTEINS AND THEIR USE IN AFFINITY PURIFICATION

(71) Applicant: Navigo Proteins GmbH, Halle/Saale (DE)

(72) Inventor: Ulrich Haupts, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 281 days.

(21) Appl. No.: 15/744,147

(22) PCT Filed: Jul. 14, 2016

(86) PCT No.: PCT/EP2016/066774
§ 371 (c)(1),
(2) Date: Jan. 12, 2018

(87) PCT Pub. No.: WO2017/009421
PCT Pub. Date: Jan. 19, 2017

(65) Prior Publication Data
US 2018/0305463 A1    Oct. 25, 2018

(30) Foreign Application Priority Data
Jul. 16, 2015    (EP) ..................................... 15177056

(51) Int. Cl.
| C07K 16/46 | (2006.01) |
| C07K 16/12 | (2006.01) |
| C07K 1/22  | (2006.01) |
| C07K 14/31 | (2006.01) |

(52) U.S. Cl.
CPC ................ C07K 16/46 (2013.01); C07K 1/22 (2013.01); C07K 14/31 (2013.01); C07K 16/1271 (2013.01); C07K 2317/92 (2013.01)

(58) Field of Classification Search
None
See application file for complete search history.

(56) References Cited

U.S. PATENT DOCUMENTS

| 4,873,192 A  | 10/1989  | Kunkel |
| 5,789,166 A  | 8/1998   | Bauer et al. |
| 5,958,684 A  | 9/1999   | Van Leeuwen et al. |
| 6,217,863 B1 | 4/2001   | Godavarti et al. |
| 6,569,677 B1 | 5/2003   | Legrand et al. |
| 6,620,587 B1 | 9/2003   | Taussig et al. |
| 6,673,901 B2 | 1/2004   | Koide |
| 6,799,121 B2 | 9/2004   | Chu et al. |
| 7,250,297 B1 | 7/2007   | Beste et al. |
| 7,273,924 B1 | 9/2007   | Neri et al. |
| 7,393,918 B2 | 7/2008   | Golemi-Kota et al. |
| 7,601,803 B1 | 10/2009  | Fiedler et al. |
| 7,838,629 B2 | 11/2010  | Fiedler et al. |
| 7,851,599 B2 | 12/2010  | Menrad et al. |
| 8,097,254 B2 | 1/2012   | Neri et al. |
| 8,404,814 B2 | 3/2013   | Neri et al. |
| 8,426,357 B2 | 4/2013   | Kraehmer et al. |
| 8,455,625 B2 | 6/2013   | Neri et al. |
| 8,592,144 B2 | 11/2013  | Fiedler et al. |
| 8,592,179 B2 | 11/2013  | Schraeml et al. |
| 8,623,373 B2 | 1/2014   | Zardi et al. |
| 8,748,351 B2 | 6/2014   | Kunert et al. |
| 8,790,895 B2 | 7/2014   | Fiedler et al. |
| 8,791,238 B2 | 7/2014   | Fiedler et al. |
| 8,921,304 B2 | 12/2014  | Steuernagel et al. |
| 9,492,572 B2 | 11/2016  | Nerkamp et al. |
| 2003/0045681 A1 | 3/2003 | Neri et al. |
| 2003/0073623 A1 | 4/2003 | Drmanac et al. |
| 2004/0043386 A1 | 3/2004 | Pray et al. |
| 2006/0058510 A1 | 3/2006 | Skerra et al. |
| 2006/0099686 A1 | 5/2006 | Fiedler et al. |
| 2007/0015248 A1 | 1/2007 | Anton et al. |
| 2007/0111287 A1 | 5/2007 | Fiedler et al. |
| 2007/0189963 A1 | 8/2007 | Neri et al. |
| 2007/0248536 A1 | 10/2007 | Fiedler et al. |

(Continued)

FOREIGN PATENT DOCUMENTS

| AU | 2013318928 | 4/2015 |
| EP | 1 591 527 A1 | 11/2005 |

(Continued)

OTHER PUBLICATIONS

Office Action (Restriction Requirement) corresponding to U.S. Appl. No. 15/549,022 dated May 3, 2018.
Office Action (Restriction Requirement) corresponding to U.S. Appl. No. 15/549,022 dated Nov. 8, 2018.
Office Action corresponding to U.S. Appl. No. 15/744,054 dated Mar. 14, 2019.
Office Action Restriction Requirement corresponding to U.S. Appl. No. 15/548,976 dated Jun. 14, 2019.
Office Action corresponding to U.S. Appl. No. 15/744,054 dated Jul. 30, 2019.
Abedi et al. (1998) Green fluorescent protein as a scaffold for intracellular presentation of peptides. Nucleic Acids Research 26(2):623-630.
Advisory Action corresponding to U.S. Appl. No. 10/030,605 dated Oct. 13, 2006.

(Continued)

Primary Examiner — Daniel E Kolker
Assistant Examiner — James L Rogers
(74) Attorney, Agent, or Firm — Jenkins, Wilson, Taylor & Hunt, P.A.

(57) ABSTRACT

The present disclosure relates to non-natural binding proteins comprising one or more non-natural immunoglobulin (Ig) binding domains wherein at least one non-natural Ig-binding domain comprises the amino acid sequence X1 X2X3XiXsX5X7 XsQQX11AFYX1sX15LX1 sX19PX21 LX23X24X2sQRX28X2gf IQSLKDDPSXio SXi2Xi3Xi4LXi5EAXigKLXs2Xs3Xs4QXs5PX. The disclosure also relates to compositions such as affinity matrices comprising the non-natural Ig-binding proteins of the invention. Use of these Ig-binding proteins or of the compositions for affinity purification of immunoglobulins and to methods of affinity purification.

11 Claims, 10 Drawing Sheets
Specification includes a Sequence Listing.

(56) References Cited

U.S. PATENT DOCUMENTS

| | | |
|---|---|---|
| 2007/0286843 A1 | 12/2007 | Pfizenmaier et al. |
| 2008/0171851 A1 | 7/2008 | Fiedler et al. |
| 2010/0119446 A1 | 5/2010 | Grabulovski et al. |
| 2010/0130720 A1 | 5/2010 | Schraeml et al. |
| 2011/0162095 A1 | 6/2011 | Hill et al. |
| 2012/0244596 A1 | 9/2012 | Skerra et al. |
| 2012/0301393 A1 | 11/2012 | Steuernagel et al. |
| 2013/0011334 A1 | 1/2013 | Steuernagel et al. |
| 2013/0097737 A1 | 4/2013 | Kovalic et al. |
| 2013/0157878 A1 | 6/2013 | Kunert et al. |
| 2014/0135476 A1* | 5/2014 | Hall .................... B01J 20/3274 435/252.33 |
| 2014/0219959 A1 | 8/2014 | Nerkamp et al. |
| 2015/0183846 A1 | 7/2015 | Lange et al. |
| 2018/0030098 A1 | 2/2018 | Bosse-Doenecke et al. |
| 2018/0030140 A1 | 2/2018 | Bosse-Doenecke et al. |
| 2018/0194819 A1 | 7/2018 | Fiedler et al. |
| 2018/0273636 A1 | 9/2018 | Settele et al. |
| 2019/0117791 A1 | 4/2019 | Haupts et al. |
| 2019/0177376 A1 | 6/2019 | Knick et al. |

FOREIGN PATENT DOCUMENTS

| | | |
|---|---|---|
| EP | 2 532 672 A2 | 12/2012 |
| EP | 2 727 942 A1 | 5/2014 |
| EP | 2 738 180 | 6/2014 |
| EP | 2829552 A1 | 1/2015 |
| RU | 2134696 C1 | 8/1999 |
| WO | WO 2005/044845 A2 | 5/2005 |
| WO | WO 2007/054120 A1 | 5/2007 |
| WO | WO 2012/171541 A1 | 12/2012 |
| WO | WO 2013/186329 A1 | 12/2013 |
| WO | WO 2014/094799 | 6/2014 |
| WO | WO 2016/124670 A1 | 8/2016 |
| WO | WO 2016/124702 A1 | 8/2016 |
| WO | WO 2017/013129 | 1/2017 |
| WO | WO 2017/013136 | 1/2017 |

OTHER PUBLICATIONS

Advisory Action corresponding to U.S. Appl. No. 11/732,632 dated Jun. 30, 2010.
Advisory Action corresponding to U.S. Appl. No. 12/072,959 dated May 18, 2010.
Baker et al. (1994) Protein Expression Using Cotranslational Fusion and Cleavage of Ubiquitin. The Journal of Biological Chemistry 269(41):25381-25386.
Beal et al. (1996) Surface hydrophobic residues of multiubiquitin chains essential for proteolytic targeting. PNAS 93:861-866.
Beste et al. (1999) Small antibody-like proteins with prescribed ligand specificities derived from the lipocalin fold. PNAS 96:1898-1903.
Birchler et al. (1999) Selective targeting and photocoagulation of ocular angiogenesis mediated by a phage-derived human antibody fragment. Nature Biotechnology 17:984-988.
Bofill et al. (2005) Engineering Stabilising beta-Sheet Interactions into a Conformationally Flexible Region of the Folding Transition State of Ubiquitin. Journal of Molecular Biology 353(2):373-384.
Bolton et al. (2001) Structure and Properties of a Dimeric N-terminal Fragment of Human Ubiquitin. Journal of Molecular Biology 314(4):773-787.
Borsi et al. (2003) Selective targeted delivery of TNFα to tumor blood vessels. Blood 102(13):4384-4392.
Brinkmann et al. (1993) A recombinant immunotoxin containing a disulfide-stabilized Fv-fragment. PNAS 90:7538-7542.
Brinkmann et al. (1997) Stabilization of a Recombinant Fv Fragment by Base-Loop Interconnection and VH-VL Permutation. Journal of Molecular Biology 268:107-117.
Buchberger et al. (2001) The UBX Domain: A Widespread Ubiquitin-Like Module. Journal of Molecular Biology 307(1):17-24.
Burch & Haas (1994) Site-directed mutagenesis of ubiquitin. Differential roles for arginine in the interaction with ubiquitin-activating enzyme. Biochemistry 33(23):7300-7308.
Campion et al. (1990) Biochemical Properties of Site-Directed Mutants of Human Epidermal Growth Factor: Importance of Solvent-Exposed Hydrophobic Residues of the Amino-Terminal Domain in Receptor Binding Biochemistry 29(42):9988-9993.
Connolly (1983) Solvent-Accessible Surfaces of Proteins and Nucleic Acids. Science 221(4612):709-713.
Corrected Notice of Allowability corresponding to U.S. Appl. No. 11/656,646 dated Sep. 26, 2013.
Database Geneseq online Aug. 18, 2011 (Aug. 18, 2011)Heteromultimeric modified ubiquitin protein, SEQ ID 44., XP002756535, retrieved from EBI accession No. GSP:AZJ58575 Database accession No. AZJ58575.
Database Geneseq online Dec. 4, 2014 (Dec. 4, 2014)Anti-EGFR1 antibody light chain-TGF beta RII fusion protein, SEQ: 30., XP002756536, retrieved from EBI accession No. GSP:BBP24113 Database accession No. BBP24113.
Daugherty et al. (1998) Antibody affinity maturation using bacterial surface display. Protein Engineering 11(9):825-832.
De Kruif et al. (1995) Selection and Application of Human Single Chain Fv Antibody Fragments from a Semi-synthetic Phage Antibody Display Library with Designed CDR3 Regions. Journal of Molecular Biology 248:97-105.
Decision to Grant corresponding to Russian Patent Application No. 2012115491/10(023353) dated Nov. 20, 2014.
Deed of Grant corresponding to Australian Patent No. 2010332932 dated May 2, 2013.
Deed of Grant corresponding to Australian Patent No. 2010332938 dated Apr. 4, 2013.
Dikic et al. (2009) Ubiquitin-binding domains—from structures to functions. Nature Reviews 10:659-671.
Ebersbach et al. (2007) Affilin-Novel Binding Molecules Based on Human (-B-Crystallin, an All (-Sheet Protein. Journal of Molecular Biology 372:172-185.
Ecker et al. (1987) Gene Synthesis, Expression, Structures, and Functional Activities of Site-specific Mutants of Ubiquitin. The Journal of Biological Chemistry 262(29):14213-14221.
Ermolenko et al. (2003) Noncharged amino acid residues at the solvent-exposed positions in the middle and at the C terminus of the alpha-helix have the same helical propensity. Protein Science 12(6):1169-1176.
European Search Report corresponding to European Patent Application No. 06 118 519.5-2401 dated Apr. 2, 2007.
European Search Report corresponding to European Patent Application No. 10 181 802.9-2401 dated Feb. 10, 2011.
European Search Report corresponding to European Patent Application No. 09 176 574.3-2401.
Fiedler et al. (2006) Affilintm Molecules: Novel Ligands for Bioseparation. Food and Bioproducts Processing. 84(C1):3-8.
Finucane et al. (1999a) Core-Directed Protein Design. I. An Experimental Method for Selecting Stable Proteins from Combinatorial Libraries. Biochemistry 38:11604-11612.
Finucane et al. (1999b) Core-Directed Protein Design. II. Rescue of a Multiply Mutated and Destabilized Variant of Ubiquitin. Biochemistry 38(36):11613-11623.
Friedman et al. (2009) Engineering and characterization of a bispecific HER2 X EGFR-binding affibody molecule. Biotechnology and applied biochemistry academic press US 54(2):121-131.
Gebauer & Skerra (2009) Engineered protein scaffolds as next-generation antibody therapeutics. Current Opinion in Chemical Biology 13(3):245-255.
Grabulovski et al. (2007) A Novel, Non-immunogenic Fyn SH3-derived Binding Protein with Tumor Vascular Targeting Properties. The Journal of Biological Chemistry 282(5):3196-3204.
Guo et al. (2004) Protein tolerance to random amino acid change. PNAS 101(25):9205-9210.
Hanes & Plückthun (1997) In vitro selection and evolution of functional proteins by using ribosome display. PNAS 94(10):4937-4942.

(56) References Cited

OTHER PUBLICATIONS

Hanes et al. (1998) Ribosome display efficiently selects and evolves high-affinity antibodies in vitro from immune libraries PNAS 95:14130-14135.
Hanes et al. (2000) Picomolar affinity antibodies from a fully synthetic naive library selected and evolved by ribosome display. Nature Biotechnology 18:1287-1292.
He & Taussig (1997) Antibody-ribosome-mRNA (ARM) complexes as efficient selection particles for in vitro display and evoluation of antibody combining sites. Nucleic Acids Research 25(24):5132-5134.
Hershko & Ciechanover (1998) The Ubiquitin System. Annu Rev Biochem 67:425-479.
Hey et al. (2005) Artificial, non-antibody binding proteins for pharmaceutical and industrial applications. TRENDS in Biotechnology 23(10):514-522.
Humphrey et al. (1990) Anti-synthetic peptide antibody reacting at the fusion junction of deletion-mutant epidermal growth factor receptors in human glioblastoma. Proc Natl Acad Sci. 87:4207-4211.
International Preliminary Report on Patentability (Chapter I of the Patent Cooperation Treaty) corresponding to International Patent Application No. PCT/EP2016/052345 dated Aug. 8, 2017.
International Preliminary Report on Patentability (Chapter I of the Patent Cooperation Treaty) corresponding to International Patent Application No. PCT/EP2007/062375 dated May 19, 2009.
International Preliminary Report on Patentability (Chapter I of the Patent Cooperation Treaty) corresponding to International Patent Application No. PCT/EP2010/069665 dated Jun. 19, 2012.
International Preliminary Report on Patentability corresponding to International Patent Application No. PCT/EP2004/005730 dated May 13, 2005.
International Preliminary Report on Patentability corresponding to International Patent Application No. PCT/EP2016/067216 dated Jan. 23, 2018.
International Search Report and Written Opinion corresponding to International Patent Application No. PCT/EP2016/052408 dated May 2, 2016.
International Search Report corresponding to International Patent Application No. PCT/EP2000/006698 dated Feb. 2, 2001.
International Search Report corresponding to International Patent Application No. PCT/EP2004/005730 dated Oct. 5, 2004.
International Search Report corresponding to International Patent Application No. PCT/EP2005/010932 dated Apr. 11, 2006.
International Search Report corresponding to International Patent Application No. PCT/EP2007/062375 dated Apr. 25, 2008.
International Search Report corresponding to International Patent Application No. PCT/EP2010/069665 dated Apr. 13, 2011.
International Search Report corresponding to International Patent Application No. PCT/EP2010/069674 dated Jun. 17, 2011.
International Search Report corresponding to International Patent Application No. PCT/EP2012/061455 dated Oct. 25, 2012.
International Search Report corresponding to International Patent Application No. PCT/EP2011/002962 dated Mar. 19, 2012.
International Search Report corresponding to International Patent Application No. PCT/EP2012/061459 dated Sep. 24, 2012.
International Search Report corresponding to International Patent Application No. PCT/EP2013/062310 dated Aug. 2, 2013.
International Search Report corresponding to International Application No. PCT/EP2016/067207 dated Sep. 29, 2016.
International Search Report and Written Opinion corresponding to International Application No. PCT/EP2016/067216 dated Oct. 12, 2016.
International Search Report and Written Opinion corresponding to International Application No. PCT/EP2016/066774 dated Sep. 14, 2016.
Interview Summary and Corrected Notice of Allowability corresponding to U.S. Appl. No. 11/283,332 dated Jul. 1, 2014.
Interview Summary and Corrected Notice of Allowability corresponding to U.S. Appl. No. 12/072,959 dated Jun. 27, 2014.
Interview Summary correponding to U.S. Appl. No. 11/283,332 dated Dec. 13, 2013.
Jackson (2006) Ubiquitin: a small protein folding paradigm. Org Biomol Chem 4(10):1845-1853.
Khorasanizadeh et al. (1993) Folding and stability of a tryptophan-containing mutant of ubiquitin. Biochemistry 32(27):7054-7063.
Kiel & Serrano (2006) The Ubiquitin Domain Superfold: Structure-based Sequence Alignments and Characterization of Binding Epitopes. Journal of Molecular Biology 355(4):821-844.
Knappik et al. (2000) Fully Synthetic Human Combinatorial Antibody Libraries (HuCAL) Based on Modular Consensus Frameworks and CDRs Randomized with Trinucleotides. Journal of Molecular Biology 296:57-86.
Koide et al. (1998)The Fibronectin Type III Domain as a Scaffold for Novel Binding Proteins. Journal of Molecular Biology 284:1141-1151.
Kolchanov & Shindyalov (1988) Single amino acid substitutions producing instability of globular proteins. Calculation of their frequencies in the entire mutational spectra of the alpha- and beta-subunits of human hemoglobin. Journal of Molecular Evolution 27:154-162.
Krantz et al. (2004) Discerning the Structure and Energy of Multiple Transition States in Protein Folding using $\Psi$-Analysis. Journal of Molecular Biology 337(2):463-475.
Krippner-Heidenreich et al. (2008) Single-chain TNF, a TNF derivative with enhanced stability and antitumoral activity. Journal of Immunology 180:8176-8183.
Ku & Schultz (1995) Alternative protein frameworks for molecular recognition. PNAS 92:6552-6556.
Larsen & Wang. (2002) The Ubiquitin Superfamily: Members, Features, and Phylogenies. Journal of Proteome Research 1:411-419.
Laub et al. (1995) Localized solution structure refinement of an F45W variant of ubiquitin using stochastic boundary molecular dynamics and NMR distance restraints. Protein Science 4:973-982.
Lazar & Wang (1997) H.De novo design of the hydrophobic core of ubiquitin. Protein Science 6:1167-1178.
Lipovsek & Plückthun (2004) In-vitro protein evolution by ribosome display and mRNA display. Journal of Immunological Methods 290:51-67.
Lo et al. (2009) Structural Basis for Recognition of Diubiquitins by NEMO. Molecular Cell 33:602-615.
Loladze et al. (2005) Both helical propensity and side-chain hydrophobicity at a partially exposed site in alpha-helix contribute to the thermodynamic stability of ubiquitin. Proteins 58(1):1-6.
Lorey et al. (2014) Novel ubiquitin-derived high affinity binding proteins with tumor targeting properties. Journal of Biological Chemistry. 289(12):8493-8507.
Mayr et al. (1994) Domain Interactions and Connecting Peptides in Lens Crystallins. Journal of Molecular Biology 235:84-88.
McConnell & Hoess (1995) Tendamistat as a Scaffold for Conformationally Constrained Phage Peptide Libraries. The Journal of Molecular Biology 250:460-470.
Miura et al. (1999) Characterization of the Binding Interface between Ubiquitin and Class I Human Ubiquitin-conjugating Enzyme 2b by Multidimensional Heteronuclear NMR Spectroscopy in Solution Journal of Molecular Biology 290:213-228.
Müller & Skerra (1994) A.Grafting of a High-Affinity Zn(II)-Binding Site on the β-Barrel of Retional-Binding Protein Results in Enhanced Folding Stability and Enables Simplified Purification. Biochemistry 33(47):14126-14135.
Müller et al. (2001) SUMO, ubiquitin's mysterious cousin. Nat. Rev. Mol. Cell Biol 2:202-210.
Nord et al. (1997) Binding proteins selected from combinatorial libraries of an (-helical bacterial receptor domain. Nature Biotechnology 15:772-777.
Notice of Allowance corresponding to U.S. Appl. No. 10/030,605 dated Apr. 14, 2009.
Notice of Allowance corresponding to U.S. Appl. No. 11/283,332 dated Jun. 6, 2014.
Notice of Allowance corresponding to U.S. Appl. No. 11/732,632 dated Aug. 23, 2010.

(56) References Cited

OTHER PUBLICATIONS

Notice of Allowance corresponding to U.S. Appl. No. 11/656,646 dated Aug. 27, 2013.
Notice of Allowance corresponding to U.S. Appl. No. 12/072,959 dated Jun. 3, 2014.
Notice of Allowance corresponding to U.S. Appl. No. 12/514,550 dated Sep. 10, 2013.
Notice of Allowance corresponding to U.S. Appl. No. 13/142,195 dated Aug. 4, 2014.
Notice of Allowance corresponding to U.S. Appl. No. 13/144,809 dated Mar. 3, 2014.
Notice of Allowance corresponding to U.S. Appl. No. 14/126,358 dated Sep. 9, 2016.
Notification Concerning Transmittal of International Preliminary Report on Patentability (Chapter I of the Patent Cooperation Treaty) corresponding to International Patent Application No. PCT/EP2016/052345 dated Apr. 11, 2016.
Notification Concerning Transmittal of International Preliminary Report on Patentability (Chapter I of the Patent Cooperation Treaty) corresponding to International Patent Application No. PCT/EP2010/069666 dated Jun. 28, 2012.
Notification Concerning Transmittal of International Preliminary Report on Patentability (Chapter I of the Patent Cooperation Treaty) corresponding to International Patent Application No. PCT/EP2010/069674 dated Jun. 28, 2012.
Notification of Transmittal of Translation of the International Preliminary Report on Patentability (Chapter I of the Patent Cooperation Treaty) corresponding to International Patent Application No. PCT/EP2004/005730 dated Apr. 13, 2006.
Notification of Transmittal of Translation of the International Preliminary Report on Patentability (Chapter I or Chapter II of the Patent Cooperation Treaty) corresponding to International Patent Application No. PCT/EP2005/010932 dated May 3, 2007.
Nygren & Uhlen (1997) Scaffolds for engineering novel binding sites in proteins. Current Opinion in Structural Biology 7:463-469.
Office Action corresponding to Australian Patent Application No. 2012268970 dated Aug. 27, 2015.
Office Action corresponding to Canadian Patent Application No. 2,837,804 dated May 1, 2015.
Office Action corresponding to Canadian Patent Application No. 2,778,871 dated Jan. 30, 2014.
Office Action corresponding to Chinese Patent Application No. 201080056911.6 dated Jul. 31, 2013. Translation.
Office Action corresponding to European Patent Application No. 00 944 034.8-2401 dated Oct. 7, 2004.
Office action corresponding to European Patent Application No. EP 10 787 815.9-1410 dated Aug. 13, 2013.
Office Action corresponding to Japanese Patent Application No. 2012-504036 dated Aug. 26, 2013.
Office Action corresponding to Japanese Patent Application No. 2012-542583 dated Apr. 22, 2014.
Office Action corresponding to Korean Patent Application No. 10-2011-7018847 dated Jan. 30, 2013. Translation.
Office Action corresponding to Russian Patent Application No. 2012114662/10(022146) dated Sep. 8, 2014. (with Translation).
Office Action corresponding to Russian Patent Application No. 2012115491 dated Dec. 24, 2013.
Office Action corresponding to Russian Patent Application No. 2012114662/10(022146) dated Dec. 18, 2013.
Office Action corresponding to U.S. Appl. No. 12/072,959 dated Jan. 27, 2009.
Office Action corresponding to U.S. Appl. No. 10/030,605 dated Sep. 21, 2004.
Office Action corresponding to U.S. Appl. No. 10/030,605 dated Feb. 15, 2005.
Office Action corresponding to U.S. Appl. No. 10/030,605 dated Aug. 10, 2005.
Office Action corresponding to U.S. Appl. No. 10/030,605 dated Apr. 12, 2006.
Office Action corresponding to U.S. Appl. No. 10/030,605 dated Feb. 28, 2007.
Office Action corresponding to U.S. Appl. No. 10/030,605 dated Nov. 16, 2007.
Office Action corresponding to U.S. Appl. No. 11/656,646 dated Sep. 1, 2009.
Office Action corresponding to U.S. Appl. No. 11/656,646 dated May 25, 2010.
Office Action corresponding to U.S. Appl. No. 10/030,605 dated Jul. 1, 2008.
Office Action corresponding to U.S. Appl. No. 11/656,646 dated Nov. 13, 2009.
Office Action corresponding to U.S. Appl. No. 11/283,332 dated Jan. 9, 2008.
Office Action corresponding to U.S. Appl. No. 11/283,332 dated May 30, 2008.
Office Action corresponding to U.S. Appl. No. 11/283,332 dated Nov. 28, 2008.
Office Action corresponding to U.S. Appl. No. 11/283,332 dated Sep. 4, 2009.
Office Action corresponding to U.S. Appl. No. 11/283,332 dated Sep. 3, 2013.
Office Action corresponding to U.S. Appl. No. 12/072,959 dated Jul. 24, 2008.
Office Action corresponding to U.S. Appl. No. 12/072,959 dated Aug. 30, 2013.
Office Action corresponding to U.S. Appl. No. 11/283,332 dated Mar. 3, 2010.
Office Action corresponding to U.S. Appl. No. 12/072,959 dated Jan. 5, 2010.
Office Action corresponding to U.S. Appl. No. 11/732,632 dated Jun. 3, 2009.
Office Action corresponding to U.S. Appl. No. 11/732,632 dated Aug. 21, 2009.
Office Action corresponding to U.S. Appl. No. 11/732,632 dated Mar. 19, 2010.
Office Action corresponding to U.S. Appl. No. 12/514,550 dated Aug. 3, 2011.
Office Action corresponding to U.S. Appl. No. 12/514,550 dated Sep. 15, 2011.
Office Action corresponding to U.S. Appl. No. 12/514,550 dated Mar. 12, 2012.
Office Action corresponding to U.S. Appl. No. 13/142,195 dated Feb. 11, 2013.
Office Action corresponding to U.S. Appl. No. 13/142,195 dated May 29, 2013.
Office Action corresponding to U.S. Appl. No. 13/142,195 dated Feb. 4, 2014.
Office Action corresponding to U.S. Appl. No. 13/144,809 dated Oct. 18, 2013.
Office Action corresponding to U.S. Appl. No. 13/516,002 dated Jan. 26, 2015.
Office Action corresponding to U.S. Appl. No. 13/516,002 dated Apr. 6, 2015.
Office Action corresponding to U.S. Appl. No. 14/126,341 dated May 1, 2015.
Office Action corresponding to U.S. Appl. No. 14/126,341 dated Sep. 29, 2015.
Office Action corresponding to U.S. Appl. No. 14/126,358 dated Apr. 6, 2016.
Office Action corresponding to U.S. Appl. No. 14/407,213 dated May 25, 2016.
Office Action Restriction Requirement corresponding to U.S. Appl. No. 14/126,358 dated Oct. 28, 2015.
Office Action Restriction Requirement corresponding to U.S. Appl. No. 14/407,213 dated Jan. 21, 2016.
Ohashi et al. (2007) Efficient protein selection based on ribosome display system with purified components. Biochemical and Biophysical Research Communications 352:270-276.
Pack & Pluckthun (1992) A.Miniantibodies: Use of Amphipathic Helices to Produce Functional, Flexibly Linked Dimeric Fv Fragments with High Avidity in *Escherichia coli*. Biochemsitry 31(6):1579-1584.

(56) References Cited

OTHER PUBLICATIONS

Raasi Shahri et al. (2004) Binding of polyubiquitin chains to ubiquitin-associated (UBA) domains of HHR23A. J. Mol. Biol. 34:1367-1379.
Rahighi et al. (2009) Specific Recognition of Linear Ubiquitin Chains by NEMO is Important for NF-κB Activation. Cell 136:1098-1109.
Search Report corresponding to Chinese Patent Application No. 201080056911.6 dated Jun. 14, 2013. Translation.
Skerra (2000) Engineered protein scaffolds for molecular recognition. Journal of Molecular Recognition 13(4):167-187.
Skerra et al. (2007) Alternative non-antibody scaffolds for molecular recognition. Current Opinion in Biotechnology 18(4):295-304.
Smith et al. (1998) Small Binding Proteins Selected from a Conbinatorial Repertoire of Knottins Displayed on Phage. Journal of Molecular Biology 277(2):317-332.
Susan et al. (2014) Novel Ubiquitin-derived High Affinity Binding Proteins with Tumor Targeting Properties. J of Bio Chem 289(12):8493-8507.
Ubiquitin-like Superfamily (2004) pp. 1-4.
Weidle et al. (2013) The Emerging Role of New Protein Scaffold-based Agents for Treament of Cancer. Caner Genomics & Proteomics 10(4):155-168.
Wells & Lowmann (1992).Rapid evolution of peptide and protein binding properties in vitro. Current Opinion in Biotechnology 3:355-362.
Wells (1990) Additivity of Mutational Effects in Proteins. Biochemistry 29(37):8509-8517.
Yeh et al. (2000) Ubiquitin-like proteins: new wines in new bottles. Gene 248(1-2):1-14.
Zahnd et al. (2007) Ribosome display: selecting and evolving proteins in vitro that specifically bind to a target. Nature Methods 4(3):269-279.
Zhang et al. (1997) Directed evolution of a fucosidase from a galactosidase by DNA shuffling and screening. PNAS 94:4504-4509.
Notice of Allowance corresponding to U.S. Appl. No. 15/744,054 dated Jan. 9, 2020.
Office Action Restriction Requirement corresponding to U.S. Appl. No. 15/548,976 dated Sep. 9, 2019.
Office Action (Restriction Requirement) corresponding to U.S. Appl. No. 15/744,053 dated Nov. 4, 2019.
Office Action (Restriction Requirement) corresponding to U.S. Appl. No. 15/744,053 dated Feb. 4, 2019.
Office Action corresponding to U.S. Appl. No. 15/548,976 dated Mar. 17, 2020.

\* cited by examiner

FIG. 1B

| Pos | | | | | | |
|---|---|---|---|---|---|---|
| 1 | X | A | V | Q | N | P |
| 2 | X | D | A | Q | Q | |
| 3 | X | A | N | S | | |
| 4 | X | K | Q | N | | |
| 5 | X | H | F | | | |
| 6 | X | D | N | A | S | |
| 7 | X | E | K | | | |
| 8 | X | D | E | A | | |
| 9 | Q | Q | | | | |
| 10 | Q | Q | | | | |
| 11 | X | S | N | | | |
| 12 | A | A | | | | |
| 13 | F | F | | | | |
| 14 | Y | Y | | | | |
| 15 | X | E | Q | | | |
| 16 | X | V | I | | | |
| 17 | L | L | | | | |
| 18 | X | H | N | | | |
| 19 | X | L | M | | | |
| 20 | P | P | | | | |
| 21 | X | N | S | D | | |
| 22 | L | L | | | | |
| 23 | X | T | N | | | |
| 24 | X | E | A | | | |
| 25 | X | D | E | | | |
| 26 | Q | Q | | | | |
| 27 | R | R | | | | |
| 28 | X | N | A | S | | |
| 29 | X | G | A | | | |
| 30 | F | F | | | | |
| 31 | I | I | | | | |
| 32 | Q | Q | | | | |
| 33 | S | S | | | | |
| 34 | L | L | | | | |
| 35 | K | K | | | | |
| 36 | D | D | | | | |
| 37 | D | D | | | | |
| 38 | P | P | | | | |
| 39 | S | S | | | | |
| 40 | X | V | Q | T | | |
| 41 | S | S | | | | |
| 42 | X | K | T | A | | |
| 43 | X | E | N | S | | |
| 44 | X | V | L | I | | |
| 45 | L | L | | | | |
| 46 | X | G | A | | | |
| 47 | E | E | | | | |
| 48 | A | A | | | | |
| 49 | X | K | Q | | | |
| 50 | K | K | | | | |
| 51 | L | L | | | | |
| 52 | X | N | D | S | | |
| 53 | X | D | E | | | |
| 54 | X | S | A | | | |
| 55 | Q | Q | | | | |
| 56 | X | A | P | | | |
| 57 | P | P | | | | |
| 58 | X | K | P | | | |

FIG. 2

```
NAAQHAKEQQNAFYEILHLPNLTEDQRAAFIQSLKDDPSVSKEILGEAKKLNDAQAPP  (SEQ ID NO: 9)
NAAQHDKEQQNAFYEILHLPNLTEDQRAAFIQSLKDDPSVSKEILGEAKKLNDAQAPP  (SEQ ID NO: 10)
NAAQHSKEQQNAFYEILHLPNLTEDQRSAFIQSLKDDPSVSKEILGEAKKLNDAQAPP  (SEQ ID NO: 11)
NAAQHSKDQQSAFYEILHLPNLTEDQRSAFIQSLKDDPSVSKEILGEAKKLNDAQAPP  (SEQ ID NO: 12)
PAAQHDKDQQSAFYEILHLPNLTEDQRSAFIQSLKDDPSVSKEILGEAKKLNDAQAPP  (SEQ ID NO: 13)
PAAKHDKDQQSAFYEILHLPNLTEDQRSAFIQSLKDDPSVSKEILGEAKKLNDAQAPP  (SEQ ID NO: 14)
ADNKFDEAQQSAFYEILHLPNLTEDQRAAFIQSLKDDPSVSKEILGEAKKLNDAQAPP  (SEQ ID NO: 15)
ADSKFDEAQQSAFYEILHLPNLTEDQRAAFIQSLKDDPSVSKEILGEAKKLNDAQAPP  (SEQ ID NO: 16)
ADSKFDEAQQSAFYEILHLPNLTEDQRAAFIQSLKDDPSVSKSLLGEAKKLNDAQAPP  (SEQ ID NO: 17)
ADSKFDEAQQSAFYEILHLPDLTEDQRAAFIQSLKDDPSVSKSLLGEAKKLNDAQAPP  (SEQ ID NO: 18)
ADSKFDEAQQSAFYEILHLPSLTEDQRAAFIQSLKDDPSVSKSLLGEAKKLNDAQAPP  (SEQ ID NO: 19)
ADSKFDEAQQSAFYEILHLPSLTEDQRAAFIQSLKDDPSTSKSLLGEAKKLNDAQAPP  (SEQ ID NO: 20)
ADSKFDEAQQSAFYEILHLPSLTEDQRAAFIQSLKDDPSTSKSLLGEAKKLDDAQAPP  (SEQ ID NO: 21)
ADSKFDEAQQSAFYEILHLPSLTEDQRAAFIQSLKDDPSTSKSLLGEAKKLSDAQAPP  (SEQ ID NO: 22)
PAAKHDKDQQSAFYEILHLPSLTEDQRAAFIQSLKDDPSTSKSILGEAKKLNDAQAPP  (SEQ ID NO: 23)
NAAQHDKEQQNAFYEILHLPNLTEDQRNAFIQSLKDDPSVSKEILGEAKKLNDAQAPK  (SEQ ID NO: 24)
ADNKFDEAQQSAFYEILHLPNLTEDQRNAFIQSLKDDPSVSKEILGEAKKLNDAQAPK  (SEQ ID NO: 25)
NAAKHDKDQQSAFYEILHLPNLTEDQRNAFIQSLKDDPSVSKEILGEAKKLNDAQAPP  (SEQ ID NO: 26)
NAAQHDKDQQSAFYEILHLPNLTEEQRNAFIQSLKDDPSVSKEILAEAKKLNDAQAPK  (SEQ ID NO: 27)
NAAKFDEAQQSAFYEILHLPNLTEEQRNAFIQSLKDDPSVSKEVLGEAQKLNDSQAPK  (SEQ ID NO: 28)
QQAQHDEAQQSAFYQVLHLPNLTADQRNAFIQSLKDDPSQSAEVLGEAQKLNDSQAPK  (SEQ ID NO: 29)
VDAQHDEDQQSAFYEILHLPNLTEEQRNAFIQSLKDDPSQSAEILAEAKKLNESQAPK  (SEQ ID NO: 30)
```

FIG. 3A
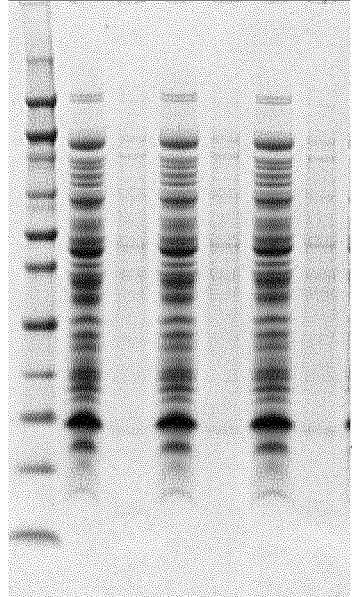
FIG. 3B
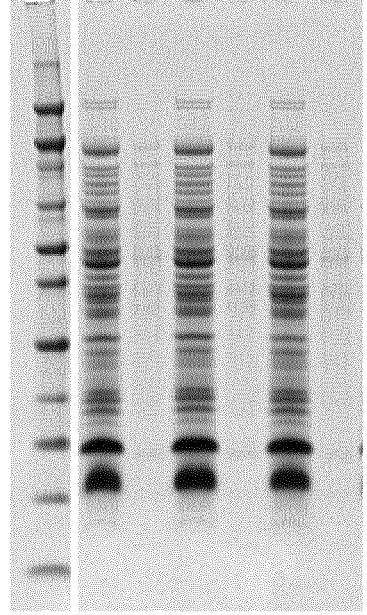
FIG. 4
FIG. 4A
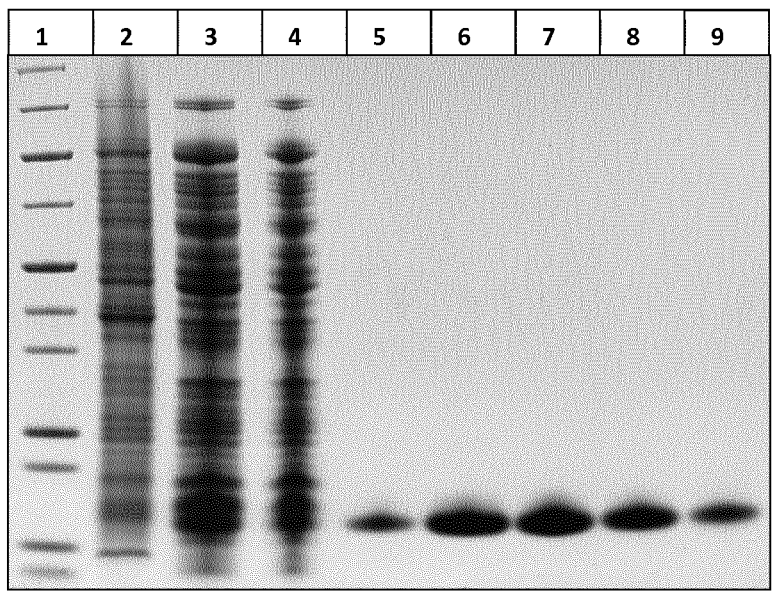

148463

154256

IMMUNOGLOBULIN-BINDING PROTEINS AND THEIR USE IN AFFINITY PURIFICATION

FIELD OF THE INVENTION

The present invention relates to non-natural binding proteins comprising one or more non-natural immunoglobulin (Ig) binding domains. The invention further relates to compositions such as affinity matrices comprising the non-natural Ig-binding proteins of the invention. The invention also relates to a use of these Ig-binding proteins or compositions for affinity purification of immunoglobulins and to methods of affinity purification using the Ig binding proteins of the invention.

BACKGROUND OF THE INVENTION

Many biotechnological and pharmaceutical applications require the removal of contaminants from a sample containing antibodies. An established procedure for capturing and purifying antibodies is affinity chromatography using the bacterial cell surface protein A from *Staphylococcus aureus* as selective ligand for immunoglobulins (see, for example, review by Huse et al, J. Biochem. Biophys. Methods 51, 2002: 217-231). Wild-type Protein A binds to the Fc region of IgG molecules with high affinity and selectivity and is stable at high temperatures and in a wide range of pH values. Variants of protein A with improved properties such as alkaline stability are available for purifying antibodies and various chromatographic matrices comprising protein A ligands are commercially available. However, in particular wild-type Protein A based chromatography matrices show a loss of binding capacity for immunoglobulins following exposure to alkaline conditions.

Technical Problems Underlying the Present Invention

Most large scale production processes for antibodies or Fc-containing fusion proteins use Protein A for affinity purification.

However, due to limitations of Protein A applications in affinity chromatography there is a need in the prior art to provide novel Ig binding proteins with improved properties that specifically bind to immunoglobulins in order to facilitate affinity purification of immunoglobulins. Thus, the specificity of Ig binding proteins for immunoglobulin with affinities of 1 µM, even of 100 nM or less is an important functional feature for an Ig binding protein for efficient purification of immunoglobulins.

Further, to maximally exploit the value of the chromatographic matrices comprising Ig binding proteins it is desirable to use the affinity ligand matrices multiple times. Between chromatography cycles, a thorough cleaning procedure is required for sanitization and removal of residual contaminants on the matrix. In this procedure, it is general practice to apply alkaline solutions with high concentrations of NaOH to the affinity ligand matrices. Wild-type Protein A or naturally occurring Protein A domains do not withstand such harsh alkaline conditions for an extended time and quickly lose binding capacity for immunoglobulin. Accordingly, there is a need in this field to obtain novel alkaline-stable proteins capable of binding immunoglobulins.

The present invention provides artificial immunoglobulin binding proteins that are particularly well-suited for affinity purification of immunoglobulins but overcome the disadvantages of the prior art. In particular, a significant advantage of the non-natural Ig binding proteins of the invention is their increased stability at high pH compared to naturally occurring Protein A domains.

The above overview does not necessarily describe all problems solved by the present invention.

SUMMARY OF THE INVENTION

In a first aspect the present invention relates to a non-natural, immunoglobulin (Ig) binding protein comprising one or more non-natural Ig-binding domains, wherein at least one non-natural Ig-binding domain comprises the amino acid sequence SEQ ID NO: 1.

In an embodiment of the first aspect, at least one non-natural Ig-binding domain comprises the amino acid sequence $X_1X_2X_3X_4X_5X_6X_7X_8QQX_{11}AFYX_{15}X_{16}LX_{18}X_{19}PX_{21}LX_{23}X_{24}X_{25}QRX_{28}X_{29}FIQSLKDDPSX_{40}SX_{42}X_{43}X_{44}LX_{46}EAX_{49}KLX_{52}X_{53}X_{54}QX_{56}PX_{58}$ (SEQ ID NO: 1), wherein $X_1$ is A, V, Q, N, or P; preferably N, V, P, or A;
$X_2$ is D, A, or Q; preferably D or A;
$X_3$ is A, S, or N;
$X_4$ is K, Q, or N; preferably K or Q;
$X_5$ is H or F;
$X_6$ is D, N, S, or A; preferably D, S, or A,
$X_7$ is E or K;
$X_8$ is D, E or A;
$X_{11}$ is S or N;
$X_{15}$ is E, D, or Q; preferably E;
$X_{16}$ is V or I; preferably I;
$X_{18}$ is H or N; preferably H;
$X_{19}$ is L or M; preferably L;
$X_{21}$ is N, S, or D;
$X_{23}$ is T or N; preferably T;
$X_{24}$ is E or A; preferably E;
$X_{25}$ is D or E;
$X_{28}$ is N, S, or A;
$X_{29}$ is G or A; preferably A;
$X_{40}$ is V or Q or T;
$X_{42}$ is K, T, or A; preferably K or A;
$X_{43}$ is E, N, or S; preferably E or S;
$X_{44}$ is V, L, or I;
$X_{46}$ is G or A;
$X_{49}$ is K or Q;
$X_{52}$ is N, S, or D;
$X_{53}$ is D or E;
$X_{54}$ is S or A;
$X_{56}$ is A or P; preferably A; and
$X_{58}$ is K or P;
and wherein the dissociation constant $K_D$ of said non-natural Ig-binding protein to human $IgG_1$ is 1 µM or less, preferably less than 500 nM, more preferably less than 100 nM. In a first embodiment, the invention relates to a binding protein comprising one or more non-natural Ig-binding domains, wherein at least one non-natural Ig-binding domain comprises the amino acid sequence shown in SEQ ID NO: 1 with the ability to bind to immunoglobulin even after alkaline treatment.

In a second aspect the present invention relates to a composition comprising the non-natural Ig-binding protein of the first aspect, preferably wherein the composition is an affinity separation matrix.

In a third aspect the present invention relates to a use of the non-natural Ig-binding protein of the first aspect or of the composition of the second aspect for affinity purification of immunoglobulins.

In a fourth aspect the present invention relates to a method of affinity purification of immunoglobulins comprising the steps of (a) providing a liquid containing an immunoglobulin; (b) providing an affinity separation matrix comprising an immobilized non-natural Ig-binding protein of the first aspect; (c) contacting said liquid and said affinity separation matrix, wherein said immunoglobulin binds to said immobilized Ig-binding protein; and (d) eluting said immunoglobulin from said matrix, thereby obtaining an eluate containing said immunoglobulin; and (e) optionally further comprising one or more washing steps carried out between steps (c) and (d).

In a fifth aspect the present invention relates to a method of generation of a non-natural, Ig-binding protein according to the first aspect, wherein each Ig-binding domain is obtainable by a shuffling process of at least two naturally occurring Ig-binding domains from a naturally occurring Ig-binding protein and optionally introducing further mutations.

In a sixth aspect the present invention relates to a nucleic acid molecule encoding a non-natural Ig-binding protein of the first aspect.

In a seventh aspect the present invention relates to a vector comprising the nucleic acid molecule of the sixth aspect.

In an eighth aspect the present invention relates to a host cell or a non-human host comprising the non-natural Ig-binding protein of the first aspect, a nucleic acid molecule of the sixth aspect, or a vector of the seventh aspect.

In a ninth aspect the present invention relates to a method for the production of a non-natural Ig-binding protein of the first aspect, comprising the step(s): a. culturing the host cell of the eight aspect under suitable conditions for the expression of the binding protein in order to obtain said non-natural immunoglobulin (Ig) binding protein; and b. optionally isolating said non-natural immunoglobulin (Ig) binding protein.

This summary of the invention does not necessarily describe all features of the present invention. Other embodiments will become apparent from a review of the ensuing detailed description.

BRIEF DESCRIPTION OF THE FIGURES

FIG. 1B. Generic sequence of IgG binding proteins of the invention (SEQ ID NO: 1). The numbers refer to the corresponding amino acid position in the binding protein; "X" refers to an amino acid that is selected from the amino acids as shown below the "X". For example, "X" in Position 2 can be selected from A, D, or Q.

FIG. 2. Amino acid sequences of selected non-natural Ig-binding proteins (SEQ ID NOs: 9-30)

FIG. 3. Analysis of IgG binding proteins expressed in HMS174(DE3) by denaturing SDS-PAGE. Soluble and insoluble fractions were generated and applied to the SDS-Gel. Main culture 7 h after inoculation (FIG. 3A) and 24 h after inoculation (FIG. 3B). Lane 1—molecular weight marker, soluble (lane 2) and insoluble (lane 3) fraction of 148464 (SEQ ID NO: 15), soluble (lane 4) and insoluble (lane 5) fraction of 148463 (SEQ ID NO: 14), soluble (lane 6) and insoluble (lane 7) fraction of 148461 (SEQ ID NO: 12). The grey arrow points to the approximate size of the expressed proteins.

FIG. 5. Analysis of the binding affinity of IgG binding proteins by ELISA. The assay was performed with Cetuximab (filled circles) and Adalimumab (empty circles) as on-targets and BSA (filled triangles) as off-target. The binding of the IgG binding proteins was analyzed via StrepTag with Strep-Tactin-HRP.

DETAILED DESCRIPTION OF THE INVENTION

Definitions

Figure 1A:
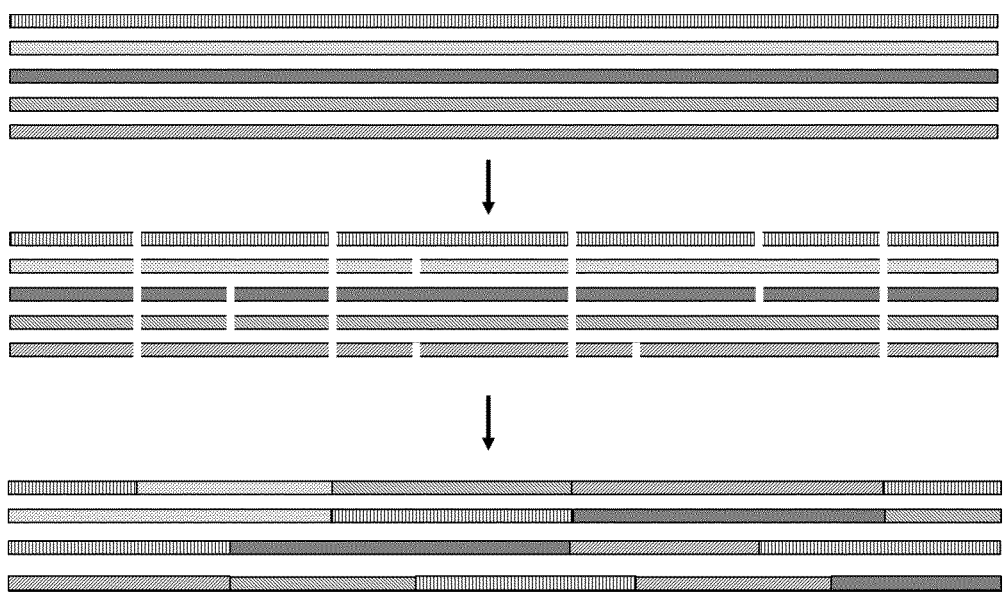
FIG. 1A. Illustration of the shuffling method for the generation of Ig binding proteins.
Figure 4B:
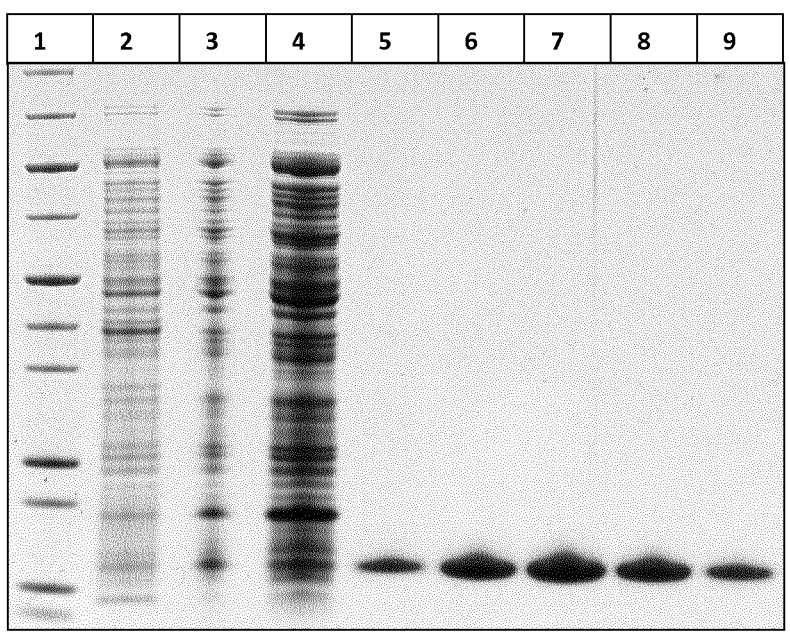
FIG. 4. Analysis of purified IgG binding proteins by denaturing SDS-PAGE. Expression and purification of 148461 (SEQ ID NO: 12) (FIG. 4A), and of 148471 (SEQ ID NO: 22) (FIG. 4B). Lane 1 molecular weight marker, lane 2 insoluble fraction, lane 3 soluble fraction, lane 4 flow-through StrepTactin column, lanes 5-9 HiLoad 16/600 Superdex 75 pg elution fractions.
Figure 5A:
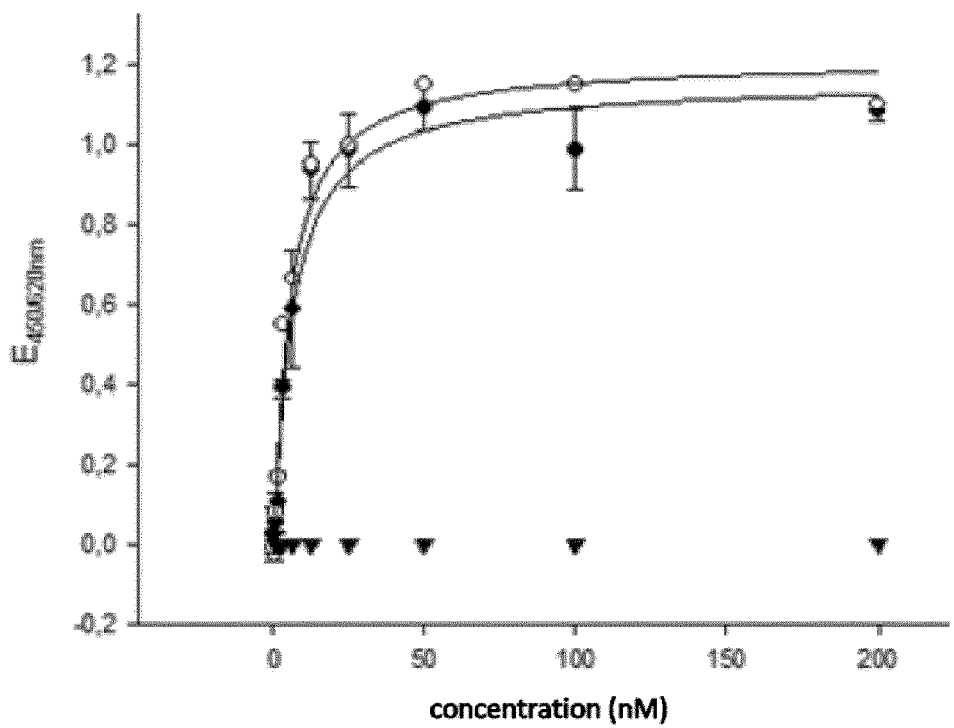
FIG. 5A. Ig binding protein 148472 (SEQ ID NO: 23); The $K_D$ for SEQ ID NO: 23 is 5.9 nM vs Cetuximab and 5.1 nM vs Adalimumab.
Figure 5B:
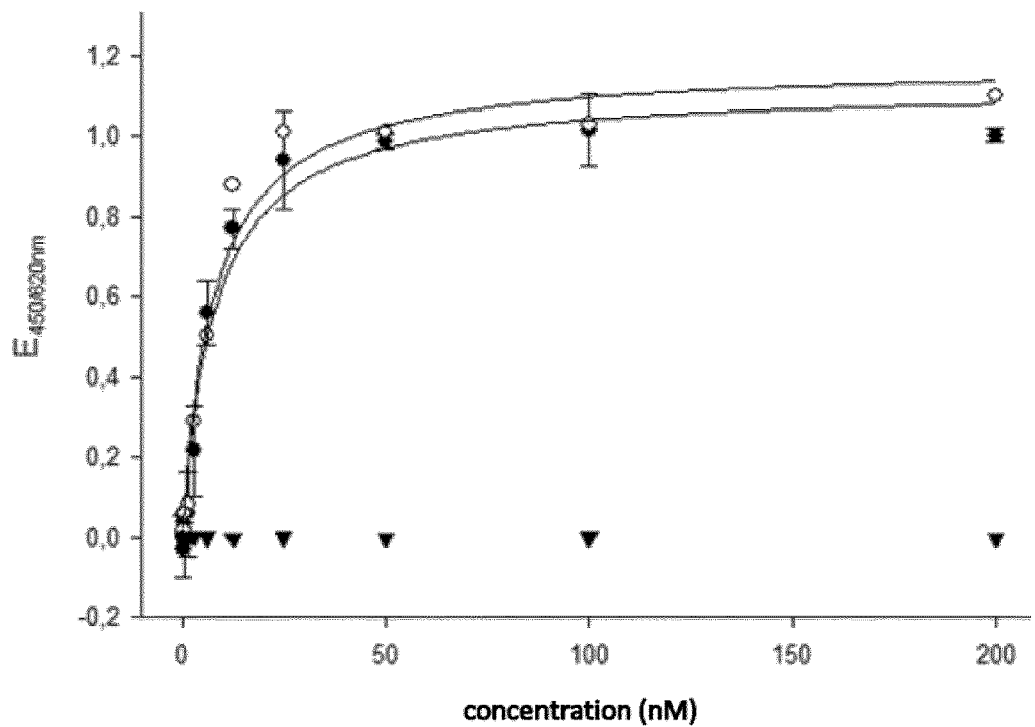
FIG. 5B. Ig binding protein 148461 (SEQ ID NO: 12). The $K_D$ for SEQ ID NO: 12 is 7.8 nM vs Cetuximab and 7.5 nM vs Adalimumab, Results for further IgG binding proteins of the invention compared to naturally occurring Protein A domains are shown in Table 2 (see Example 5).

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

The terms "protein" and "polypeptide" refer to any linear molecular chain of two or more amino acids linked by peptide bonds, and does not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well-known in the art. Thus, Ig binding proteins comprising two or more protein domains also fall under the definition of the term "protein" or "polypeptides".

In the context of the present invention, the term "immunoglobulin-binding protein" is used to describe proteins that are capable of specifically bind to the Fc region of an immunoglobulin. Due to this specific binding to the Fc region, the "immunoglobulin-binding proteins" of the invention are capable of binding to entire immunoglobulins, to immunoglobulin fragments comprising the Fc region, to fusion proteins comprising an Fc region of an immunoglobulin, and to conjugates comprising an Fc region of an immunoglobulin. While the "immunoglobulin-binding proteins" of the invention herein exhibit specific binding to the Fc region of an immunoglobulin, it is not excluded that "immunoglobulin-binding proteins" can additionally bind with reduced affinity to other regions, such as Fab regions of immunoglobulins.

Throughout this specification, the term "immunoglobulin-binding protein" is often abbreviated as "Ig binding protein" or "Ig-binding protein". Occasionally, both the long form and the abbreviated form are used at the same time, e.g. in the expression "immunoglobulin (Ig) binding protein".

In preferred embodiments of the present invention, the "immunoglobulin-binding protein" comprises one or more non-natural Ig-binding domains. As used herein, the term "immunoglobulin-binding domain" (often abbreviated as: Ig-binding domain) refers to a protein domain that is capable of specifically binding to the Fc region of an immunoglobulin. It is not excluded, though, that "immunoglobulin-binding domain" can additionally bind—with reduced affinity—to other regions, such as Fab regions of immunoglobulins. Due to the specific binding to the Fc region, the "immunoglobulin-binding domains" of the invention are capable to bind to entire immunoglobulins, to immunoglobulin fragments comprising the Fc region, to fusion proteins comprising an Fc region of an immunoglobulin, and to conjugates comprising an Fc region of an immunoglobulin.

In preferred embodiments of the invention, the "immunoglobulin-binding domains" are non-natural domains that exhibit a maximum of 85% sequence identity to naturally occurring Ig-binding domains, for example to domain C (SEQ ID NO: 7) or to domain B (SEQ ID NO: 6) or to domain E (SEQ ID NO: 3) or to domain D (SEQ ID NO: 4) or to domain A (SEQ ID NO: 5) of Staphylococcus aureus Protein A. A preferred non-natural Ig binding domain of the invention has identical amino acids in positions corresponding to positions Q9, Q10, A12, F13, Y14, L17, P20, L22, Q26, R27, F30, I31, Q32, S33, L34, K35, D36, D37, P38, S39, S41, L45, E47, A48, K50, L51, Q55, P57 of domain E, D, A, B, C, and to domain Z. The identity of an Ig-binding domain of the invention to naturally occurring domains E, D, A, B, C, and to domain Z is at least about 50% and maximal 85%.

As used herein, a first compound (e.g. an Ig binding protein of the invention) is considered to "bind" to a second compound (e.g. an antigen, such as a target protein, such as immunoglobulin), if it has a dissociation constant $K_D$ to said second compound of 500 µM or less, preferably 100 µM or less, preferably 50 µM or less, preferably 10 µM or less, preferably 1 µM or less, preferably 500 nM or less, preferably 100 nM or less, more preferably 50 nM or less, even more preferably 10 nM or less. The term "binding" according to the invention preferably relates to a specific binding. "Specific binding" means that an Ig binding protein of the invention binds stronger to an immunoglobulin for which it is specific compared to the binding to another non-immunoglobulin target. For example, the dissociation constant ($K_D$) for the target (e.g. immunoglobulin) to which the Ig binding protein binds specifically is more than 10-fold, preferably more than 20-fold, more preferably more than 50-fold, even more preferably more than 100-fold, 200-fold, 500-fold, or 1000-fold lower than the dissociation constant ($K_D$) for a target to which the binding protein does not bind specifically.

The term "dissociation constant" or "$K_D$" defines the specific binding affinity. As used herein, the term "$K_D$" (usually measured in "mol/L", sometimes abbreviated as "M") is intended to refer to the dissociation equilibrium constant of the particular interaction between a first protein and a second protein. In the context of the present invention, the term $K_D$ is particularly used to describe the binding affinity between an immunoglobulin-binding protein and an immunoglobulin. A high affinity corresponds to a low value of $K_D$. Thus, the expression "a $K_D$ of at least e.g. $10^{-7}$M"

means a value of $10^{-7}$ M or lower (binding more tightly). $1 \times 10^{-7}$ M corresponds to 100 nM. A value of $10^{-5}$ M and below down to $10^{-12}$ M can be considered as a quantifiable binding affinity. In accordance with the invention the affinity for the target binding should be in the range of 500 nM or less, more preferably below 100 nM, even more preferably 10 nM or less.

Methods for determining binding affinities, i.e. for determining the dissociation constant $K_D$, are known to a person of ordinary skill in the art and can be selected for instance from the following methods known in the art: Surface Plasmon Resonance (SPR) based technology, Bio-layer interferometry (BLI), enzyme-linked immunosorbent assay (ELISA), flow cytometry, fluorescence spectroscopy techniques, isothermal titration calorimetry (ITC), analytical ultracentrifugation, radioimmunoassay (RIA or IRMA) and enhanced chemiluminescence (ECL). Some of the methods are described in the Examples below.

The term "naturally occurring" as used herein refers to the fact that an object can be found in nature. For example, a polypeptide or polynucleotide sequence that is present in an organism that can be isolated from a source in nature and which has not been intentionally modified by man in the laboratory is naturally occurring. For example, naturally occurring Ig-binding domains can be isolated from the bacterium *Staphylococcus aureus*, for example Protein A domain C (SEQ ID NO: 7) or Protein A domain B (SEQ ID NO: 6) or Protein A domain E (SEQ ID NO: 3) or Protein A domain D (SEQ ID NO: 4) or Protein A domain A (SEQ ID NO: 5).

In contrast thereto, the term "non-natural", as used herein, refers to an object that is not naturally occurring, i.e. the term refers to an object that has been produced or modified by man. For example, a polypeptide or polynucleotide sequence that has been generated by man for example in a laboratory (e.g. by genetic engineering, by shuffling methods, or by chemical reactions, etc.) or intentionally modified is "non-natural". The terms "non-natural" and "artificial" are used interchangeably herein. For example, the Ig-binding proteins of the invention comprising at least one Ig binding domain are non-natural proteins.

The term "antibody" or "Ig" or "immunoglobulin" as used interchangeably herein in accordance with the present invention comprises proteins having a four-polypeptide chain structure consisting of two heavy chains and two light chains (immunoglobulin or IgG antibodies) with the ability to specifically bind an antigen. The term "antibody light chain" designates the small polypeptide subunit of an antibody chain which is composed of two tandem immunoglobulin domains, one constant domain and one variable domain that is important for antigen binding. The term "antibody heavy chain" designates the large polypeptide subunit of an antibody that determines the class or isotype of an antibody. Furthermore, also fragments or derivatives thereof, which still retain the binding specificity, are comprised in the term "antibody". Antibody fragments are understood herein are comprising fewer amino acid residues than an intact or complete antibody or antibody chain. The term "antibody" also includes embodiments such as chimeric (human constant domain, non-human variable domain), single chain and humanized (human antibody with the exception of non-human CDRs) antibodies. Full-length IgG antibodies consisting of two heavy chains and two light chains are most preferred in this invention. Heavy and light chains are connected via non-covalent interactions and disulfide bonds.

As used herein, the term "linker" refers in its broadest meaning to a molecule that covalenty joins at least two other molecules. In typical embodiments of the present invention, a "linker" is to be understood as a moiety that connects a first polypeptide with at least one further polypeptide. The second polypeptide may be the same as the first polypeptide or it may be different. Preferred in these typical embodiments are peptide linkers. This means that the peptide linker is an amino acid sequence that connects a first polypeptide with a second polypeptide, for example a first Ig binding domain with a second Ig binding domain. The peptide linker is connected to the first polypeptide and to the second polypeptide by a peptide bond, thereby generating a single, linear polypeptide chain. The length and composition of a linker may vary between at least one and up to 30 amino acids. More specifically, a peptide linker has a length of between 1 and 30 amino acids; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids. It is preferred that the amino acid sequence of the peptide linker is stable against proteases and/or does not form a secondary structure. Well-known are linkers comprised of small amino acids such as glycine and serine. The linkers can be glycine-rich (e.g., more than 50% of the residues in the linker can be glycine residues). Preferred are glycine-serine-linker of variable length consisting of glycine and serine residues only. In general, linkers of the structure $(SGGG)_n$ or permutations of SGGG, e.g. $(GGGS)_n$, can be used wherein n can be any number between 1 and 6, preferably 1 or 2 or 3. Also preferred are linkers comprising further amino acids. Preferred embodiments of the invention comprise linkers consisting of alanine, proline, and serine. It is preferred that a peptide linker consists of about 40% to 60% alanine, about 20% to 35% proline, and about 10% to 30% serine. It is preferred that the amino acids alanine, proline, and serine are evenly distributed throughout the linker amino acid sequence so that not more than a maximum of 2, 3, 4, or 5 identical amino acid residues are adjacent, preferably a maximum of 3 amino acids. Other linkers for the fusion of proteins are known in the art and can be used.

Exemplary linkers usable in the present invention are the following linkers: a linker having at least the amino acid sequence SG or any other linker, for example SGGGG [SEQ ID NO: 31], SGGGGSGGGG [SEQ ID NO: 32], GGGSGGGSGGGS [SEQ ID NO: 33], GGGGSGGGGSGGGGS [SEQ ID NO: 34], GGGGS [SEQ ID NO: 35], GGGS [SEQ ID NO: 36], SGGG [SEQ ID NO: 37], or $(GGGS)_n$ (i.e., n repetitions of SEQ ID NO: 36, wherein n is between 1 and 5 (e.g., n may be 1, 2, 3, 4, or 5)), $(SGGG)_n$ (i.e., n repetitions of SEQ ID NO: 37, wherein n is between 1 and 5 (e.g., n may be 1, 2, 3, 4, or 5), or SAAPAPSAPASAAPAPAPAPAPSPAAPAAS [SEQ ID NO: 41], ASPSPAAPAPAPSAASPAPAAPAPAASPAA [SEQ ID NO: 42], or ASPAPSAPSA [SEQ ID NO: 43]). Other linkers for the fusion of two IgG binding domains or two IgG binding proteins are also known in the art and can be used.

The term "fused" means that the components are linked by peptide bonds, either directly or via peptide linkers.

The term "fusion protein" relates to a protein comprising at least a first protein joined genetically to at least a second protein. A fusion protein is created through joining of two or more genes that originally coded for separate proteins. Thus, a fusion protein may comprise a multimer of identical or different binding proteins which are expressed as a single, linear polypeptide. It may comprise two, three, four or even more binding domains or binding proteins. In general, fusion proteins are generated artificially by recombinant DNA technology well-known to a skilled person. Ig binding proteins of the invention may be prepared by any of the many conventional and well-known techniques such as plain organic synthetic strategies, solid phase-assisted synthesis techniques or by commercially available automated synthesizers.

Preferably, the term "multimer" as used herein relates to a fusion protein comprising at least two IgG binding domains, preferably 2 (dimer), 3 (trimer), 4 (tetramer), 5 (pentamer), 6 (hexamer), 7 (heptamer), or 8 (octamer) IgG binding domains, more preferred 4, 5, or 6 IgG binding domains. In preferred embodiment, the Ig binding domains in a multimer are identical. In other embodiments, the Ig binding domains of a multimer can be different. One or more linker sequences are inserted between the domains of the multimer.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity.

To determine the sequence identity, the sequence of a query protein is aligned to the sequence of a reference protein. Methods for alignment are well-known in the art. For example, for determining the extent of an amino acid sequence identity of an arbitrary polypeptide relative to a reference amino acid sequence, the SIM Local similarity program is preferably employed (Xiaoquin Huang and Webb Miller (1991), Advances in Applied Mathematics, vol. 12: 337-357), that is freely available (see also: http://www.expasy.org/tools/sim-prot.html). For multiple alignment analysis ClustalW is preferably used (Thompson et al. (1994) Nucleic Acids Res., 22(22): 4673-4680). Preferably, the default parameters of the SIM Local similarity program or of ClustalW are used, when calculating sequence identity percentages.

In the context of the present invention, the extent of sequence identity between a modified sequence and the sequence from which it is derived is generally calculated with respect to the total length of the unmodified sequence, if not explicitly stated otherwise.

Each amino acid of the query sequence that differs from the reference amino acid sequence at a given position is counted as one difference. An insertion or deletion in the query sequence is also counted as one difference. For example, an insertion of a linker between two binding domains is counted as one difference compared to the reference sequence. The sum of differences is then related to the length of the reference sequence to yield a percentage of non-identity. The quantitative percentage of identity is calculated as 100 minus the percentage of non-identity.

The term "about", as used herein, encompasses the explicitly recited amounts as well as deviations therefrom of ±10%. More preferably, a deviation 5% is encompassed by the term "about".

The term "shuffled" as used herein refers to an assembly process resulting in novel non-natural sequences starting from a set of known sequences comprising the following steps: (a) providing a set of at least two sequences to be shuffled; (b) alignment of said sequences; and (c) assembly of new sequences from the aligned sequences wherein the amino acid at each position of the new sequence can be derived from the same position of any of the aligned sequences. Preferably, two or more consecutive amino acids are derived from one of the aligned sequences.

The term "chromatography" refers to separation technologies which employ a mobile phase and a stationary phase to separate one type of molecules (e.g., immunoglobulins) from other molecules (e.g. contaminants) in the sample. The liquid mobile phase contains a mixture of molecules and transports these across or through a stationary phase (such as a solid matrix). Due to the differential interaction of the different molecules in the mobile phase with the stationary phase, molecules in the mobile phase can be separated.

The term "affinity chromatography" refers to a specific mode of chromatography in which a ligand coupled to a stationary phase interacts with a molecule (i.e. immunoglobulin) in the mobile phase (the sample) i.e. the ligand has a specific affinity for the molecule to be purified. As understood in the context of the invention, affinity chromatography involves the addition of a sample containing an immunoglobulin to a stationary phase which comprises a chromatography ligand, such as an Ig binding protein of the invention. The terms "solid support" or "solid matrix" are used interchangeably for the stationary phase.

The terms "affinity matrix" or "affinity separation matrix" or "affinity chromatography matrix," as used interchangeably herein, refer to a matrix, e.g. a chromatographic matrix, onto which an affinity ligand (e.g., an Ig binding protein of the invention) is attached. The ligand (e.g., Ig binding protein) is capable of binding to a molecule of interest (e.g., an immunoglobulin or an Fc-containing protein) through affinity interaction which is to be purified or removed from a mixture.

The term "affinity purification" as used herein refers to a method of purifying immunoglobulins or Fc-containing proteins from a liquid by binding the immunoglobulins or Fc-containing proteins to an Ig binding protein that is immobilized to a matrix. Thereby, all other components of the mixture except immunoglobulins or Fc-containing proteins are removed. In a further step, the bound immunoglobulins or Fc-containing proteins can be eluted in purified form.

The term "alkaline stable" or "alkaline stability" or "caustic stable" or "caustic stability" refers to the ability of the Ig binding protein of the invention to withstand alkaline conditions without significantly losing the ability to bind to immunoglobulins. The skilled person in this field can easily test alkaline stability by incubating an Ig binding protein with sodium hydroxide, e.g. as described in the Examples, and subsequent testing of the binding activity to immunoglobulin by routine experiments known to someone skilled in the art, for example, by chromatographic approaches.

In some embodiments, Ig binding proteins of the invention as well as matrices comprising Ig binding proteins of the invention exhibit an "increased" or "improved" alkaline stability, meaning that the molecules and matrices incorporating said Ig binding proteins are stable under alkaline conditions for an extended period of time relative to naturally occurring Protein A domains, i.e. do not lose the ability to bind to immunoglobulins or lose the ability to bind to immunoglobulins to a lesser extent than naturally occurring Protein A domains.

The terms "binding activity" or "binding capacity" or "static binding capacity" as used interchangeably herein, refer to the ability of an Ig binding protein of the invention to bind to immunoglobulin. For example, the binding activity can be determined before and/or after alkaline treatment. The binding activity can be determined for an Ig binding protein or for an Ig binding protein coupled to a matrix, i.e. for an immobilized binding protein.

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); Current Protocols in Molecular Biology (F. M. Ausubel et al. Eds., Wiley & Sons); Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al., Eds., Wiley & Sons). Known techniques relating to cell culture and media are described in "Large Scale Mammalian Cell Culture (D. Hu et al., Curr. Opin. Biotechnol. 8:148-153, 1997); "Serum free Media" (K. Kitano, Biotechnol. 17:73-106, 1991); and "Suspension Culture of Mammalian Cells" (J. R. Birch et al. Bioprocess Technol. 10:251-270, 1990).

Embodiments of the Invention

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention is directed to a non-natural immunoglobulin (Ig) binding protein comprising one or more non-natural Ig-binding domains, wherein at least one Ig binding domain comprises or essentially consists or consists of the amino acid sequence $X_1X_2X_3X_4X_5X_6X_7X_8QQX_{11}AFYX_{15}X_{16}LX_{18}X_{19}PX_{21}LX_{23}X_{24}X_{25}QRX_{28}X_{29}FIQSLKDDPSX_{40}SX_{42}X_{43}X_{46}EAX_{49}KLX_{52}X_{53}X_{54}QX_{56}PX_{58}$ (SEQ ID NO: 1), wherein $X_1$ is A, V, Q, N, or P; preferably N, V, P, or A; $X_2$ is D, A, or Q; preferably D or A; $X_3$ is A, S, or N; $X_4$ is K, Q, or N; preferably K or Q; $X_5$ is H or F; $X_6$ is D, N, S, or A; preferably D, S, or A; $X_7$ is E or K; $X_8$ is D, E or A; $X_{11}$ is S or N; $X_{15}$ is E, D, or Q; preferably E; $X_{16}$ is V or I; preferably I; $X_{18}$ is H or N; preferably H; $X_{19}$ is L or M; preferably L; $X_{21}$ is N, S, or D; $X_{23}$ is T or N; preferably T; $X_{24}$ is E or A; preferably E; $X_{25}$ is D or E; $X_{28}$ is N, S, or A; $X_{29}$ is G or A; preferably A; $X_{40}$ is V or Q or T; $X_{42}$ is K, T, or A; preferably K or A; $X_{43}$ is E, N, or S; preferably E or S; $X_{44}$ is V, L, or I; $X_{46}$ is G or A; $X_{49}$ is K or Q; $X_{52}$ is N, S, or D; $X_{53}$ is D or E; $X_{54}$ is S or A; $X_{56}$ is A or P; preferably A; and $X_{58}$ is K or P;

and wherein the dissociation constant $K_D$ of said non-natural Ig-binding protein to human IgG1 is 1 µM or less, preferably 500 nM, more preferably 100 nM or less. In more detail, SEQ ID NO: 1 and a preferred embodiment as shown in SEQ ID NO: 38 are generic sequences resulting from an alignment of SEQ ID NOs: 9 to 30. Thus, each non-natural Ig binding domain of the Ig binding protein of the invention exhibits about 50% to about 85% sequence identity to a naturally occurring Ig binding domain, see Table 1 (see Example 1). Each non-natural Ig binding domain of the Ig binding protein of the invention has the same amino acids in positions that correspond to positions Q9, A12, F13, L17, Q26, R27, F30, I31, L34, P38, S41, L45, A48, L51, Q55 of a naturally occurring Ig binding domain, more preferably with the same amino acids that correspond to positions Q9, Q10, A12, F13, Y14, L17, P20, L22, Q26, R27, F30, I31, Q32, S33, L34, K35, D36, D37, P38, S39, S41, L45, E47, A48, K50, L51, Q55, P57 of a naturally occurring Ig binding domain, for example domain C, domain B, domain A, domain E, and domain D.

In a preferred embodiment of the first aspect, at least one non-natural Ig-binding domain comprises or essentially consists of the amino acid sequence $X_1X_2X_3X_4X_5X_6X_7X_8QQX_{11}AFYEILHLPX_{21}LTEX_{25}QRX_{28}AFIQSLKDDPSX_{40}SX_{42}X_{43}X_{44}LX_{46}EAX_{49}KLX_{52}X_{53}X_{54}QAPX_{58}$ (SEQ ID NO: 38), wherein
$X_1$ is N, V, P, or A;
$X_2$ is D or A;
$X_3$ is A, S, or N;
$X_4$ is K or Q;
$X_5$ is H or F;
$X_6$ is D, S, or A;
$X_7$ is E or K;
$X_8$ is D, E or A;
$X_{11}$ is S or N;
$X_{21}$ is N, S, or D;
$X_{25}$ is D or E;
$X_{28}$ is N, S, or A;
$X_{40}$ is V, T, or Q;
$X_{42}$ is K or A;
$X_{43}$ is E or S;
$X_{44}$ is V, L, or I;
$X_{46}$ is G or A;
$X_{49}$ is K or Q;
$X_{52}$ is N, S, or D;
$X_{53}$ is D or E;
$X_{54}$ is S or A; and
$X_{58}$ is K or P.

SEQ ID NO: 38 is a generic amino acid sequence resulting from an alignment of SEQ ID NOs: 9-30 and is a preferred selection of SEQ ID NO: 1.

In one preferred embodiment of the first aspect, at least one non-natural Ig-binding domain comprises or essentially consists of the amino acid sequence $X_1X_2X_3X_4X_5X_6X_7X_8QQX_{11}AFYX_{15}X_{16}LX_{18}X_{19}PX_{21}LX_{23}X_{24}X_{25}QRX_{28}X_{29}FIQSLKDDPSX_{40}SX_{42}X_{43}X_{44}LX_{46}EAX_{49}KLX_{52}X_{53}X_{54}QX_{56}PX_{58}$ (SEQ ID NO: 2), wherein
$X_1$ is A, V, Q, N, or P; $X_2$ is D, A, or Q; $X_3$ is A or N; $X_4$ is K, Q, or N; $X_5$ is H or F; $X_6$ is D, N, or A; $X_7$ is E or K; $X_8$ is D, E or A; $X_{11}$ is S or N; $X_{15}$ is E or D; $X_{16}$ is V or I; $X_{18}$ is H or N; $X_{19}$ is L or M; $X_{21}$ is N, S, or D; $X_{23}$ is T or N; $X_{24}$ is E or A; $X_{25}$ is D or E; $X_{28}$ is N, S, or A; $X_{29}$ is G or A; $X_{40}$ is V or Q; $X_{42}$ is K, T, or A; $X_{43}$ is E or N; $X_{44}$ is V, L, or I; $X_{46}$ is G or A; $X_{49}$ is K or Q; $X_{52}$ is N or D; $X_{53}$ is D or E; $X_{54}$ is S or A; $X_{56}$ is A or P; and $X_{58}$ is K or P.

In one embodiment of the first aspect, an Ig binding protein according to the invention comprises one or more non-natural Ig binding domains wherein at least one Ig binding domain comprises or essentially consists of the amino acid sequence $X_1X_2AX_4X_5DX_7X_8QQX_{11}AFYEILHLPNLTEX_{25}QRNAFIQSLKDDPSX_{40}SX_{42}X_{43}X_{44}LX_{46}EAX_{49}KLNX_{53}X_{54}QAPK$ (SEQ ID NO: 48), wherein
$X_1$ is N or V;
$X_2$ is D or A;
$X_4$ is K or Q;
$X_5$ is H or F;
$X_7$ is E or K;
$X_8$ is D, E or A;
$X_{11}$ is S or N;
$X_{25}$ is D or E;
$X_{40}$ is V or Q;
$X_{42}$ is K or A;
$X_{43}$ is E or S;
$X_{44}$ is V or I;
$X_{46}$ is G or A;

X$_{49}$ is K or Q;
X$_{53}$ is D or E; and
X$_{54}$ is S or A.

SEQ ID NO: 48 is a generic amino acid sequence resulting from an alignment of SEQ ID NOs: 24, 26, 27, 28, and 30 and is a preferred selection of SEQ ID NO: 38. Ig binding proteins are stable even after alkaline treatment for a prolonged period of time (e.g. at least up to 6 hours, 0.5 M NaOH), for example, Ig binding proteins of the invention have a higher alkaline stability than naturally occurring Protein A domains.

In another embodiment of the first aspect, an Ig binding protein according to the invention comprises one or more non-natural Ig binding domains wherein at least one Ig binding domain comprises or essentially consists of the amino acid sequence X$_1$X$_2$X$_3$X$_4$X$_5$X$_6$X$_7$X$_8$QQX$_{11}$AFYEILHLPX$_{21}$LTEDQRX$_{28}$AFIQSLKDDPSX$_{40}$SKX$_{43}$X$_{44}$LGEAKKLX$_{52}$DAQAPP (SEQ ID NO: 49), wherein
X$_1$ is P, N, or A;
X$_2$ is A or D;
X$_3$ is A, S, or N;
X$_4$ is K or Q;
X$_5$ is H or F;
X$_6$ is D, S, or A;
X$_7$ is K or E;
X$_8$ is D, E or A;
X$_{11}$ is S or N;
X$_{21}$ is N, S, or D;
X$_{28}$ is S or A;
X$_{40}$ is V or T;
X$_{43}$ is E or S;
X$_{44}$ is I or L; and
X$_{52}$ is N, S, or D.

SEQ ID NO: 49 is a generic amino acid sequence resulting from an alignment of SEQ ID NOs: 9 to 23 and is a preferred selection of SEQ ID NO: 38.

In an embodiment of the first aspect, the non-natural Ig-binding protein comprises one or more Ig-binding domains, wherein at least one non-natural Ig-binding domain comprises or consists of an amino acid sequence selected from the group consisting of:

(SEQ ID NO: 9)
NAAQHAKEQQNAFYEILHLPNLTEDQRAAFIQSLKDDPSVSKEILGEAKK
LNDAQAPP, (SEQ ID NO: 10)
NAAQHDKEQQNAFYEILHLPNLTEDQRAAFIQSLKDDPSVSKEILGEAKK
LNDAQAPP, (SEQ ID NO: 11)
NAAQHSKEQQNAFYEILHLPNLTEDQRSAFIQSLKDDPSVSKEILGEAKK
LNDAQAPP, (SEQ ID NO: 12)
NAAQHSKDQQSAFYEILHLPNLTEDQRSAFIQSLKDDPSVSKEILGEAKK
LNDAQAPP, (SEQ ID NO: 13)
PAAQHDKDQQSAFYEILHLPNLTEDQRSAFIQSLKDDPSVSKEILGEAKK
LNDAQAPP, (SEQ ID NO: 14)
PAAKHDKDQQSAFYEILHLPNLTEDQRSAFIQSLKDDPSVSKEILGEAKK
LNDAQAPP, (SEQ ID NO: 15)
ADNKFDEAQQSAFYEILHLPNLTEDQRAAFIQSLKDDPSVSKEILGEAKK
LNDAQAPP, (SEQ ID NO: 16)
ADSKFDEAQQSAFYEILHLPNLTEDQRAAFIQSLKDDPSVSKEILGEAKK
LNDAQAPP, (SEQ ID NO: 17)
ADSKFDEAQQSAFYEILHLPNLTEDQRAAFIQSLKDDPSVSKSLLGEAKK
LNDAQAPP, (SEQ ID NO: 18)
ADSKFDEAQQSAFYEILHLPDLTEDQRAAFIQSLKDDPSVSKSLLGEAKK
LNDAQAPP, (SEQ ID NO: 19)
ADSKFDEAQQSAFYEILHLPSLTEDQRAAFIQSLKDDPSVSKSLLGEAKK
LNDAQAPP, (SEQ ID NO: 20)
ADSKFDEAQQSAFYEILHLPSLTEDQRAAFIQSLKDDPSTSKSLLGEAKK
LNDAQAPP, (SEQ ID NO: 21)
ADSKFDEAQQSAFYEILHLPSLTEDQRAAFIQSLKDDPSTSKSLLGEAKK
LDDAQAPP, (SEQ ID NO: 22)
ADSKFDEAQQSAFYEILHLPSLTEDQRAAFIQSLKDDPSTSKSLLGEAKK
LSDAQAPP, (SEQ ID NO: 23)
PAAKHDKDQQSAFYEILHLPSLTEDQRAAFIQSLKDDPSTSKSILGEAKK
LNDAQAPP, (SEQ ID NO: 24)
NAAQHDKEQQNAFYEILHLPNLTEDQRNAFIQSLKDDPSVSKEILGEAKK
LNDAQAPK, (SEQ ID NO: 25)
ADNKFDEAQQSAFYEILHLPNLTEDQRNAFIQSLKDDPSVSKEILGEAKK
LNDAQAPK, (SEQ ID NO: 26)
NAAKHDKDQQSAFYEILHLPNLTEDQRNAFIQSLKDDPSVSKEILGEAKK
LNDAQAPP, (SEQ ID NO: 27)
NAAQHDKDQQSAFYEILHLPNLTEEQRNAFIQSLKDDPSVSKEILAEAKK
LNDAQAPK, (SEQ ID NO: 28)
NAAKFDEAQQSAFYEILHLPNLTEEQRNAFIQSLKDDPSVSKEVLGEAQK
LNDSQAPK, (SEQ ID NO: 29)
QQAQHDEAQQSAFYQVLHLPNLTADQRNAFIQSLKDDPSQSAEVLGEAQK
LNDSQAPK,
and (SEQ ID NO: 30)
VDAQHDEDQQSAFYEILHLPNLTEEQRNAFIQSLKDDPSQSAEILAEAKK
LNESQAPK.

Particularly preferred are the non-natural Ig-binding proteins that comprise one or more Ig-binding domains, wherein at least one non-natural Ig-binding domain comprises or essentially consists of an amino acid sequence selected from the group consisting of SEQ ID NOs: 13, 14, 23, 26, 27, 28, and 30.

As shown in the examples herein below, the proteins of the invention were found to bind to IgG. In more detail, it was found that the Ig-binding polypeptides comprising the generic sequence of SEQ ID NO: 1, more specifically of the generic sequences of SEQ ID NO: 38 or SEQ ID NO: 2, even more specifically SEQ ID NOs: 9-30, are able to bind to IgG at high affinities that are comparable to binding properties of naturally occurring Ig binding domain (see Table 2, Example 5, and Table 3, Example 6). It was more surprising and unexpected that the Ig-binding proteins comprising the generic sequence of SEQ ID NO: 1, more specifically the generic sequences of SEQ ID NO: 38 or SEQ ID NO: 2, even more specifically SEQ ID NOs: 9-30, are able to bind to IgG even after alkaline treatment for several hours, for example after treatment with 0.5 M NaOH for up to 6 hours. This is an advantageous property as compared to naturally occurring Protein A domains or domain Z (e.g., see comparative data in Example 7 and in Example 8 and in FIG. 8 and FIG. 9).

In one embodiment of the invention, the non-natural Ig-binding protein comprises 1, 2, 3, 4, 5, 6, 7, or 8, preferably 4, 5, or 6, non-naturally-occurring Ig-binding domains linked to each other, i.e. the non-natural Ig-binding protein can be a monomer, dimer, trimer, tetramer, pentamer, hexamer, etc. For example, SEQ ID NO: 14 was used to generate the multimeric fusion constructs described herein in Example 1. The obtained Ig binding proteins comprising more than one Ig binding domain are stable and display Ig binding properties even after alkaline treatment (for example, see FIG. 10). Selected but non-limiting examples for multimeric Ig binding proteins are provided in SEQ ID NO: 45 (dimer), SEQ ID NO: 46 (tetramer), or SEQ ID NO: 47 (hexamer).

In some embodiments of the first aspect, the non-natural Ig-binding domains are directly linked to each other. In other embodiments of the first aspect, the non-natural Ig-binding domains are linked to each other via peptide linkers. In some embodiments of the first aspect, the amino acid sequences of all non-natural Ig-binding domains of the Ig binding protein are identical (for example, SEQ ID NOs: 45-47). In other embodiments of the first aspect, at least one non-natural Ig-binding domain has a different amino acid sequence than the other Ig-binding domains within the non-natural immunoglobulin-binding protein.

The dissociation constant $K_D$ of Ig binding proteins or domains can be determined as described above and in the Examples (e.g. see Example 5 and Example 6). Typically, the dissociation constant $K_D$ is determined at 20° C., 25° C. or 30° C. If not specifically indicated otherwise, the $K_D$ values recited herein are determined at 25° C.+/−3° C. by surface plasmon resonance. In an embodiment of the first aspect, the non-natural Ig-binding protein has a dissociation constant $K_D$ to human $IgG_1$ in the range between 0.1 nM and 1000 nM, preferably between 0.1 nM and 500 nM, more preferably between 0.1 nM and 100 nM, more preferably between 0.5 nM and 100 nM, more preferably between 1 nM and 10 nM.

In an embodiment of the first aspect, the non-natural Ig-binding protein has a dissociation constant $K_D$ to human $IgG_2$ in the range between 0.1 nM and 1000 nM, preferably between 0.1 nM and 500 nM, more preferably between 0.1 nM and 100 nM, more preferably between 0.5 nM and 100 nM, more preferably between 1 nM and 10 nM In an embodiment of the first aspect, the non-natural Ig-binding protein has a dissociation constant $K_D$ to human $IgG_4$ in the range between 0.1 nM and 1000 nM, preferably between 0.1 nM and 500 nM, more preferably between 0.1 nM and 100 nM, more preferably between 0.5 nM and 100 nM, more preferably between 1 nM and 10 nM.

In a second aspect the present invention is directed to a composition comprising the non-natural Ig-binding protein of the first aspect.

In preferred embodiments of the second aspect, the composition is an affinity separation matrix, which comprises the non-natural Ig-binding protein according to any of the embodiments described above coupled to a solid support. The affinity separation matrix comprises a plurality of Ig binding proteins of the invention coupled to a solid support.

This matrix comprising the non-natural Ig binding protein of the invention is useful for separation, for example for chromatographic separation, of immunoglobulins and other Fc-containing proteins, such as immunoglobulin derivatives comprising the Fc region, fusion proteins comprising an Fc region of an immunoglobulin, and conjugates comprising an Fc region of an immunoglobulin. Solid support matrices for affinity chromatography are known in the art and include for example but are not limited to, agarose and stabilized derivatives of agarose (e.g. rPROTEIN A Sepaharose Fast Flow or Mabselect®), controlled pore glass (e.g. ProSep® vA resin), monolith (e.g. CIM® monoliths), silica, zirconium oxide (e.g. CM Zirconia or CPG®), titanium oxide, or synthetic polymers (e.g. polystyrene such as Poros 50A or Poros MabCapture® A resin, polyvinylether, polyvinyl alcohol, polyhydroxyalkyl acrylates, polyhydroxyalkyl methacrylates, polyacrylamides, polymethacrylamides etc) and hydrogels of various compositions. In certain embodiments the support comprises a polyhydroxy polymer, such as a polysaccharide.

Examples of polysaccharides suitable for supports include but are not limited to dextran, starch, cellulose, pullulan, agar, agarose, etc, and stabilized variants of these.

The solid support formats can be of any suitable well-known kind. Such a solid support for coupling the Ig binding protein of the invention might comprise for example but is not limited to one of the following: columns, capillaries, particles, membranes, filters, monoliths, fibers, pads, gels, slides, plates, cassettes, or any other format commonly used in chromatography and known to someone skilled in the art. In one embodiment of the matrix, the carrier is comprised of substantially spherical particles, also known as beads, for example Sepharose or Agarose beads. Suitable particle sizes may be in the diameter range of 5-500 μm, such as 10-100 μm, e.g. 20-80 μm. In an alternative embodiment, the carrier is a membrane, for example a hydrogel membrane. In some embodiments, the affinity purification involves a membrane as matrix to which the non-natural Ig-binding protein of the first aspect is covalently bound.

The solid support can also be in the form of a membrane in a cartridge. In one embodiment, the solid matrix is in beaded or particle form that can be porous or non-porous. Matrices in beaded or particle form can be used as a packed bed or in a suspended form including expanded beds. In case of monoliths, packed bed and expanded beds, the separation procedure commonly follows conventional chromatography with a concentration gradient or concentration steps in the mobile phase. In case of pure suspension, batch-wise mode will be used.

In some embodiments, the affinity purification involves a chromatography column containing a solid support to which the non-natural Ig-binding protein of the first aspect is covalently bound.

The Ig binding protein of the invention may be attached to a suitable solid support via conventional coupling techniques utilising, e.g. amino-, sulfhydroxy-, and/or carboxy-groups present in the Ig binding protein of the invention. The coupling may be carried out via a nitrogen, oxygen, or sulphur atom of the Ig binding protein. Preferably, amino acids comprised in an N- or C-terminal peptide linker comprise said nitrogen, oxygen or sulphur atom. The Ig binding proteins may be coupled to the carrier directly or indirectly via a spacer element to provide an appropriate distance between the carrier surface and the Ig binding protein of the invention which improves the availability of the Ig binding protein and facilitates the chemical coupling of the Ig binding protein of the invention to the support.

Methods for immobilisation of protein ligands to solid supports are well-known in this field and easily performed by the skilled person in this field using standard techniques and equipment.

In one embodiment, the non-natural Ig-binding protein comprises an attachment site for covalent attachment to a solid phase (matrix). Preferably, the attachment site is specific to provide a site-specific attachment to the solid phase. Specific attachment sites comprise natural amino acids, such as cysteine or lysine, or non-natural amino acids which enable specific chemical reactions with a reactive group of the solid phase, for example selected from sulfhydryl, maleimide, epoxy, or alkene groups, or a linker between the solid phase and the protein. The N-terminus can be labelled preferentially at acidic pH with amino-reactive reagents. Preferred embodiments of the invention comprise a short N- or C-terminal peptide sequence of 5-20 amino acids, preferably 10 amino acids, with a terminal cysteine. Amino acids for the C-terminal peptide sequence are preferably selected from proline, alanine, serine, for example, ASPAPSAPSAC (SEQ ID NO: 39).

In a third aspect the present invention is directed to the use of the non-natural Ig-binding protein of the first aspect or a composition of the second aspect for affinity purification of immunoglobulins, i.e. the Ig-binding protein of the invention is used for affinity chromatography. In some embodiments, the Ig-binding protein of the invention is immobilized onto a solid support as described in the second aspect of the invention. In one embodiment of the third aspect, the immunoglobulin to be purified is selected from the group consisting of human IgG1, human IgG2, human IgG4, human IgM, human IgA, mouse IgG1, mouse IgG2A, mouse IgG2B, mouse IgG3, rat IgG1, rat IgG2C, goat IgG1, goat IgG2, bovine IgG2, guinea pig IgG, rabbit IgG, immunoglobulin fragments comprising the Fc region, fusion proteins comprising an Fc region of an immunoglobulin, and conjugates comprising an Fc region of an immunoglobulin.

In a fourth aspect the present invention is directed to a method of affinity purification of immunoglobulins comprising the steps of (a) providing a liquid containing an immunoglobulin; (b) providing an affinity separation matrix comprising an immobilized non-natural Ig-binding protein of the first aspect; (c) contacting said liquid and said affinity separation matrix, wherein said immunoglobulin binds to said immobilized non-natural Ig-binding protein; and (d) eluting said immunoglobulin from said matrix, thereby obtaining an eluate containing said immunoglobulin; and (e) optionally further comprising one or more washing steps carried out between steps (c) and (d). Affinity separation matrixes are according to the embodiments described above and as known to someone skilled in the art.

In some embodiments of the fourth aspect, the isolation of the immunoglobulin from the matrix in step (d) is effected through a change in pH or a change in salt concentration. In some embodiments of the fourth aspect, the method comprises the further step (f) recovering said eluate.

In one embodiment of the fourth aspect, the immunoglobulin is selected from the group consisting of human IgG1, human IgG2, human IgG4, human IgM, human IgA, mouse IgG1, mouse IgG2A, mouse IgG2B, mouse IgG3, rat IgG1, rat IgG2C, goat IgG1, goat IgG2, bovine IgG2, guinea pig IgG, rabbit IgG, immunoglobulin fragments comprising the Fc region, fusion proteins comprising an Fc region of an immunoglobulin, and conjugates comprising an Fc region of an immunoglobulin.

In a fifth aspect the present invention is directed to a method of generation of a non-natural Ig-binding protein comprising at least one Ig-binding domain according to the first aspect, wherein the amino acid sequence of an Ig-binding domain is obtained by a shuffling process of amino acid sequences of at least two naturally occurring Protein A domains from naturally occurring Protein A. In more detail, the shuffling process as understood herein is an assembly process resulting in novel and artificial amino acid sequences starting from a set of non-identical known amino acid sequences comprising the following steps: (a) providing a set of sequences to be shuffled, for example sequences of five naturally occurring protein A domains E, D, A, B, and C and protein A derivatives (e.g. Z domain or other domains with at least 90% identity to any naturally occurring domain); (b) alignment of said sequences; (c) statistical fragmentation in silico, and then (d) in silico assembly of new sequences from the various fragments to produce a mosaic product maintaining the relative order. The fragments generated in step c) can be of any length, e.g. if the fragmented parent sequence has a length of n the fragments can be of length 1 to n−1. Thus, the reassembled protein is made up from a series of fragments comprising subsequences of one or more amino acids such that these subsequences are present at the corresponding positions in one or more of the individual IgG-binding domains from protein A that have been aligned in step (b). In other words, at every amino acid position of the assembled mosaic sequence, there is at least one protein amongst the aligned IgG-binding domains from protein A that comprises the same amino acid at the corresponding position. However, the overall amino acid sequence of the reassembled protein is artificial in that it is not identical to the overall amino acid sequence of any of the IgG-binding domains from protein A. The amino acid at each position of the new sequence corresponds to the same position of any of the aligned sequences. The relative positions of the amino acids in the mosaic products are maintained with respect to the starting sequences. The general shuffling process for the generation of novel, artificial IgG-binding proteins is depicted in FIG. 1A.

After this initial shuffled protein is produced, the protein can optionally be further modified by site-specific randomization of the amino acid sequence to further modify the binding properties of the shuffled protein, if desired. By way of example, the further modifications can be introduced by site-saturation mutagenesis of individual amino acid residues to produce a plurality of modified shuffled polypeptides. These IgG-binding proteins can then be screened to identify those modified shuffled polypeptides that have whatever binding properties might be of interest.

Therefore, the generation of IgG binding proteins of the invention involves one or two basic steps: a first step in which related sequences are aligned and shuffled to produce a shuffled polypeptide, and if desired, a second step to further modify the binding activity of the shuffled protein.

The Ig binding protein of the invention comprises one or more non-natural Ig-binding domains, wherein each non-natural Ig binding domain has identical amino acids as naturally occurring protein A domains A, B, C, D, or E or domain Z in positions that correspond to positions Q9, A12, F13, L17, Q26, R27, F30, I31, L34, P38, S41, L45, A48, L51, Q55, more preferably with the same amino acids that correspond to positions Q9, Q10, A12, F13, Y14, L17, P20, L22, Q26, R27, F30, I31, Q32, S33, L34, K35, D36, D37, P38, S39, S41, L45, E47, A48, K50, L51, Q55, P57 of a naturally occurring Ig binding domain.

Sequence identity of Ig binding proteins of the invention to naturally occurring protein A domains A, B, C, D, or E or domain Z is at most about 85% (see Table 1 for more detail).

In a sixth aspect the present invention is directed to a nucleic acid molecule, preferably an isolated nucleic acid molecule, encoding a non-natural Ig-binding protein of the first aspect.

The present invention also encompasses polypeptides encoded by the nucleic acid molecules of the sixth aspect of the invention.

In a seventh aspect the present invention is directed to a vector comprising the nucleic acid molecule of the sixth aspect.

A vector means any molecule or entity (e.g., nucleic acid, plasmid, bacteriophage or virus) that can be used to transfer protein coding information into a host cell.

In one embodiment of the seventh aspect, the vector is an expression vector.

In an eighth aspect the present invention is directed to a host cell, preferably an isolated host cell, or a non-human host comprising the non-natural Ig-binding protein of the first aspect, a nucleic acid molecule of the sixth aspect, or a vector of the seventh aspect.

For example, one or more nucleic acid molecules which encode an Ig-binding protein of the invention may be expressed in a suitable host and the produced binding protein can be isolated.

A host cell is a cell that has been transformed, or is capable of being transformed, with a nucleic acid sequence and thereby expresses a gene of interest.

Suitable host cells include prokaryotes or eukaryotes. Various mammalian or insect cell culture systems can also be employed to express recombinant proteins. In accordance with the present invention, the host may be a transgenic non-human animal transfected with and/or expressing the proteins of the present invention. In a preferred embodiment, the transgenic animal is a non-human mammal.

In a ninth aspect the present invention is directed to a method for the production of a non-natural Ig-binding protein of the first aspect, comprising the step(s): (a) culturing the host cell of the seventh aspect under suitable conditions for the expression of the binding protein in order to obtain said non-natural Ig-binding protein; and (b) optionally isolating said non-natural Ig-binding protein.

The invention also encompasses a non-natural Ig-binding protein produced by the method of the ninth aspect. Suitable conditions for culturing a prokaryotic or eukaryotic host are well-known to the person skilled in the art. Ig-binding molecules of the invention may be prepared by any of the many conventional and well-known techniques such as plain organic synthetic strategies, solid phase-assisted synthesis techniques or by commercially available automated synthesizers. On the other hand, they may also be prepared by conventional recombinant techniques alone or in combination with conventional synthetic techniques. Conjugates according to the present invention may be obtained by combining compounds as known to someone skilled in the art, for example by chemical methods, e.g. lysine or cysteine-based chemistry, or by conventional recombinant techniques. The term "conjugate" as used herein relates to a molecule comprising or essentially consisting of at least a first protein attached chemically to other substances such as to a second protein or a non-proteinaceous moiety.

One embodiment of the present invention is directed to a method for the preparation of an Ig-binding protein according to the invention as detailed above, said method comprising the following steps: (a) preparing a nucleic acid encoding a binding protein as defined above; (b) introducing said nucleic acid into an expression vector; (c) introducing said expression vector into a host cell; (d) cultivating the host cell; (e) subjecting the host cell to culturing conditions under which a an Ig-binding protein is expressed, thereby (e) producing a binding protein as described above; optionally (f) isolating the protein produced in step (e); and (g) optionally conjugating the protein to solid matrices as described above.

In a further embodiment of the present invention the production of the non-natural Ig binding protein is performed by cell-free in vitro transcription/translation.

EXAMPLES

The following Examples are provided for further illustration of the invention. The invention, however, is not limited thereto, and the following Examples merely show the practicability of the invention on the basis of the above description. For a complete disclosure of the invention reference is made also to the literature cited in the application which is incorporated completely into the application by reference.

Example 1. Generation of IgG Binding Proteins of the Invention by a Shuffling Process The IgG binding proteins of the invention were initially generated by a shuffling process of naturally occurring Protein A domains and protein A derivatives (e.g. Z domain or other domains with at least 90% identity to any naturally occurring domain). The shuffling process comprised the following steps: a) providing sequences of five naturally occurring protein A domains E, B, D, A, and C, and protein A derivative domain Z; b) alignment of said sequences; c) statistical fragmentation in silico to identify subsequences that can be recombined with the proviso that positions Q9, Q10, A12, F13, Y14, L17, P20, L22, Q26, R27, F30, I31, Q32, S33, L34, K35, D36, D37, P38, S39, S41, L45, E47, A48, K50, L51, Q55, P57 of a naturally occurring Ig binding domain are maintained, and then d) assembly of new, artificial sequences of the various fragments to produce a mosaic product, i.e. a novel amino acid sequence.

The relative positions of the amino acids in the mosaic products were maintained with respect to the starting sequences. At least positions Q9, Q10, A12, F13, Y14, L17, P20, L22, Q26, R27, F30, I31, Q32, S33, L34, K35, D36, D37, P38, S39, S41, L45, E47, A48, K50, L51, Q55, P57 are identical between the "shuffled" sequences and all naturally occurring Protein A domains. The overall amino acid sequence of the reassembled, "shuffled" protein is artificial in that it is not more than 85% identical to the overall amino acid sequence of any of the naturally occurring Protein A domains or domain Z. For example, identities of Ig binding proteins compared to naturally occurring Protein A domains or domain Z are shown in Table 1.

TABLE 1

| | Identities of IgG binding proteins to naturally occurring Protein A domains. | | | | | |
|---|---|---|---|---|---|---|
| | E | D | A | B | C | Z |
| 9 | 69% | 64% | 66% | 72% | 81% | 74% |
| 10 | 71% | 64% | 66% | 72% | 81% | 74% |
| 11 | 69% | 64% | 66% | 72% | 81% | 74% |
| 12 | 67% | 67% | 62% | 69% | 78% | 71% |
| 13 | 67% | 67% | 62% | 69% | 78% | 71% |
| 14 | 66% | 69% | 62% | 71% | 79% | 72% |
| 15 | 62% | 69% | 67% | 76% | 84% | 76% |
| 16 | 62% | 67% | 66% | 74% | 83% | 74% |
| 17 | 62% | 67% | 67% | 76% | 79% | 76% |

TABLE 1-continued

Identities of IgG binding proteins to naturally occurring Protein A domains.

| | E | D | A | B | C | Z |
|---|---|---|---|---|---|---|
| 18 | 60% | 66% | 66% | 74% | 78% | 74% |
| 19 | 60% | 66% | 66% | 74% | 78% | 74% |
| 20 | 60% | 66% | 66% | 74% | 76% | 74% |
| 21 | 59% | 64% | 64% | 72% | 74% | 72% |
| 22 | 60% | 64% | 64% | 72% | 74% | 72% |
| 23 | 64% | 67% | 60% | 69% | 74% | 71% |
| 24 | 72% | 69% | 71% | 78% | 86% | 79% |
| 25 | 69% | 71% | 67% | 76% | 84% | 78% |
| 26 | 69% | 71% | 69% | 76% | 84% | 78% |
| 27 | 76% | 74% | 67% | 72% | 79% | 74% |
| 28 | 71% | 74% | 76% | 76% | 78% | 79% |

"E, D, A, B, C, Z" refers to naturally occurring Protein A domains and to domain Z (SEQ ID NOs: 3-8). The numbers "9-30" refer to examples for Ig binding proteins of the invention. For example, the numbers "9-24" refer to corresponding SEQ ID NOs: 9-24, "25" refers to SEQ ID NO: 26, "26" refers to SEQ ID NO: 27, "27" refers to SEQ ID NO: 28, and "28" refers to SEQ ID NO: 30.

Genes for the "shuffled" IgG binding proteins as well as naturally occurring Protein A domains and derivatives (e.g. domain C, domain B, domain A, domain D, domain, domain Z) were synthesized and cloned into an *E. coli* start-expression vector using standard methods known to a skilled person. DNA sequencing was used to verify the correct sequence of inserted fragments.

To generate Ig binding proteins comprising more than one binding domain, 2, 4, or 6 identical IgG binding domains (SEQ ID NO: 14) were genetically fused via amino acid linkers (SEQ ID NO: 41 and SEQ ID NO: 42). The amino acid sequences of the fusion proteins are shown in SEQ ID NO: 45-47.

For specific membrane attachment and purification, a short peptide linker with C-terminal Cys (ASPAPSAPSAC; SEQ ID NO: 39) and a strep-tag (WSHPQFEK; SEQ ID NO: 44) were added to the C-terminus of the Ig binding proteins (for example, see SEQ ID NO: 50 and SEQ ID NO: 51).

Example 2. Expression of IgG Binding Proteins

HMS174 (DE3) competent cells were transformed with either expression plasmid encoding IgG binding proteins. Cells were spread onto selective agar plates (Kanamycin) and incubated overnight at 37° C. Precultures were inoculated from single colony in 100 ml superrich medium (modified H15 medium 2% Glucose, 5% Yeast extract, 1% Casamino acids, 0.76% Glycerol, 1% Torula Yeast RNA, 250 mM MOPS, 202 mM TRIS, 10 mg/L RNase A, pH7.4, Antifoam SE15) and cultured 16 hours at 37° C. at 160 rpm in a conventional orbital shaker in baffled 1 L Erlenmeyer flasks supplemented with 150 µg/ml Kanamycin without lactose and antifoam. The $OD_{600}$ readout should be in the range of 6-12. Main culture was inoculated from previous overnight culture with an adjusted start-$OD_{600}$ of 0.5 in 400 ml superrich medium in 1 L thick-walled Erlenmeyer flasks that was supplemented with glycerol, glucose, lactose, antifoam agent and 150 µg/ml Kanamycin. Cultures were transferred to a resonant acoustic mixer (RAMbio) and incubated at 37° C. with 20×g. Aeration was facilitated by Oxy-Pump stoppers. Recombinant protein expression was induced by metabolizing glucose and subsequently allowing lactose to enter the cells. At predefined time points $OD_{600}$ was measured, samples adjusted to $5/OD_{600}$ were withdrawn, pelleted and frozen at −20° C. Cells were grown overnight for approx. 24 hours to reach a final $OD_{600}$ of about 45-60. To collect biomass cells were centrifuged at 16000×g for 10 min at 20° C. Pellets were weighed (wet weight) and pH was measured in the supernatant. Cells were stored at −20° C. before processing.

Example 3: SDS-PAGE Analysis of Expression and Solubility of IgG Binding Proteins Samples taken during fermentation were resuspended in 300 µl extraction buffer (PBS supplemented with 0.2 mg/ml Lysozyme, 0.5× BugBuster, 7.5 mM $MgSO_4$, 40 U Benzonase) and solubilized by agitation in a thermomixer at 700 rpm, rt for 15 min. Soluble proteins were separated from insoluble proteins by centrifugation (16000×g, 2 min, rt). Supernatant was withdrawn (soluble fraction) and the pellet (insoluble fraction) was resuspended in equivalent amount of urea buffer (8 M urea, 0.2 M Tris, 2 mM EDTA, pH 8.5). From both soluble and insoluble fraction 50 µl were taken and 12 µl 5× sample buffer as well as 5 µl 0.5 M DTT were added. Samples were boiled at 95° C. for 5 min. Finally, 8 µl of those samples were applied to NuPage Novex 4-12% Bis-Tris SDS gels which was run in accordance to the manufacturer's recommendations and stained with Coomassie. High level expression of all IgG binding proteins was found under optimized conditions within the chosen period of time (FIG. 3). All expressed Ig binding proteins were soluble to more than 95% according to SDS-PAGE.

Example 4: Purification of IgG Binding Proteins

All IgG binding proteins were expressed in the soluble fraction of *E. coli* with a C-terminal StrepTagII (WSHPQFEK; SEQ ID NO: 44). The cells were lysed by sonication and the first purification step was performed with Strep-Tactin-columns according to the manufacturer's instructions. To avoid disulfide formation the buffers were supplemented with 1 mM DTT. The eluted fractions were injected to a HiLoad 16/600 Superdex 75 pg (GE Healthcare) equilibrated with 20 mM citrate pH 6.0 and 150 mM NaCl. The peak fractions were pooled and analyzed by SDS-PAGE.

Example 5. The IgG Binding Proteins Bind to IgG with High Affinities (as Determined by ELISA)

The affinities of the IgG binding proteins towards $IgG_1$ or $IgG_2$ or $IgG_4$ were determined using an Enzyme Linked Immunosorbent Assay (ELISA). $IgG_1$ or $IgG_2$ or $IgG_4$ containing antibodies (e.g. Cetuximab for $IgG_1$, Panitumumab for $IgG_2$, or Natalizumab for $IgG_4$) were immobilized on a 96 well Nunc MaxiSorb ELISA plate (2 µg/ml). After incubation for 16 h at 4° C. the wells were washed three times with PBST (PBS+0.1% Tween 20) and the wells were blocked with 3% BSA in PBS (2 h at room temperature). The negative controls were wells blocked only with BSA. After blocking, the wells were washed three times with PBST and incubated for 1 h with the IgG binding protein (in PBST) at room temperature. After incubation the wells were washed three times with PBST and subsequently incubated with Strep-Tactin-HRP (1:10000) from IBA for 1 h at room temperature. Afterwards the wells were washed three times with PBST and three times with PBS. The activity of the horseradish peroxidase was visualized by adding TMB-Plus substrate. After 30 min the reaction was stopped by adding 0.2 M $H_2SO_4$ and the absorbance was measured at 450 nm. Results are shown in Table 2.

TABLE 2

Binding analysis of IgG binding proteins (binding analysis with Cetuximab; CID = clone identification number).

| IgG binding protein | CID | $K_D$ IgG$_1$ (nM) | $K_D$ IgG$_2$ (nM) | $K_D$ IgG$_4$ (nM) |
|---|---|---|---|---|
| Domain E (SEQ ID NO: 3) | 148473 | 13.7 | | |
| Domain D (SEQ ID NO: 4) | 148474 | 4.8 | | |
| Domain A (SEQ ID NO: 5) | 148475 | 4.5 | | |
| Domain B (SEQ ID NO: 6) | 148476 | 3.1 | 6 | 3.5 |
| Domain C (SEQ ID NO: 7) | 148477 | 2.8 | | |
| Domain Z (SEQ ID NO: 8) | 148478 | 3.4 | | |
| SEQ ID NO: 9 | 148458 | 7 | | |
| SEQ ID NO: 10 | 148459 | 7 | | |
| SEQ ID NO: 11 | 148460 | 8.0 | 10.4 | 7.1 |
| SEQ ID NO: 12 | 148461 | 7.8 | | |
| SEQ ID NO: 13 | 148462 | 6.7 | | |
| SEQ ID NO: 14 | 148463 | 4.9 | | |
| SEQ ID NO: 15 | 148464 | 5.4 | | |
| SEQ ID NO: 16 | 148465 | 4.6 | | |
| SEQ ID NO: 17 | 148466 | 5.7 | | |
| SEQ ID NO: 18 | 148467 | 3.9 | | |
| SEQ ID NO: 19 | 148468 | 4.4 | | |
| SEQ ID NO: 20 | 148469 | 6.3 | 9.2 | 5.4 |
| SEQ ID NO: 21 | 148470 | 6.3 | | |
| SEQ ID NO: 22 | 148471 | 4.6 | | |
| SEQ ID NO: 23 | 148472 | 5.9 | | |

Example 6. The IgG Binding Proteins Bind to IgG with High Affinities (as Determined with Surface Plasmon Resonance Experiments)

A CM5 sensor chip (GE Healthcare) was equilibrated with SPR running buffer. Surface-exposed carboxylic groups were activated by passing a mixture of EDC and NHS to yield reactive ester groups. 700-1500 RU on-ligand were immobilized on a flow cell, off-ligand was immobilized on another flow cell. Injection of ethanolamine after ligand immobilization removes non-covalently bound Ig binding protein. Upon ligand binding, protein analyte was accumulated on the surface increasing the refractive index. This change in the refractive index was measured in real time and plotted as response or resonance units (RU) versus time. The analytes were applied to the chip in serial dilutions with a suitable flow rate (µl/min). After each run, the chip surface was regenerated with regeneration buffer and equilibrated with running buffer. The control samples were applied to the matrix.

Regeneration and re-equilibration were performed as previously mentioned. Binding studies were carried out by the use of the Biacore® 3000 (GE Healthcare); data evaluation was operated via the BIAevaluation 3.0 software, provided by the manufacturer, by the use of the Langmuir 1:1 model (RI=0). Evaluated dissociation constants ($K_D$) were standardized against off-target. Results are shown in Table 3.

TABLE 3

Binding analysis of IgG binding proteins (binding analysis with hIgG1-Fc; CID = clone identification number).

| IgG binding protein | CID | $K_D$ IgG$_1$-Fc (nM) |
|---|---|---|
| Domain Z (SEQ ID NO: 8) | 148478 | 2.35 |
| SEQ ID NO: 13 | 148462 | 1.2 |
| SEQ ID NO: 14 | 148463 | 1.3 |
| SEQ ID NO: 24 | 154253 | 1.4 |
| SEQ ID NO: 26 | 154254 | 4.6 |
| SEQ ID NO: 27 | 154255 | 5.3 |
| SEQ ID NO: 28 | 154256 | 3 |
| SEQ ID NO: 30 | 154257 | 7.6 |

TABLE 3-continued

Binding analysis of IgG binding proteins (binding analysis with hIgG1-Fc; CID = clone identification number).

| IgG binding protein | CID | $K_D$ IgG$_1$-Fc (nM) |
|---|---|---|
| SEQ ID NO: 45 (dimer) | 150570 | 0.38 |
| SEQ ID NO: 46 (tetramer) | 150663 | 0.09 |
| SEQ ID NO: 47 (hexamer) | 150772 | 0.16 |

Example 7. Binding of IgG Binding Proteins to a SulfoLink Coupling Resin and Alkaline Stability of Immobilized IgG Binding Proteins The IgG binding proteins were coupled to SulfoLink® coupling resin (Thermo; Cat. No. 20402) according to the manufacturer's instructions. The resin-bed volume of the column was 300 µl. The column was equilibrated with four resin-bed volumes of coupling buffer (50 mM Tris, 5 mM EDTA-Na, pH 8.5). The IgG binding protein was added to the column (1-2 ml/ml SulfoLink coupling resin). The IgG binding proteins were coupled to the matrix via the cysteine at the C-terminus (ASPAPSAPSAC; SEQ ID NO: 39). The column was mixed for 15 minutes, incubated another 30 minutes without mixing and washed with coupling buffer. The system flow was 0.5 ml/min. 300 µl of 50 mM cysteine solution was added to the column, mixed for 15 minutes, incubated another 30 minutes without mixing and washed with 1 M NaCl followed by washing with PBS.

Figure 6A:
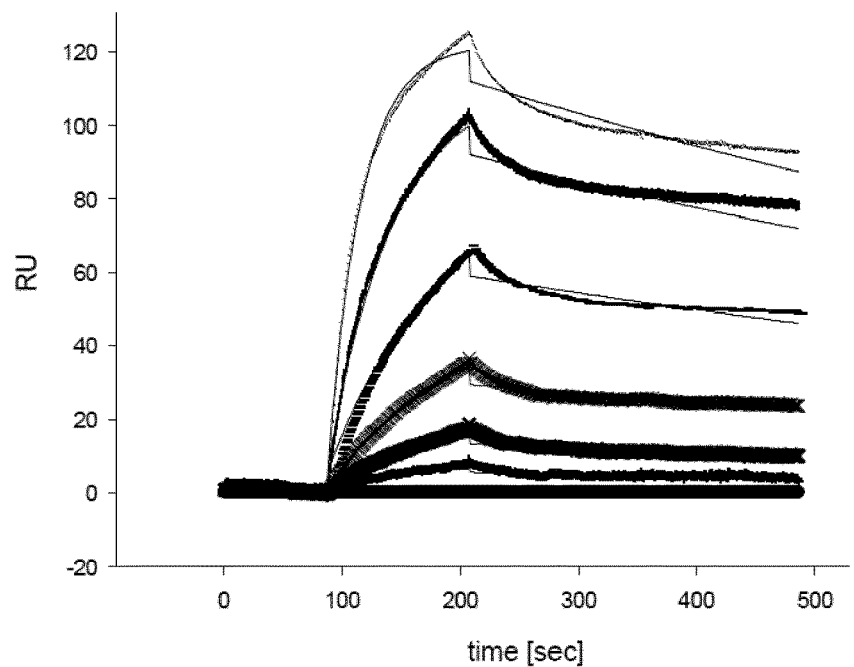
FIG. 6A. Analysis of Ig binding protein 148463 (SEQ ID NO: 14). Concentrations analyzed were 0 nM, 1.56 nM, 3.125 nM, 6.25 nM, 12.5 nM, 25 nM, 50 nM. The $K_D$ for SEQ ID NO: 14 is 1.3 nM, FIG. 6B. Analysis of Ig binding protein 154256 (SEQ ID NO: 28). Concentrations analyzed were 0, 0.39 nM, 0.78 nM, 1.56 nM, 3.125 nM, 6.25 nM, 12.5 nM, 25 nM, 50 nM. The $K_D$ for SEQ ID NO: 28 is 3.1 nM. Further results are shown in Table 3 (see Example 6).
Figure 6B:
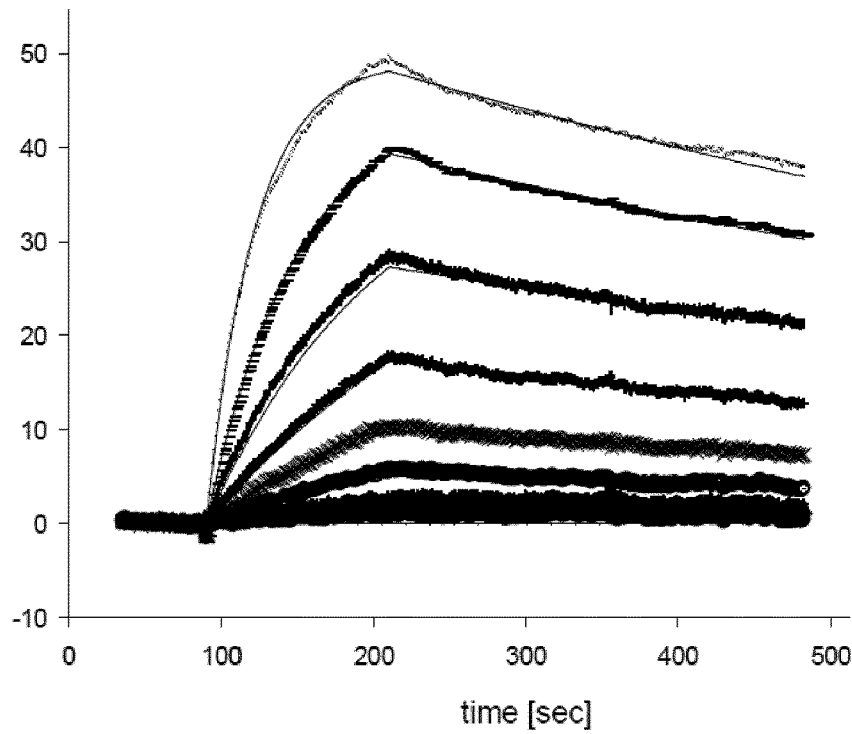
FIG. 6. Analysis of the binding affinity of IgG binding proteins by SPR (Biacore).
Figure 7A:
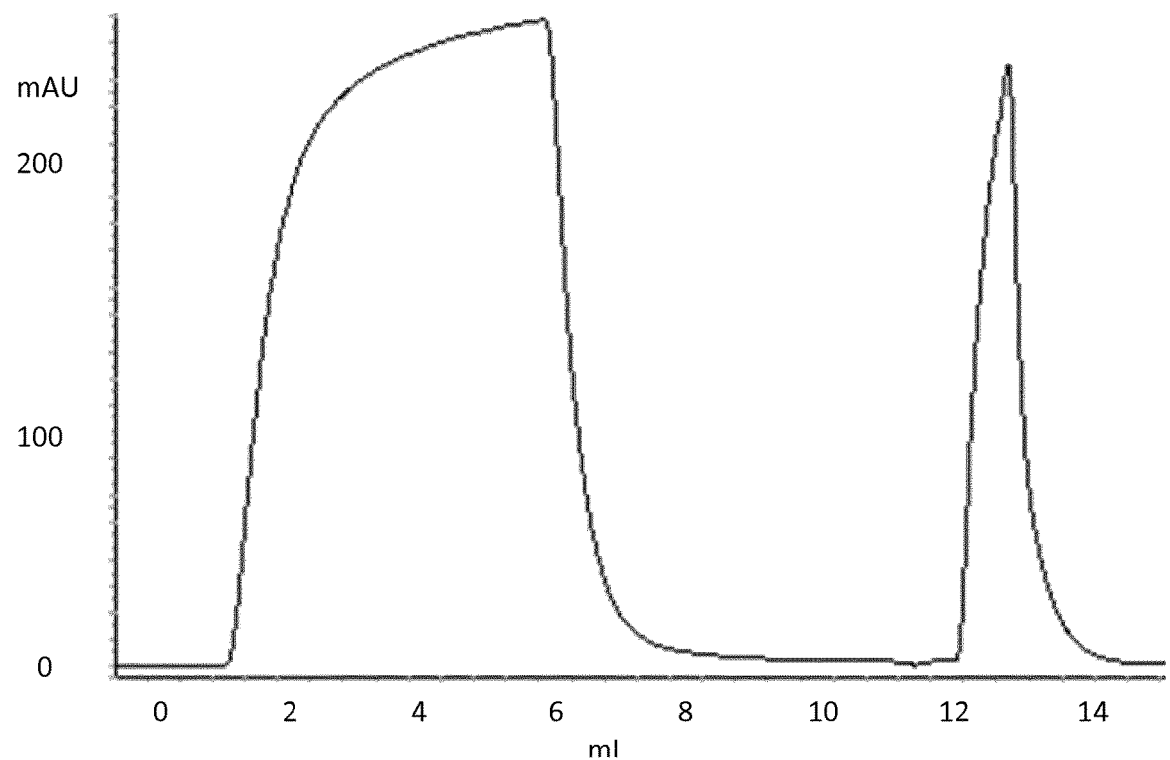
FIG. 7. Immobilization of IgG binding proteins to Sulfo-Link Coupling Resin. Shown are profiles of Ig binding protein 148470 (SEQ ID NO: 21) (FIG. 7A), and Ig binding protein 148460 (SEQ ID NO: 11) (FIG. 7B). The y-axis shows the absorption at 280 nm in mAU, the y-axis refers to the elution volume in ml.
Figure 7B:
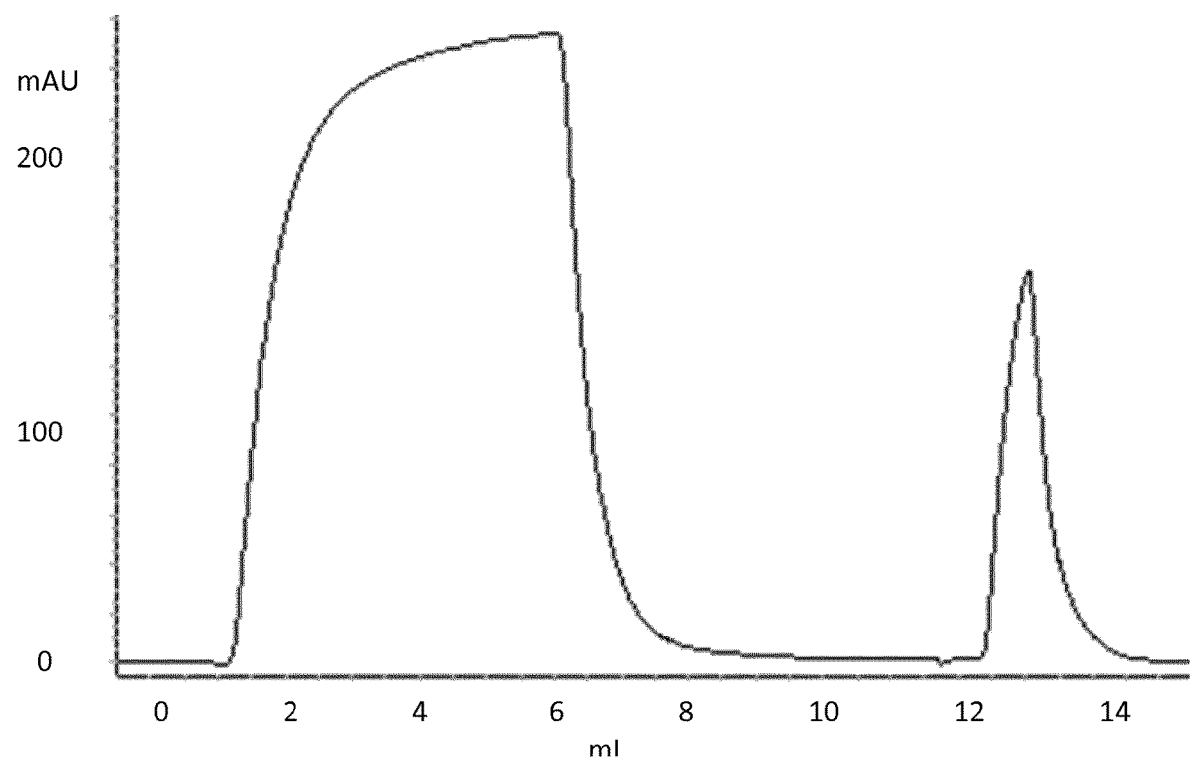

Absorbance at 280 nm was measured for all fractions. All IgG binding proteins could be covalently coupled to the matrix; FIG. 6 exemplarily shows the coupling of IgG binding proteins 148470 (FIG. 6A) and 148460 (FIG. 6B) to the SulfoLink coupling resin matrix.

Cetuximab was applied in saturated amounts (5 mg; 1 mg/ml resin) to the Sulfolink resin column with covalently coupled IgG binding protein. The matrix was washed with 100 mM glycine buffer, pH 2.5 to elute Cetuximab that was bound to the immobilized IgG binding protein. The concentration of the eluted IgG was spectroscopically measured in order to determine the binding activity (static binding capacity) of the Ig binding proteins. Elution fractions were analyzed at an absorbance at 280 nm. The IgG binding activity of immobilized proteins was analyzed before and after incubation with 0.5 M NaOH for 20, 40, or 80 minutes at room temperature. The IgG binding activity of immobilized proteins before NaOH treatment was defined as 100%. The IgG binding activity of the proteins was compared to the activity of naturally occurring domains C, B, A, D, E, or domain Z.

Figure 8:
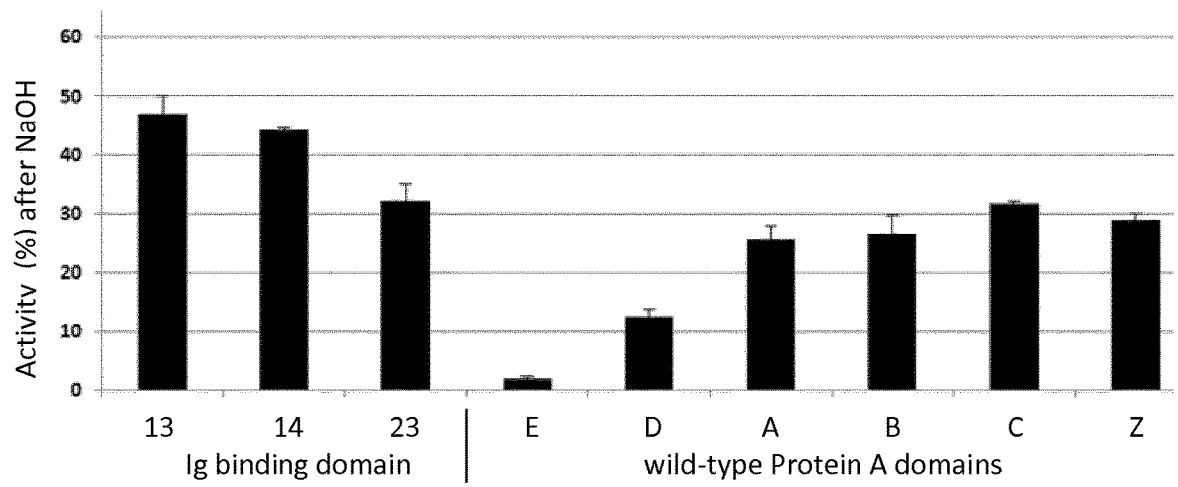
FIG. 8. Ig binding activity of IgG binding proteins immobilized to Sulfolink resin after alkaline treatment. The figure shows the remaining activity of different IgG binding proteins 148462 (SEQ ID NO: 13, "13"). 148463 (SEQ ID NO: 14; "14"). 1484672 (SEQ ID NO: 23, "23") in comparison to naturally occurring Protein A domains E, D, A, B, C, and to domain Z after 80 min of continuous 0.5 M NaOH treatment.

FIG. 8 shows the IgG binding activity of IgG binding proteins 148462 (referred to as "13" in the figure), 148463 (referred to as "14" in the figure), 148472 (referred to as "23" in the figure) and of naturally occurring Protein A domains E, D, A, B, C, and of domain Z. IgG binding activity is shown after incubation with 0.5 M NaOH for 80 min. IgG binding proteins of the invention show high binding activity to Cetuximab after alkaline treatment.

Figure 9:
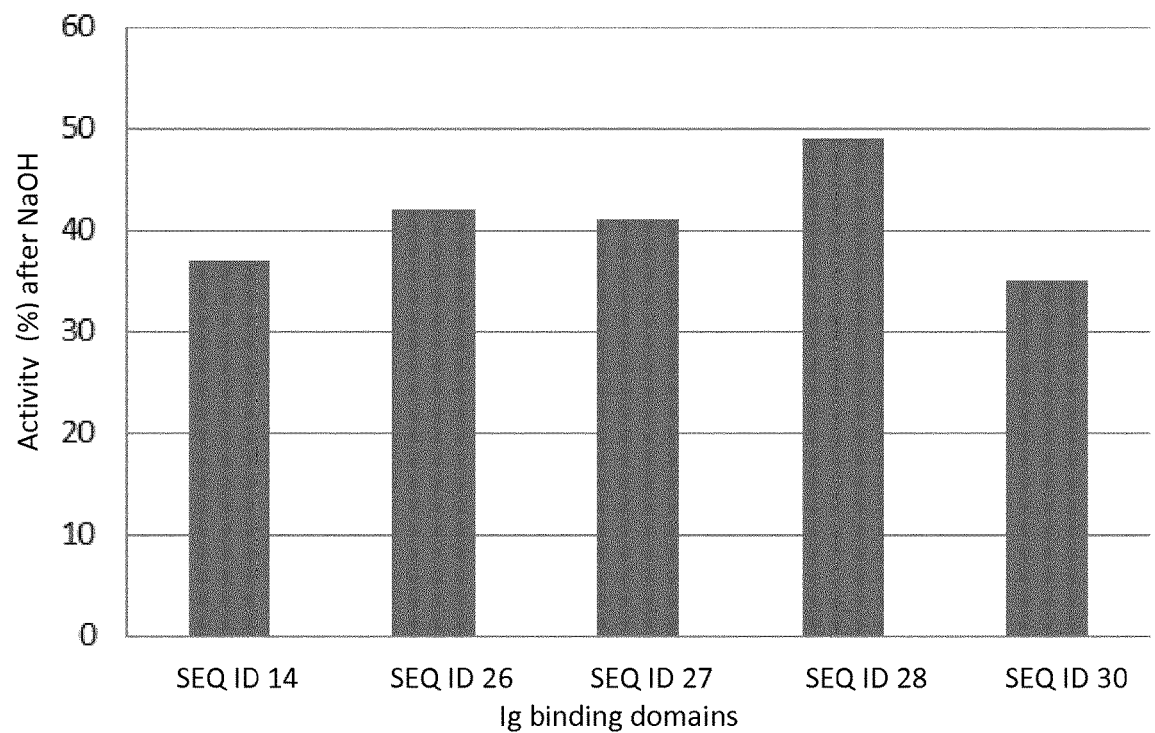
FIG. 9. Ig binding of IgG binding proteins immobilized to epoxy-activated resin after alkaline treatment. Ig binding proteins 154254 (SEQ ID NO: 26), 154255 (SEQ ID NO: 27), 154256 (SEQ ID NO: 28), and 154257 (SEQ ID NO: 30) were compared to IgG binding protein 148463 (SEQ ID NO: 14). The remaining activity after six hours of continuous 0.5 M NaOH treatment is shown.
Figure 10:
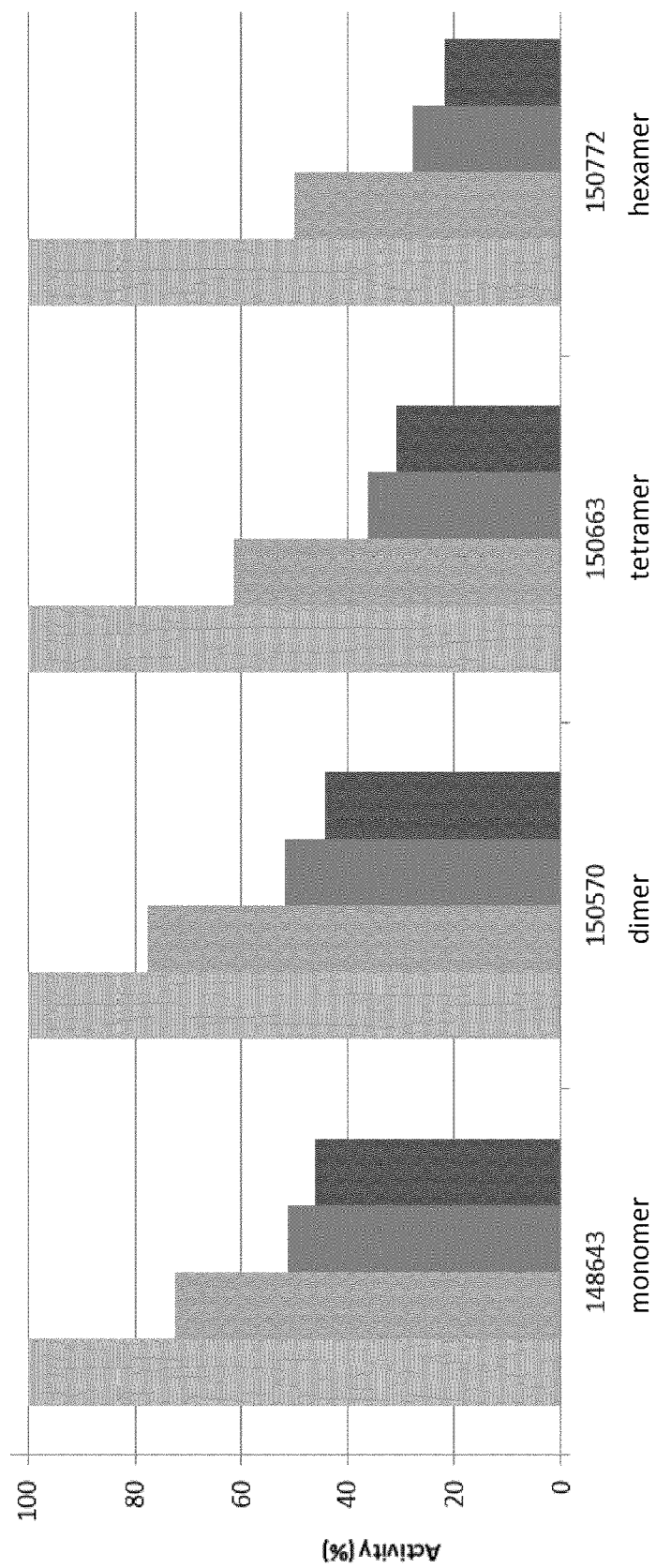
FIG. 10. Ig binding activity of IgG binding proteins consisting of 1, 2, 4, or 6 IgG binding domains immobilized to epoxy-activated resin after alkaline treatment. The IgG binding activity of monomer 148463 (SEQ ID NO: 14), dimer 150570 (SEQ ID NO: 45), tetramer 150663 (SEQ ID NO: 46), and hexamer 150772 (SEQ ID NO: 47) after continuous 0.5 M NaOH treatment is shown (0 hours, light grey column; 2 hours, medium grey column; 4 hours, dark medium grey column; 6 hours, dark grey column).

Example 8. Caustic Stability of IgG Binding Proteins Coupled to an Epoxy-Activated Matrix Purified IgG binding proteins were coupled to epoxy-activated matrix (Sepharose 6B, GE; Cat. No. 17-0480-01) according to the manufacturer's instructions (coupling conditions: pH 9.0 overnight, blocking for 5 h with ethanolamine). Cetuximab was used as IgG sample (5 mg; 1 mg/ml matrix). Cetuximab was applied in saturated amounts to the matrix comprising immobilized IgG binding protein. The matrix was washed with 100 mM glycine buffer, pH 2.5 to elute cetuximab that was bound to the immobilized IgG-binding protein. The concentration of the eluted IgG was spectroscopically measured at 280 nm in order to determine the binding activity (static binding capacity) of the Ig binding proteins. Columns were incubated with 0.5 M NaOH for 6 h at room temperature (22° C.+/−3° C.). The IgG binding activity of the immobilized proteins was analyzed before and after incubation with 0.5 M NaOH for 6 h. The IgG binding activity of immobilized proteins before NaOH treatment was defined as 100%. FIG. 9 shows that the activity of for example IgG binding proteins 154254 (referred to as "SEQ ID 26" in the figure), 154255 (referred to as "SEQ ID 27" in the figure), 154256 (referred to as "SEQ ID 28" in the figure), and 154257 (referred to as "SEQ ID 30" in the figure) was higher compared to the activity of IgG binding protein 148463 ("SEQ ID 14"), and thus higher than any naturally occurring Protein A domain. All immobilized IgG binding proteins showed at least 35% up to 50% of their original IgG binding activity after incubation for 6 h at 0.5 M NaOH. FIG. 10 shows that the Ig binding activity (capacity) of multimeric IgG binding proteins consisting of 2, 4, or 6 IgG binding domains immobilized to epoxy-activated resin after alkaline treatment for 0, 2, 4, 6 hours is comparable to the binding activity (capacity) of the monomeric IgG binding protein consisting of one IgG binding domain.

SEQUENCE LISTING FREE TEXT INFORMATION

SEQ ID NO: 1 generic sequence of non-natural Ig-binding domain
SEQ ID NO: 2 generic sequence of non-natural Ig-binding domain
SEQ ID NO: 3 *Staphylococcus aureus* domain E (CID 148473)
SEQ ID NO: 4 *Staphylococcus aureus* domain D (CID 148474)
SEQ ID NO: 5 *Staphylococcus aureus* domain A (CID 148475)
SEQ ID NO: 6 *Staphylococcus aureus* domain B (CID 148476)
SEQ ID NO: 7 *Staphylococcus aureus* domain C (CID 148477)
SEQ ID NO: 8 domain Z of protein A (CID 148478)
SEQ ID NO: 9 shuffle sequence IB9, CID 148458
SEQ ID NO: 10 shuffle sequence IB10, CID 148459
SEQ ID NO: 11 shuffle sequence IB11, CID 148460
SEQ ID NO: 12 shuffle sequence IB12, CID 148461
SEQ ID NO: 13 shuffle sequence IB13, CID 148462
SEQ ID NO: 14 shuffle sequence IB14, CID 148463
SEQ ID NO: 15 shuffle sequence IB15, CID 148464
SEQ ID NO: 16 shuffle sequence IB16, CID 148465
SEQ ID NO: 17 shuffle sequence IB17, CID 148466
SEQ ID NO: 18 shuffle sequence IB18, CID 148467
SEQ ID NO: 19 shuffle sequence IB19, CID 148468
SEQ ID NO: 20 shuffle sequence IB20, CID 148469
SEQ ID NO: 21 shuffle sequence IB21, CID 148470
SEQ ID NO: 22 shuffle sequence IB22, CID 148471
SEQ ID NO: 23 shuffle sequence IB23, CID 148472
SEQ ID NO: 24 shuffle sequence IB24, CID 154253
SEQ ID NO: 25 shuffle sequence IB15b
SEQ ID NO: 26 shuffle sequence IB25, CID 154254
SEQ ID NO: 27 shuffle sequence IB26, CID 154255
SEQ ID NO: 28 shuffle sequence IB27, CID 154256
SEQ ID NO: 29 shuffle sequence IB29
SEQ ID NO: 30 shuffle sequence IB28, CID 154257
SEQ ID NO: 31 linker
SEQ ID NO: 32 linker
SEQ ID NO: 33 linker
SEQ ID NO: 34 linker
SEQ ID NO: 35 linker
SEQ ID NO: 36 linker
SEQ ID NO: 37 linker
SEQ ID NO: 38 Generic sequence for non-natural Ig binding domain, for example for IB9-IB28
SEQ ID NO: 39 c-terminal coupling sequence (APS10/C)
SEQ ID NO: 40 c-terminal coupling sequence (APS30/C)
SEQ ID NO: 41 APS30 linker
SEQ ID NO: 42 APS30 linker
SEQ ID NO: 43 APS10 linker
SEQ ID NO: 44 Streptag
SEQ ID NO: 45 IB14 dimer, CID 150570
SEQ ID NO: 46 IB14 tetramer, CID 150663
SEQ ID NO: 47 IB14 hexamer, CID 150772
SEQ ID NO: 48 Generic sequence for e.g. IB24-IB28
SEQ ID NO: 49 Generic sequence for e.g. IB9-IB23
SEQ ID NO: 50 SEQ ID NO: 14 with c-terminal coupling sequence and strep-tag
SEQ ID NO: 51 SEQ ID NO: 28 with c-terminal coupling sequence and strep-tag

The invention claimed is:

1. A non-natural immunoglobulin (Ig) binding protein comprising one or more non-natural Ig-binding domains, wherein at least one non-natural Ig-binding domain comprises the amino acid sequence $X_1X_2X_3X_4X_5X_6X_7X_8QQX_{11}AFYEILHLPX_{21}LTEX_{25}QRX_{28}AFIQSLKDDPSX_{40}SX_{42}X_{43}X_{44}LX_{46}EAX_{49}KLX_{52}X_{53}X_{54}QAPX_{58}$ (SEQ ID NO: 38), and further wherein:

$X_1$ is N, V, P, or A;
$X_2$ is D or A;
$X_3$ is A, S, or N;
$X_4$ is K or Q;
$X_5$ is H or F;
$X_6$ is D, S, or A;
$X_7$ is E or K;
$X_8$ is D, E or A;
$X_{11}$ is S or N;
$X_{21}$ is N, S, or D;
$X_{25}$ is D or E;
$X_{28}$ is N, S, or A;
$X_{40}$ is V, T, or Q;
$X_{42}$ is K or A;
$X_{43}$ is E or S;
$X_{44}$ is V, L, or I;
$X_{46}$ is G or A;
$X_{49}$ is K or A;
$X_{52}$ is N, S, or D;
$X_{53}$ is D or E;
$X_{54}$ is S or A; and
$X_{58}$ is K or P;

wherein the dissociation constant $K_D$ of said non-natural Ig-binding protein to human IgG1 is 1 μM or less and wherein said non-natural Ig-binding protein is stable under alkaline conditions.

2. The non-natural Ig-binding protein of claim 1, wherein at least one non-natural Ig-binding domain comprises an amino acid sequence selected from the group consisting of:

(SEQ ID NO: 9)
NAAQHAKEQQNAFYEILHLPNLTEDQRAAFIQSLKDDPSVSKEILGEAKK
LNDAQAPP, (SEQ ID NO: 10)
NAAQHDKEQQNAFYEILHLPNLTEDQRAAFIQSLKDDPSVSKEILGEAKK
LNDAQAPP, (SEQ ID NO: 11)
NAAQHSKEQQNAFYEILHLPNLTEDQRSAFIQSLKDDPSVSKEILGEAKK
LNDAQAPP, (SEQ ID NO: 12)
NAAQHSKDQQSAFYEILHLPNLTEDQRSAFIQSLKDDPSVSKEILGEAKK
LNDAQAPP, (SEQ ID NO: 13)
PAAQHDKDQQSAFYEILHLPNLTEDQRSAFIQSLKDDPSVSKEILGEAKK
LNDAQAPP, (SEQ ID NO: 14)
PAAKHDKDQQSAFYEILHLPNLTEDQRSAFIQSLKDDPSVSKEILGEAKK
LNDAQAPP, (SEQ ID NO: 15)
ADNKFDEAQQSAFYEILHLPNLTEDQRAAFIQSLKDDPSVSKEILGEAKK
LNDAQAPP, (SEQ ID NO: 16)
ADSKFDEAQQSAFYEILHLPNLTEDQRAAFIQSLKDDPSVSKEILGEAKK
LNDAQAPP, (SEQ ID NO: 17)
ADSKFDEAQQSAFYEILHLPNLTEDQRAAFIQSLKDDPSVSKSLLGEAKK
LNDAQAPP, (SEQ ID NO: 18)
ADSKFDEAQQSAFYEILHLPDLTEDQRAAFIQSLKDDPSVSKSLLGEAKK
LNDAQAPP, (SEQ ID NO: 19)
ADSKFDEAQQSAFYEILHLPSLTEDQRAAFIQSLKDDPSVSKSLLGEAKK
LNDAQAPP, (SEQ ID NO: 20)
ADSKFDEAQQSAFYEILHLPSLTEDQRAAFIQSLKDDPSTSKSLLGEAKK
LNDAQAPP, (SEQ ID NO: 21)
ADSKFDEAQQSAFYEILHLPSLTEDQRAAFIQSLKDDPSTSKSLLGEAKK
LDDAQAPP, (SEQ ID NO: 22)
ADSKFDEAQQSAFYEILHLPSLTEDQRAAFIQSLKDDPSTSKSLLGEAKK
LSDAQAPP, (SEQ ID NO: 23)
PAAKHDKDQQSAFYEILHLPSLTEDQRAAFIQSLKDDPSTSKSILGEAKK
LNDAQAPP, (SEQ ID NO: 24)
NAAQHDKEQQNAFYEILHLPNLTEDQRNAFIQSLKDDPSVSKEILGEAKK
LNDAQAPK, (SEQ ID NO: 25)
ADNKFDEAQQSAFYEILHLPNLTEDQRNAFIQSLKDDPSVSKEILGEAKK
LNDAQAPK, (SEQ ID NO: 26)
NAAKHDKDQQSAFYEILHLPNLTEDQRNAFIQSLKDDPSVSKEILGEAKK
LNDAQAPP, (SEQ ID NO: 27)
NAAQHDKDQQSAFYEILHLPNLTEEQRNAFIQSLKDDPSVSKEILAEAKK
LNDAQAPK, (SEQ ID NO: 28)
NAAKFDEAQQSAFYEILHLPNLTEEQRNAFIQSLKDDPSVSKEVLGEAQK
LNDSQAPK, (SEQ ID NO: 29)
QQAQHDEAQQSAFYQVLHLPNLTADQRNAFIQSLKDDPSQSAEVLGEAQK
LNDSQAPK,
and (SEQ ID NO: 30)
VDAQHDEDQQSAFYEILHLPNLTEEQRNAFIQSLKDDPSQSAEILAEAKK
LNESQAPK.

3. The non-natural Ig-binding protein of claim 1, wherein said non-natural Ig-binding protein is stable under alkaline conditions.

4. The non-natural Ig-binding protein claim 1, comprising 2, 3, 4, 5, 6, 7, or 8 non-natural Ig-binding domains linked to each other.

5. The non-natural Ig-binding protein of claim 1, wherein said non-natural Ig-binding protein further comprises a specific attachment site for site-specific covalent attachment to a solid phase.

6. The non-natural immunoglobulin (Ig) binding protein of claim 1, wherein the dissociation constant $K_D$ of said non-natural Ig-binding protein to human IgG1 is 100 nM or less.

7. A composition comprising the non-natural immunoglobulin (Ig) binding protein of claim 1 coupled to a solid support.

8. A method for affinity purifying an immunoglobulin, the method comprising:
  a. providing a liquid containing an immunoglobulin;
  b. providing an affinity separation matrix comprising the non-natural Ig-binding protein of claim 1 immobilized on a solid support;
  c. contacting said affinity separation matrix with said liquid under conditions wherein said immunoglobulin binds to said immobilized non-natural Ig-binding protein; and
  d. eluting said immunoglobulin from said affinity separation matrix, thereby affinity purifying the immunoglobulin.

9. The method of claim 8, wherein the immunoglobulin is selected from the group consisting of human IgG1, human IgG2, human IgG4, human IgM, human IgA, mouse IgG1, mouse IgG2A, mouse IgG2B, mouse IgG3, rat IgG1, rat IgG2C, goat IgG1, goat IgG2, bovine IgG2, guinea pig IgG, rabbit IgG, an immunoglobulin fragment comprising an Fc region, a fusion protein comprising an Fc region of an immunoglobulin, and a conjugate comprising an Fc region of an immunoglobulin.

10. The method of claim 8, further comprising washing said affinity separation matrix one or more times between steps (c) and (d).

11. A method for generating an amino acid sequence of a non-natural immunoglobulin (Ig) binding protein of claim 1, the method comprising:
  (a) providing a set of amino acid sequences to be shuffled, wherein each member of the set of amino acid sequences to be shuffled comprises an amino acid sequence of an immunoglobulin (Ig) binding domain of a naturally occurring Protein A polypeptide or an immunoglobulin (Ig) binding derivative thereof;
  (b) aligning each of the amino acid sequences;
  (c) statistically fragmenting the aligned amino acid sequences in silico; and
  (d) assembling the statistically fragmented amino acid sequences in silico to produce an amino acid sequence of a non-natural immunoglobulin (Ig) binding protein of claim 1, wherein the assembling maintains relative order of the statistically fragmented amino acid sequences in the amino acid sequence of the non-natural immunoglobulin (Ig) binding protein of claim 1 as said statistically fragmented amino acid sequences are present in the amino acid sequences of immunoglobulin (Ig) binding domains of the replaced with Protein A polypeptides;
  (e) and further comprising synthesizing the non-natural immunoglobulin (Ig) binding protein of claim 1.

* * * * *

SEQUENCE LISTING

```
<160> NUMBER OF SEQ ID NOS: 49

<210> SEQ ID NO 1
<211> LENGTH: 58
<212> TYPE: PRT
<213> ORGANISM: Artificial Sequence
<220> FEATURE:
<223> OTHER INFORMATION: Generic sequence of non-natural Ig-binding
      domain
<220> FEATURE:
<221> NAME/KEY: misc_feature
<222> LOCATION: (1)..(1)
<223> OTHER INFORMATION: may be A, P, V, Q, or N
<220> FEATURE:
<221> NAME/KEY: misc_feature
<222> LOCATION: (2)..(2)
```

```
<223> OTHER INFORMATION: may be D, A, or Q
<220> FEATURE:
<221> NAME/KEY: misc_feature
<222> LOCATION: (3)..(3)
<223> OTHER INFORMATION: may be A, N, or S
<220> FEATURE:
<221> NAME/KEY: misc_feature
<222> LOCATION: (4)..(4)
<223> OTHER INFORMATION: may be K, Q, or N
<220> FEATURE:
<221> NAME/KEY: misc_feature
<222> LOCATION: (5)..(5)
<223> OTHER INFORMATION: may be H or F
<220> FEATURE:
<221> NAME/KEY: misc_feature
<222> LOCATION: (6)..(6)
<223> OTHER INFORMATION: may be D, N, S, or A
<220> FEATURE:
<221> NAME/KEY: misc_feature
<222> LOCATION: (7)..(7)
<223> OTHER INFORMATION: may be E or K
<220> FEATURE:
<221> NAME/KEY: misc_feature
<222> LOCATION: (8)..(8)
<223> OTHER INFORMATION: may be D, A, or E
<220> FEATURE:
<221> NAME/KEY: misc_feature
<222> LOCATION: (11)..(11)
<223> OTHER INFORMATION: may be S or N
<220> FEATURE:
<221> NAME/KEY: misc_feature
<222> LOCATION: (15)..(15)
<223> OTHER INFORMATION: may be E, D, or Q
<220> FEATURE:
<221> NAME/KEY: misc_feature
<222> LOCATION: (16)..(16)
<223> OTHER INFORMATION: may be V or I
<220> FEATURE:
<221> NAME/KEY: misc_feature
<222> LOCATION: (18)..(18)
<223> OTHER INFORMATION: may be H or N
<220> FEATURE:
<221> NAME/KEY: misc_feature
<222> LOCATION: (19)..(19)
<223> OTHER INFORMATION: may be L or M
<220> FEATURE:
<221> NAME/KEY: misc_feature
<222> LOCATION: (21)..(21)
<223> OTHER INFORMATION: may be N, S, or D
<220> FEATURE:
<221> NAME/KEY: misc_feature
<222> LOCATION: (23)..(23)
<223> OTHER INFORMATION: may be T or N
<220> FEATURE:
<221> NAME/KEY: misc_feature
<222> LOCATION: (24)..(24)
<223> OTHER INFORMATION: may be E or A
<220> FEATURE:
<221> NAME/KEY: misc_feature
<222> LOCATION: (25)..(25)
<223> OTHER INFORMATION: may be D or E
<220> FEATURE:
<221> NAME/KEY: misc_feature
<222> LOCATION: (28)..(28)
<223> OTHER INFORMATION: may be N, S, or A
<220> FEATURE:
<221> NAME/KEY: misc_feature
<222> LOCATION: (29)..(29)
<223> OTHER INFORMATION: may be G or A
<220> FEATURE:
<221> NAME/KEY: misc_feature
<222> LOCATION: (40)..(40)
<223> OTHER INFORMATION: may be V, Q, or T
<220> FEATURE:
<221> NAME/KEY: misc_feature
<222> LOCATION: (42)..(42)
<223> OTHER INFORMATION: may be K, T, or A
<220> FEATURE:
<221> NAME/KEY: misc_feature
```

```
<222> LOCATION: (43)..(43)
<223> OTHER INFORMATION: may be E, N, or S
<220> FEATURE:
<221> NAME/KEY: misc_feature
<222> LOCATION: (44)..(44)
<223> OTHER INFORMATION: may be V, L, or I
<220> FEATURE:
<221> NAME/KEY: misc_feature
<222> LOCATION: (46)..(46)
<223> OTHER INFORMATION: may be G or A
<220> FEATURE:
<221> NAME/KEY: misc_feature
<222> LOCATION: (49)..(49)
<223> OTHER INFORMATION: may be K or Q
<220> FEATURE:
<221> NAME/KEY: misc_feature
<222> LOCATION: (52)..(52)
<223> OTHER INFORMATION: may be N, D, or S
<220> FEATURE:
<221> NAME/KEY: misc_feature
<222> LOCATION: (53)..(53)
<223> OTHER INFORMATION: may be D or E
<220> FEATURE:
<221> NAME/KEY: misc_feature
<222> LOCATION: (54)..(54)
<223> OTHER INFORMATION: may be S or A
<220> FEATURE:
<221> NAME/KEY: misc_feature
<222> LOCATION: (56)..(56)
<223> OTHER INFORMATION: may be A or P
<220> FEATURE:
<221> NAME/KEY: misc_feature
<222> LOCATION: (58)..(58)
<223> OTHER INFORMATION: may be K or P

<400> SEQUENCE: 1

Xaa Xaa Xaa Xaa Xaa Xaa Xaa Xaa Gln Gln Xaa Ala Phe Tyr Xaa Xaa
1               5                   10                  15

Leu Xaa Xaa Pro Xaa Leu Xaa Xaa Xaa Gln Arg Xaa Xaa Phe Ile Gln
            20                  25                  30

Ser Leu Lys Asp Asp Pro Ser Xaa Ser Xaa Xaa Xaa Leu Xaa Glu Ala
        35                  40                  45

Xaa Lys Leu Xaa Xaa Xaa Gln Xaa Pro Xaa
    50                  55

<210> SEQ ID NO 2
<211> LENGTH: 58
<212> TYPE: PRT
<213> ORGANISM: Artificial Sequence
<220> FEATURE:
<223> OTHER INFORMATION: Generic sequence of non-natural Ig-binding
      domain
<220> FEATURE:
<221> NAME/KEY: misc_feature
<222> LOCATION: (1)..(1)
<223> OTHER INFORMATION: may be A, V, Q, N, or P
<220> FEATURE:
<221> NAME/KEY: misc_feature
<222> LOCATION: (2)..(2)
<223> OTHER INFORMATION: may be D, A, or Q
<220> FEATURE:
<221> NAME/KEY: misc_feature
<222> LOCATION: (3)..(3)
<223> OTHER INFORMATION: may be A, N, or S
<220> FEATURE:
<221> NAME/KEY: misc_feature
<222> LOCATION: (4)..(4)
<223> OTHER INFORMATION: may be K, Q, or N
<220> FEATURE:
<221> NAME/KEY: misc_feature
<222> LOCATION: (5)..(5)
<223> OTHER INFORMATION: may be H or F
<220> FEATURE:
<221> NAME/KEY: misc_feature
```

```
<222> LOCATION: (6)..(6)
<223> OTHER INFORMATION: may be D, N, A, or S
<220> FEATURE:
<221> NAME/KEY: misc_feature
<222> LOCATION: (7)..(7)
<223> OTHER INFORMATION: may be E or K
<220> FEATURE:
<221> NAME/KEY: misc_feature
<222> LOCATION: (8)..(8)
<223> OTHER INFORMATION: may be D, E, or A
<220> FEATURE:
<221> NAME/KEY: misc_feature
<222> LOCATION: (11)..(11)
<223> OTHER INFORMATION: may be S or N
<220> FEATURE:
<221> NAME/KEY: misc_feature
<222> LOCATION: (15)..(15)
<223> OTHER INFORMATION: may be E or Q
<220> FEATURE:
<221> NAME/KEY: misc_feature
<222> LOCATION: (16)..(16)
<223> OTHER INFORMATION: may be V or I
<220> FEATURE:
<221> NAME/KEY: misc_feature
<222> LOCATION: (18)..(18)
<223> OTHER INFORMATION: may be H or N
<220> FEATURE:
<221> NAME/KEY: misc_feature
<222> LOCATION: (19)..(19)
<223> OTHER INFORMATION: may be L or M
<220> FEATURE:
<221> NAME/KEY: misc_feature
<222> LOCATION: (21)..(21)
<223> OTHER INFORMATION: may be N, S, or D
<220> FEATURE:
<221> NAME/KEY: misc_feature
<222> LOCATION: (23)..(23)
<223> OTHER INFORMATION: may be T or N
<220> FEATURE:
<221> NAME/KEY: misc_feature
<222> LOCATION: (24)..(24)
<223> OTHER INFORMATION: may be E or A
<220> FEATURE:
<221> NAME/KEY: misc_feature
<222> LOCATION: (25)..(25)
<223> OTHER INFORMATION: may be D or E
<220> FEATURE:
<221> NAME/KEY: misc_feature
<222> LOCATION: (28)..(28)
<223> OTHER INFORMATION: may be N, S, or A
<220> FEATURE:
<221> NAME/KEY: misc_feature
<222> LOCATION: (29)..(29)
<223> OTHER INFORMATION: may be G or A
<220> FEATURE:
<221> NAME/KEY: misc_feature
<222> LOCATION: (40)..(40)
<223> OTHER INFORMATION: may be V, Q, or T
<220> FEATURE:
<221> NAME/KEY: misc_feature
<222> LOCATION: (42)..(42)
<223> OTHER INFORMATION: may be K, T, or A
<220> FEATURE:
<221> NAME/KEY: misc_feature
<222> LOCATION: (43)..(43)
<223> OTHER INFORMATION: may be E, N, or S
<220> FEATURE:
<221> NAME/KEY: misc_feature
<222> LOCATION: (44)..(44)
<223> OTHER INFORMATION: may be V, L, or I
<220> FEATURE:
<221> NAME/KEY: misc_feature
<222> LOCATION: (46)..(46)
<223> OTHER INFORMATION: may be G or A
<220> FEATURE:
<221> NAME/KEY: misc_feature
<222> LOCATION: (49)..(49)
<223> OTHER INFORMATION: may be K or Q
<220> FEATURE:
```

```
<221> NAME/KEY: misc_feature
<222> LOCATION: (52)..(52)
<223> OTHER INFORMATION: may be N, D, or S
<220> FEATURE:
<221> NAME/KEY: misc_feature
<222> LOCATION: (53)..(53)
<223> OTHER INFORMATION: may be D or E
<220> FEATURE:
<221> NAME/KEY: misc_feature
<222> LOCATION: (54)..(54)
<223> OTHER INFORMATION: may be S or A
<220> FEATURE:
<221> NAME/KEY: misc_feature
<222> LOCATION: (56)..(56)
<223> OTHER INFORMATION: may be A or P
<220> FEATURE:
<221> NAME/KEY: misc_feature
<222> LOCATION: (58)..(58)
<223> OTHER INFORMATION: may be K or P

<400> SEQUENCE: 2

Xaa Xaa Xaa Xaa Xaa Xaa Xaa Gln Gln Xaa Ala Phe Tyr Xaa Xaa
1               5                   10                  15

Leu Xaa Xaa Pro Xaa Leu Xaa Xaa Xaa Gln Arg Xaa Xaa Phe Ile Gln
                20                  25                  30

Ser Leu Lys Asp Asp Pro Ser Xaa Ser Xaa Xaa Xaa Leu Xaa Glu Ala
        35                  40                  45

Xaa Lys Leu Xaa Xaa Xaa Gln Xaa Pro Xaa
    50                  55

<210> SEQ ID NO 3
<211> LENGTH: 65
<212> TYPE: PRT
<213> ORGANISM: Staphylococcus aureus

<400> SEQUENCE: 3

Thr Pro Ala Ala Asn Ala Ala Gln His Asp Glu Ala Gln Gln Asn Ala
1               5                   10                  15

Phe Tyr Gln Val Leu Asn Met Pro Asn Leu Asn Ala Asp Gln Arg Asn
                20                  25                  30

Gly Phe Ile Gln Ser Leu Lys Asp Asp Pro Ser Gln Ser Ala Asn Val
            35                  40                  45

Leu Gly Glu Ala Gln Lys Leu Asn Asp Ser Gln Ala Pro Lys Ala Asp
    50                  55                  60

Ala
65

<210> SEQ ID NO 4
<211> LENGTH: 58
<212> TYPE: PRT
<213> ORGANISM: Staphylococcus aureus

<400> SEQUENCE: 4

Gln Gln Asn Lys Phe Asn Lys Asp Gln Gln Ser Ala Phe Tyr Glu Ile
1               5                   10                  15

Leu Asn Met Pro Asn Leu Asn Glu Glu Gln Arg Asn Gly Phe Ile Gln
                20                  25                  30

Ser Leu Lys Asp Asp Pro Ser Gln Ser Thr Asn Val Leu Gly Glu Ala
            35                  40                  45

Lys Lys Leu Asn Glu Ser Gln Ala Pro Lys
    50                  55

<210> SEQ ID NO 5
```

```
<211> LENGTH: 58
<212> TYPE: PRT
<213> ORGANISM: Staphylococcus aureus

<400> SEQUENCE: 5

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 6
<211> LENGTH: 58
<212> TYPE: PRT
<213> ORGANISM: Staphylococcus aureus

<400> SEQUENCE: 6

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Staphylococcus aureus

<400> SEQUENCE: 7

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: domain Z of protein A  (CID 148478)

<400> SEQUENCE: 8

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

```
<210> SEQ ID NO 9
<211> LENGTH: 58
<212> TYPE: PRT
<213> ORGANISM: Artificial Sequence
<220> FEATURE:
<223> OTHER INFORMATION: Artificial shuffle sequence IB9, CID 148458

<400> SEQUENCE: 9

Asn Ala Ala Gln His Ala Lys Glu Gln Gln Asn Ala Phe Tyr Glu Ile
1               5                   10                  15

Leu His Leu Pro Asn Leu Thr Glu Asp Gln Arg Ala Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 10
<211> LENGTH: 58
<212> TYPE: PRT
<213> ORGANISM: Artificial Sequence
<220> FEATURE:
<223> OTHER INFORMATION: Artificial shuffle sequence IB10, CID 148459

<400> SEQUENCE: 10

Asn Ala Ala Gln His Asp Lys Glu Gln Gln Asn Ala Phe Tyr Glu Ile
1               5                   10                  15

Leu His Leu Pro Asn Leu Thr Glu Asp Gln Arg Ala Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 11
<211> LENGTH: 58
<212> TYPE: PRT
<213> ORGANISM: Artificial Sequence
<220> FEATURE:
<223> OTHER INFORMATION: Artificial shuffle sequence IB11, CID 148460

<400> SEQUENCE: 11

Asn Ala Ala Gln His Ser Lys Glu Gln Gln Asn Ala Phe Tyr Glu Ile
1               5                   10                  15

Leu His Leu Pro Asn Leu Thr Glu Asp Gln Arg Ser Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 12
<211> LENGTH: 58
<212> TYPE: PRT
<213> ORGANISM: Artificial Sequence
<220> FEATURE:
<223> OTHER INFORMATION: Artificial shuffle sequence IB12, CID 148461

<400> SEQUENCE: 12

Asn Ala Ala Gln His Ser Lys Asp Gln Gln Ser Ala Phe Tyr Glu Ile
1               5                   10                  15
```

```
Leu His Leu Pro Asn Leu Thr Glu Asp Gln Arg Ser Ala Phe Ile Gln
        20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
        50                  55

<210> SEQ ID NO 13
<211> LENGTH: 58
<212> TYPE: PRT
<213> ORGANISM: Artificial Sequence
<220> FEATURE:
<223> OTHER INFORMATION: Artificial shuffle sequence IB13, CID 148462

<400> SEQUENCE: 13

Pro Ala Ala Gln His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
        20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
        50                  55

<210> SEQ ID NO 14
<211> LENGTH: 58
<212> TYPE: PRT
<213> ORGANISM: Artificial Sequence
<220> FEATURE:
<223> OTHER INFORMATION: Artificial shuffle sequence IB14, CID 148463

<400> SEQUENCE: 14

Pro Ala Ala Lys His Asp Lys Asp Gln Gln Ser Ala Phe Tyr Glu Ile
1               5                   10                  15

Leu His Leu Pro Asn Leu Thr Glu Asp Gln Arg Ser Ala Phe Ile Gln
        20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
        50                  55

<210> SEQ ID NO 15
<211> LENGTH: 58
<212> TYPE: PRT
<213> ORGANISM: Artificial Sequence
<220> FEATURE:
<223> OTHER INFORMATION: Artificial shuffle sequence IB15, CID 148464

<400> SEQUENCE: 15

Ala Asp Asn Lys Phe Asp Glu Ala Gln Gln Ser Ala Phe Tyr Glu Ile
1               5                   10                  15

Leu His Leu Pro Asn Leu Thr Glu Asp Gln Arg Ala Ala Phe Ile Gln
        20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
        50                  55

<210> SEQ ID NO 16
<211> LENGTH: 58
```

```
<212> TYPE: PRT
<213> ORGANISM: Artificial Sequence
<220> FEATURE:
<223> OTHER INFORMATION: Artificial shuffle sequence IB16, CID 148465

<400> SEQUENCE: 16

Ala Asp Ser Lys Phe Asp Glu Ala Gln Gln Ser Ala Phe Tyr Glu Ile
1               5                   10                  15

Leu His Leu Pro Asn Leu Thr Glu Asp Gln Arg Ala Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
    50                  55

<210> SEQ ID NO 17
<211> LENGTH: 58
<212> TYPE: PRT
<213> ORGANISM: Artificial Sequence
<220> FEATURE:
<223> OTHER INFORMATION: Artificial shuffle sequence IB17, CID 148466

<400> SEQUENCE: 17

Ala Asp Ser Lys Phe Asp Glu Ala Gln Gln Ser Ala Phe Tyr Glu Ile
1               5                   10                  15

Leu His Leu Pro Asn Leu Thr Glu Asp Gln Arg Ala Ala Phe Ile Gln
            20                  25                  30

Ser Leu Lys Asp Asp Pro Ser Val Ser Lys Ser Leu Leu Gly Glu Ala
        35                  40                  45

Lys Lys Leu Asn Asp Ala Gln Ala Pro Pro
    50                  55

<210> SEQ ID NO 18
<211> LENGTH: 58
<212> TYPE: PRT
<213> ORGANISM: Artificial Sequence
<220> FEATURE:
<223> OTHER INFORMATION: Artificial shuffle sequence IB18, CID 148467

<400> SEQUENCE: 18

Ala Asp Ser Lys Phe Asp Glu Ala Gln Gln Ser Ala Phe Tyr Glu Ile
1               5                   10                  15

Leu His Leu Pro Asp Leu Thr Glu Asp Gln Arg Ala Ala Phe Ile Gln
            20                  25                  30

Ser Leu Lys Asp Asp Pro Ser Val Ser Lys Ser Leu Leu Gly Glu Ala
        35                  40                  45

Lys Lys Leu Asn Asp Ala Gln Ala Pro Pro
    50                  55

<210> SEQ ID NO 19
<211> LENGTH: 58
<212> TYPE: PRT
<213> ORGANISM: Artificial Sequence
<220> FEATURE:
<223> OTHER INFORMATION: Artificial shuffle sequence IB19, CID 148468

<400> SEQUENCE: 19

Ala Asp Ser Lys Phe Asp Glu Ala Gln Gln Ser Ala Phe Tyr Glu Ile
1               5                   10                  15

Leu His Leu Pro Ser Leu Thr Glu Asp Gln Arg Ala Ala Phe Ile Gln
            20                  25                  30
```

Ser Leu Lys Asp Asp Pro Ser Val Ser Lys Ser Leu Leu Gly Glu Ala
            35                  40                  45

Lys Lys Leu Asn Asp Ala Gln Ala Pro Pro
        50                  55

<210> SEQ ID NO 20
<211> LENGTH: 58
<212> TYPE: PRT
<213> ORGANISM: Artificial Sequence
<220> FEATURE:
<223> OTHER INFORMATION: Artificial shuffle sequence IB20, CID 148469

<400> SEQUENCE: 20

Ala Asp Ser Lys Phe Asp Glu Ala Gln Gln Ser Ala Phe Tyr Glu Ile
1               5                   10                  15

Leu His Leu Pro Ser Leu Thr Glu Asp Gln Arg Ala Ala Phe Ile Gln
            20                  25                  30

Ser Leu Lys Asp Asp Pro Ser Thr Ser Lys Ser Leu Leu Gly Glu Ala
            35                  40                  45

Lys Lys Leu Asn Asp Ala Gln Ala Pro Pro
        50                  55

<210> SEQ ID NO 21
<211> LENGTH: 58
<212> TYPE: PRT
<213> ORGANISM: Artificial Sequence
<220> FEATURE:
<223> OTHER INFORMATION: Artificial shuffle sequence IB21, CID 148470

<400> SEQUENCE: 21

Ala Asp Ser Lys Phe Asp Glu Ala Gln Gln Ser Ala Phe Tyr Glu Ile
1               5                   10                  15

Leu His Leu Pro Ser Leu Thr Glu Asp Gln Arg Ala Ala Phe Ile Gln
            20                  25                  30

Ser Leu Lys Asp Asp Pro Ser Thr Ser Lys Ser Leu Leu Gly Glu Ala
            35                  40                  45

Lys Lys Leu Asp Asp Ala Gln Ala Pro Pro
        50                  55

<210> SEQ ID NO 22
<211> LENGTH: 58
<212> TYPE: PRT
<213> ORGANISM: Artificial Sequence
<220> FEATURE:
<223> OTHER INFORMATION: Artificial shuffle sequence IB22, CID 148471

<400> SEQUENCE: 22

Ala Asp Ser Lys Phe Asp Glu Ala Gln Gln Ser Ala Phe Tyr Glu Ile
1               5                   10                  15

Leu His Leu Pro Ser Leu Thr Glu Asp Gln Arg Ala Ala Phe Ile Gln
            20                  25                  30

Ser Leu Lys Asp Asp Pro Ser Thr Ser Lys Ser Leu Leu Gly Glu Ala
            35                  40                  45

Lys Lys Leu Ser Asp Ala Gln Ala Pro Pro
        50                  55

<210> SEQ ID NO 23
<211> LENGTH: 58
<212> TYPE: PRT
<213> ORGANISM: Artificial Sequence
<220> FEATURE:
<223> OTHER INFORMATION: Artificial shuffle sequence IB23, CID 148472

```
<400> SEQUENCE: 23

Pro Ala Ala Lys His Asp Lys Asp Gln Gln Ser Ala Phe Tyr Glu Ile
1               5                   10                  15

Leu His Leu Pro Ser Leu Thr Glu Asp Gln Arg Ala Ala Phe Ile Gln
            20                  25                  30

Ser Leu Lys Asp Asp Pro Ser Thr Ser Lys Ser Ile Leu Gly Glu Ala
        35                  40                  45

Lys Lys Leu Asn Asp Ala Gln Ala Pro Pro
    50                  55

<210> SEQ ID NO 24
<211> LENGTH: 58
<212> TYPE: PRT
<213> ORGANISM: Artificial Sequence
<220> FEATURE:
<223> OTHER INFORMATION: Artificial shuffle sequence IB24 (CID 154253)

<400> SEQUENCE: 24

Asn Ala Ala Gln His Asp Lys Glu Gln Gln Asn Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Lys
    50                  55

<210> SEQ ID NO 25
<211> LENGTH: 58
<212> TYPE: PRT
<213> ORGANISM: Artificial Sequence
<220> FEATURE:
<223> OTHER INFORMATION: Artificial shuffle sequence IB15b

<400> SEQUENCE: 25

Ala Asp Asn Lys Phe Asp Glu Ala Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Lys
    50                  55

<210> SEQ ID NO 26
<211> LENGTH: 58
<212> TYPE: PRT
<213> ORGANISM: Artificial Sequence
<220> FEATURE:
<223> OTHER INFORMATION: Artificial shuffle sequence IB25 (CID 154254)

<400> SEQUENCE: 26

Asn Ala Ala Lys His Asp Lys Asp Gln Gln Ser Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Lys Asp Asp Pro Ser Val Ser Lys Glu Ile Leu Gly Glu Ala
        35                  40                  45

Lys Lys Leu Asn Asp Ala Gln Ala Pro Pro
```

<210> SEQ ID NO 27
<211> LENGTH: 58
<212> TYPE: PRT
<213> ORGANISM: Artificial Sequence
<220> FEATURE:
<223> OTHER INFORMATION: Artificial shuffle sequence IB26 (CID 154255)

<400> SEQUENCE: 27

Asn Ala Ala Gln His Asp Lys Asp Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 28
<211> LENGTH: 58
<212> TYPE: PRT
<213> ORGANISM: Artificial Sequence
<220> FEATURE:
<223> OTHER INFORMATION: Artificial shuffle sequence IB27 (CID 154256)

<400> SEQUENCE: 28

Asn Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Val Leu Gly Glu Ala
        35                  40                  45

Gln Lys Leu Asn Asp Ser Gln Ala Pro Lys
    50                  55

<210> SEQ ID NO 29
<211> LENGTH: 58
<212> TYPE: PRT
<213> ORGANISM: Artificial Sequence
<220> FEATURE:
<223> OTHER INFORMATION: Artificial shuffle sequence IB29

<400> SEQUENCE: 29

Gln Gln Ala Gln His Asp Glu Ala Gln Gln Ser Ala Phe Tyr Gln Val
1               5                   10                  15

Leu His Leu Pro Asn Leu Thr Ala Asp Gln Arg Asn Ala Phe Ile Gln
            20                  25                  30

Ser Leu Lys Asp Asp Pro Ser Gln Ser Ala Glu Val Leu Gly Glu Ala
        35                  40                  45

Gln Lys Leu Asn Asp Ser Gln Ala Pro Lys
    50                  55

<210> SEQ ID NO 30
<211> LENGTH: 58
<212> TYPE: PRT
<213> ORGANISM: Artificial Sequence
<220> FEATURE:
<223> OTHER INFORMATION: Artificial shuffle sequence IB28 (CID 154257)

<400> SEQUENCE: 30

Val Asp Ala Gln His Asp Glu Asp Gln Gln Ser Ala Phe Tyr Glu Ile

```
                1               5                   10                  15
Leu His Leu Pro Asn Leu Thr Glu Glu Gln Arg Asn Ala Phe Ile Gln
                20                  25                  30

Ser Leu Lys Asp Asp Pro Ser Gln Ser Ala Glu Ile Leu Ala Glu Ala
            35                  40                  45

Lys Lys Leu Asn Glu Ser Gln Ala Pro Lys
        50                  55

<210> SEQ ID NO 31
<211> LENGTH: 5
<212> TYPE: PRT
<213> ORGANISM: Artificial Sequence
<220> FEATURE:
<223> OTHER INFORMATION: Artificially synthesized linker

<400> SEQUENCE: 31

Ser Gly Gly Gly Gly
1               5

<210> SEQ ID NO 32
<211> LENGTH: 10
<212> TYPE: PRT
<213> ORGANISM: Artificial Sequence
<220> FEATURE:
<223> OTHER INFORMATION: Artificially synthesized linker

<400> SEQUENCE: 32

Ser Gly Gly Gly Gly Ser Gly Gly Gly Gly
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Artificially synthesized linker

<400> SEQUENCE: 33

Gly Gly Gly Ser Gly Gly Gly Ser Gly Gly Gly Ser
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Artificially synthesized linker

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 5
<212> TYPE: PRT
<213> ORGANISM: Artificial Sequence
<220> FEATURE:
<223> OTHER INFORMATION: Artificially synthesized linker

<400> SEQUENCE: 35

Gly Gly Gly Gly Ser
1               5

<210> SEQ ID NO 36
<211> LENGTH: 4
```

```
<212> TYPE: PRT
<213> ORGANISM: Artificial Sequence
<220> FEATURE:
<223> OTHER INFORMATION: Artificially synthesized linker

<400> SEQUENCE: 36

Gly Gly Gly Ser
1

<210> SEQ ID NO 37
<211> LENGTH: 4
<212> TYPE: PRT
<213> ORGANISM: Artificial Sequence
<220> FEATURE:
<223> OTHER INFORMATION: Artificially synthesized linker

<400> SEQUENCE: 37

Ser Gly Gly Gly
1

<210> SEQ ID NO 38
<211> LENGTH: 58
<212> TYPE: PRT
<213> ORGANISM: Artificial Sequence
<220> FEATURE:
<223> OTHER INFORMATION: Artificially synthesized generic sequence of
      non-natural Ig-binding domain (e.g. for IB9-IB28)
<220> FEATURE:
<221> NAME/KEY: misc_feature
<222> LOCATION: (1)..(1)
<223> OTHER INFORMATION: may be A, N, P, or V
<220> FEATURE:
<221> NAME/KEY: misc_feature
<222> LOCATION: (2)..(2)
<223> OTHER INFORMATION: may be D or A
<220> FEATURE:
<221> NAME/KEY: misc_feature
<222> LOCATION: (3)..(3)
<223> OTHER INFORMATION: may be A, N, or S
<220> FEATURE:
<221> NAME/KEY: misc_feature
<222> LOCATION: (4)..(4)
<223> OTHER INFORMATION: may be K or Q
<220> FEATURE:
<221> NAME/KEY: misc_feature
<222> LOCATION: (5)..(5)
<223> OTHER INFORMATION: may be H or F
<220> FEATURE:
<221> NAME/KEY: misc_feature
<222> LOCATION: (6)..(6)
<223> OTHER INFORMATION: may be D, S, or A
<220> FEATURE:
<221> NAME/KEY: misc_feature
<222> LOCATION: (7)..(7)
<223> OTHER INFORMATION: may be E or K
<220> FEATURE:
<221> NAME/KEY: misc_feature
<222> LOCATION: (8)..(8)
<223> OTHER INFORMATION: may be D, A, or E
<220> FEATURE:
<221> NAME/KEY: misc_feature
<222> LOCATION: (11)..(11)
<223> OTHER INFORMATION: may be S or N
<220> FEATURE:
<221> NAME/KEY: misc_feature
<222> LOCATION: (21)..(21)
<223> OTHER INFORMATION: may be N, S, or D
<220> FEATURE:
<221> NAME/KEY: misc_feature
<222> LOCATION: (25)..(25)
<223> OTHER INFORMATION: may be D or E
<220> FEATURE:
<221> NAME/KEY: misc_feature
<222> LOCATION: (28)..(28)
<223> OTHER INFORMATION: may be N, A, or S
```

```
-continued

<220> FEATURE:
<221> NAME/KEY: misc_feature
<222> LOCATION: (40)..(40)
<223> OTHER INFORMATION: may be V, T, or Q
<220> FEATURE:
<221> NAME/KEY: misc_feature
<222> LOCATION: (42)..(42)
<223> OTHER INFORMATION: may be K or A
<220> FEATURE:
<221> NAME/KEY: misc_feature
<222> LOCATION: (43)..(43)
<223> OTHER INFORMATION: may be E or S
<220> FEATURE:
<221> NAME/KEY: misc_feature
<222> LOCATION: (44)..(44)
<223> OTHER INFORMATION: may be L, I, or V
<220> FEATURE:
<221> NAME/KEY: misc_feature
<222> LOCATION: (46)..(46)
<223> OTHER INFORMATION: may be G or A
<220> FEATURE:
<221> NAME/KEY: misc_feature
<222> LOCATION: (49)..(49)
<223> OTHER INFORMATION: may be K or Q
<220> FEATURE:
<221> NAME/KEY: misc_feature
<222> LOCATION: (52)..(52)
<223> OTHER INFORMATION: may be N, S, or D
<220> FEATURE:
<221> NAME/KEY: misc_feature
<222> LOCATION: (53)..(53)
<223> OTHER INFORMATION: may be D or E
<220> FEATURE:
<221> NAME/KEY: misc_feature
<222> LOCATION: (54)..(54)
<223> OTHER INFORMATION: may be A or S
<220> FEATURE:
<221> NAME/KEY: misc_feature
<222> LOCATION: (58)..(58)
<223> OTHER INFORMATION: may be K or P

<400> SEQUENCE: 38

Xaa Xaa Xaa Xaa Xaa Xaa Xaa Xaa Gln Gln Xaa Ala Phe Tyr Glu Ile
1               5                   10                  15

Leu His Leu Pro Xaa Leu Thr Glu Xaa Gln Arg Xaa Ala Phe Ile Gln
            20                  25                  30

Ser Leu Lys Asp Asp Pro Ser Xaa Ser Xaa Xaa Xaa Leu Xaa Glu Ala
        35                  40                  45

Xaa Lys Leu Xaa Xaa Xaa Gln Ala Pro Xaa
    50                  55

<210> SEQ ID NO 39
<211> LENGTH: 11
<212> TYPE: PRT
<213> ORGANISM: Artificial Sequence
<220> FEATURE:
<223> OTHER INFORMATION: Artificially synthesized C-terminal coupling
      sequence (APS10/C)

<400> SEQUENCE: 39

Ala Ser Pro Ala Pro Ser Ala Pro Ser Ala Cys
1               5                   10

<210> SEQ ID NO 40
<211> LENGTH: 33
<212> TYPE: PRT
<213> ORGANISM: Artificial Sequence
<220> FEATURE:
<223> OTHER INFORMATION: Artificially synthesized coupling sequence
      c-terminal  (APS30/C)

<400> SEQUENCE: 40
```

```
Ala Ser Pro Ser Pro Ala Ala Pro Ala Pro Ala Pro Ser Ala Ser
1               5                   10                  15

Pro Ala Pro Ala Ala Pro Ala Pro Ala Ala Ser Pro Ala Ala Ala
            20                  25                  30

Cys

<210> SEQ ID NO 41
<211> LENGTH: 30
<212> TYPE: PRT
<213> ORGANISM: Artificial Sequence
<220> FEATURE:
<223> OTHER INFORMATION: Artificially synthesized APS30 linker

<400> SEQUENCE: 41

Ser Ala Ala Pro Ala Pro Ser Ala Pro Ala Ser Ala Ala Pro Ala Pro
1               5                   10                  15

Ala Pro Ala Pro Ala Pro Ser Pro Ala Ala Pro Ala Ala Ser
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Artificially synthesized APS30 linker

<400> SEQUENCE: 42

Ala Ser Pro Ser Pro Ala Ala Pro Ala Pro Ala Pro Ser Ala Ala Ser
1               5                   10                  15

Pro Ala Pro Ala Ala Pro Ala Pro Ala Ala Ser Pro Ala Ala
            20                  25                  30

<210> SEQ ID NO 43
<211> LENGTH: 10
<212> TYPE: PRT
<213> ORGANISM: Artificial Sequence
<220> FEATURE:
<223> OTHER INFORMATION: Artificially synthesized APS10 linker

<400> SEQUENCE: 43

Ala Ser Pro Ala Pro Ser Ala Pro Ser Ala
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Artificially synthesized Streptag

<400> SEQUENCE: 44

Trp Ser His Pro Gln Phe Glu Lys
1               5

<210> SEQ ID NO 45
<211> LENGTH: 189
<212> TYPE: PRT
<213> ORGANISM: Artificial Sequence
<220> FEATURE:
<223> OTHER INFORMATION: Artificially synthesized IB14 dimer (CID150570)

<400> SEQUENCE: 45

Met Pro Ala Ala Lys His Asp Lys Asp Gln Gln Ser Ala Phe Tyr Glu
1               5                   10                  15
```

```
Ile Leu His Leu Pro Asn Leu Thr Glu Asp Gln Arg Ser Ala Phe Ile
         20                  25                  30

Gln Ser Leu Lys Asp Asp Pro Ser Val Ser Lys Glu Ile Leu Gly Glu
     35                  40                  45

Ala Lys Lys Leu Asn Asp Ala Gln Ala Pro Pro Ser Ala Ala Pro Ala
 50                  55                  60

Pro Ser Ala Pro Ala Ser Ala Ala Pro Ala Pro Ala Pro Ala Pro Ala
 65                  70                  75                  80

Pro Ser Pro Ala Ala Pro Ala Ala Ser Pro Ala Ala Lys His Asp Lys
                 85                  90                  95

Asp Gln Gln Ser Ala Phe Tyr Glu Ile Leu His Leu Pro Asn Leu Thr
                100                 105                 110

Glu Asp Gln Arg Ser Ala Phe Ile Gln Ser Leu Lys Asp Asp Pro Ser
            115                 120                 125

Val Ser Lys Glu Ile Leu Gly Glu Ala Lys Lys Leu Asn Asp Ala Gln
130                 135                 140

Ala Pro Pro Ala Ser Pro Ser Pro Ala Ala Pro Ala Pro Ala Pro Ser
145                 150                 155                 160

Ala Ala Ser Pro Ala Pro Ala Ala Pro Ala Pro Ala Ala Ser Pro Ala
                165                 170                 175

Ala Ala Ala Cys Ala Trp Ser His Pro Gln Phe Glu Lys
            180                 185
```

<210> SEQ ID NO 46
<211> LENGTH: 365
<212> TYPE: PRT
<213> ORGANISM: Artificial Sequence
<220> FEATURE:
<223> OTHER INFORMATION: Artificially synthesized IB14 tetramer
      (CID150663)

<400> SEQUENCE: 46

```
Met Pro Ala Ala Lys His Asp Lys Asp Gln Gln Ser Ala Phe Tyr Glu
 1               5                  10                  15

Ile Leu His Leu Pro Asn Leu Thr Glu Asp Gln Arg Ser Ala Phe Ile
             20                  25                  30

Gln Ser Leu Lys Asp Asp Pro Ser Val Ser Lys Glu Ile Leu Gly Glu
         35                  40                  45

Ala Lys Lys Leu Asn Asp Ala Gln Ala Pro Pro Ser Ala Ala Pro Ala
 50                  55                  60

Pro Ser Ala Pro Ala Ser Ala Ala Pro Ala Pro Ala Pro Ala Pro Ala
 65                  70                  75                  80

Pro Ser Pro Ala Ala Pro Ala Ala Ser Pro Ala Ala Lys His Asp Lys
                 85                  90                  95

Asp Gln Gln Ser Ala Phe Tyr Glu Ile Leu His Leu Pro Asn Leu Thr
                100                 105                 110

Glu Asp Gln Arg Ser Ala Phe Ile Gln Ser Leu Lys Asp Asp Pro Ser
            115                 120                 125

Val Ser Lys Glu Ile Leu Gly Glu Ala Lys Lys Leu Asn Asp Ala Gln
130                 135                 140

Ala Pro Pro Ala Ser Pro Ser Pro Ala Ala Pro Ala Pro Ala Pro Ser
145                 150                 155                 160

Ala Ala Ser Pro Ala Pro Ala Ala Pro Ala Pro Ala Ala Ser Pro Ala
                165                 170                 175

Ala Pro Ala Ala Lys His Asp Lys Asp Gln Gln Ser Ala Phe Tyr Glu
```

```
                180                 185                 190
Ile Leu His Leu Pro Asn Leu Thr Glu Asp Gln Arg Ser Ala Phe Ile
            195                 200                 205

Gln Ser Leu Lys Asp Asp Pro Ser Val Ser Lys Glu Ile Leu Gly Glu
        210                 215                 220

Ala Lys Lys Leu Asn Asp Ala Gln Ala Pro Pro Ser Ala Ala Pro Ala
225                 230                 235                 240

Pro Ser Ala Pro Ala Ser Ala Ala Pro Ala Pro Ala Pro Ala Pro Ala
                245                 250                 255

Pro Ser Pro Ala Ala Pro Ala Ala Ser Pro Ala Ala Lys His Asp Lys
                260                 265                 270

Asp Gln Gln Ser Ala Phe Tyr Glu Ile Leu His Leu Pro Asn Leu Thr
            275                 280                 285

Glu Asp Gln Arg Ser Ala Phe Ile Gln Ser Leu Lys Asp Asp Pro Ser
        290                 295                 300

Val Ser Lys Glu Ile Leu Gly Glu Ala Lys Lys Leu Asn Asp Ala Gln
305                 310                 315                 320

Ala Pro Pro Ala Ser Pro Ser Pro Ala Ala Pro Ala Pro Ala Pro Ser
                325                 330                 335

Ala Ala Ser Pro Ala Pro Ala Ala Pro Ala Pro Ala Ala Ser Pro Ala
            340                 345                 350

Ala Ala Ala Cys Ala Trp Ser His Pro Gln Phe Glu Lys
        355                 360                 365

<210> SEQ ID NO 47
<211> LENGTH: 541
<212> TYPE: PRT
<213> ORGANISM: Artificial Sequence
<220> FEATURE:
<223> OTHER INFORMATION: Artificially synthesized IB14 hexamer
      (CID 150772)

<400> SEQUENCE: 47

Met Pro Ala Ala Lys His Asp Lys Asp Gln Gln Ser Ala Phe Tyr Glu
1               5                   10                  15

Ile Leu His Leu Pro Asn Leu Thr Glu Asp Gln Arg Ser Ala Phe Ile
            20                  25                  30

Gln Ser Leu Lys Asp Asp Pro Ser Val Ser Lys Glu Ile Leu Gly Glu
        35                  40                  45

Ala Lys Lys Leu Asn Asp Ala Gln Ala Pro Pro Ser Ala Ala Pro Ala
    50                  55                  60

Pro Ser Ala Pro Ala Ser Ala Ala Pro Ala Pro Ala Pro Ala Pro Ala
65                  70                  75                  80

Pro Ser Pro Ala Ala Pro Ala Ala Ser Pro Ala Ala Lys His Asp Lys
                85                  90                  95

Asp Gln Gln Ser Ala Phe Tyr Glu Ile Leu His Leu Pro Asn Leu Thr
            100                 105                 110

Glu Asp Gln Arg Ser Ala Phe Ile Gln Ser Leu Lys Asp Asp Pro Ser
        115                 120                 125

Val Ser Lys Glu Ile Leu Gly Glu Ala Lys Lys Leu Asn Asp Ala Gln
    130                 135                 140

Ala Pro Pro Ala Ser Pro Ser Pro Ala Ala Pro Ala Pro Ala Pro Ser
145                 150                 155                 160

Ala Ala Ser Pro Ala Pro Ala Ala Pro Ala Pro Ala Ala Ser Pro Ala
                165                 170                 175
```

Ala Pro Ala Ala Lys His Asp Lys Asp Gln Gln Ser Ala Phe Tyr Glu
        180                 185                 190

Ile Leu His Leu Pro Asn Leu Thr Glu Asp Gln Arg Ser Ala Phe Ile
        195                 200                 205

Gln Ser Leu Lys Asp Asp Pro Ser Val Ser Lys Glu Ile Leu Gly Glu
        210                 215                 220

Ala Lys Lys Leu Asn Asp Ala Gln Ala Pro Pro Ser Ala Ala Pro Ala
225                 230                 235                 240

Pro Ser Ala Pro Ala Ser Ala Ala Pro Ala Pro Ala Pro Ala Pro Ala
                245                 250                 255

Pro Ser Pro Ala Ala Pro Ala Ala Ser Pro Ala Ala Lys His Asp Lys
        260                 265                 270

Asp Gln Gln Ser Ala Phe Tyr Glu Ile Leu His Leu Pro Asn Leu Thr
        275                 280                 285

Glu Asp Gln Arg Ser Ala Phe Ile Gln Ser Leu Lys Asp Asp Pro Ser
        290                 295                 300

Val Ser Lys Glu Ile Leu Gly Glu Ala Lys Lys Leu Asn Asp Ala Gln
305                 310                 315                 320

Ala Pro Pro Ala Ser Pro Ser Pro Ala Ala Pro Ala Pro Ala Pro Ser
                325                 330                 335

Ala Ala Ser Pro Ala Pro Ala Ala Pro Ala Pro Ala Ala Ser Pro Ala
                340                 345                 350

Ala Pro Ala Ala Lys His Asp Lys Asp Gln Gln Ser Ala Phe Tyr Glu
        355                 360                 365

Ile Leu His Leu Pro Asn Leu Thr Glu Asp Gln Arg Ser Ala Phe Ile
        370                 375                 380

Gln Ser Leu Lys Asp Asp Pro Ser Val Ser Lys Glu Ile Leu Gly Glu
385                 390                 395                 400

Ala Lys Lys Leu Asn Asp Ala Gln Ala Pro Pro Ser Ala Ala Pro Ala
                405                 410                 415

Pro Ser Ala Pro Ala Ser Ala Ala Pro Ala Pro Ala Pro Ala Pro Ala
        420                 425                 430

Pro Ser Pro Ala Ala Pro Ala Ala Ser Pro Ala Ala Lys His Asp Lys
        435                 440                 445

Asp Gln Gln Ser Ala Phe Tyr Glu Ile Leu His Leu Pro Asn Leu Thr
450                 455                 460

Glu Asp Gln Arg Ser Ala Phe Ile Gln Ser Leu Lys Asp Asp Pro Ser
465                 470                 475                 480

Val Ser Lys Glu Ile Leu Gly Glu Ala Lys Lys Leu Asn Asp Ala Gln
                485                 490                 495

Ala Pro Pro Ala Ser Pro Ser Pro Ala Ala Pro Ala Pro Ala Pro Ser
        500                 505                 510

Ala Ala Ser Pro Ala Pro Ala Ala Pro Ala Pro Ala Ala Ser Pro Ala
        515                 520                 525

Ala Ala Ala Cys Ala Trp Ser His Pro Gln Phe Glu Lys
530                 535                 540

<210> SEQ ID NO 48
<211> LENGTH: 58
<212> TYPE: PRT
<213> ORGANISM: Artificial Sequence
<220> FEATURE:
<223> OTHER INFORMATION: Artificially synthesized generic sequence for
      e.g. IB24-IB28
<220> FEATURE:
<221> NAME/KEY: misc_feature

```
<222> LOCATION: (1)..(1)
<223> OTHER INFORMATION: may be N or V
<220> FEATURE:
<221> NAME/KEY: misc_feature
<222> LOCATION: (2)..(2)
<223> OTHER INFORMATION: may be A or D
<220> FEATURE:
<221> NAME/KEY: misc_feature
<222> LOCATION: (4)..(4)
<223> OTHER INFORMATION: may be K or Q
<220> FEATURE:
<221> NAME/KEY: misc_feature
<222> LOCATION: (5)..(5)
<223> OTHER INFORMATION: may be H or F
<220> FEATURE:
<221> NAME/KEY: misc_feature
<222> LOCATION: (7)..(7)
<223> OTHER INFORMATION: may be E or K
<220> FEATURE:
<221> NAME/KEY: misc_feature
<222> LOCATION: (8)..(8)
<223> OTHER INFORMATION: may be A, D, or E
<220> FEATURE:
<221> NAME/KEY: misc_feature
<222> LOCATION: (11)..(11)
<223> OTHER INFORMATION: may be S or N
<220> FEATURE:
<221> NAME/KEY: misc_feature
<222> LOCATION: (25)..(25)
<223> OTHER INFORMATION: may be E or D
<220> FEATURE:
<221> NAME/KEY: misc_feature
<222> LOCATION: (40)..(40)
<223> OTHER INFORMATION: may be V or Q
<220> FEATURE:
<221> NAME/KEY: misc_feature
<222> LOCATION: (42)..(42)
<223> OTHER INFORMATION: may be K or A
<220> FEATURE:
<221> NAME/KEY: misc_feature
<222> LOCATION: (43)..(43)
<223> OTHER INFORMATION: may be E or S
<220> FEATURE:
<221> NAME/KEY: misc_feature
<222> LOCATION: (44)..(44)
<223> OTHER INFORMATION: may be V or I
<220> FEATURE:
<221> NAME/KEY: misc_feature
<222> LOCATION: (46)..(46)
<223> OTHER INFORMATION: may be G or A
<220> FEATURE:
<221> NAME/KEY: misc_feature
<222> LOCATION: (49)..(49)
<223> OTHER INFORMATION: may be Q or K
<220> FEATURE:
<221> NAME/KEY: misc_feature
<222> LOCATION: (53)..(53)
<223> OTHER INFORMATION: may be E or E
<220> FEATURE:
<221> NAME/KEY: misc_feature
<222> LOCATION: (54)..(54)
<223> OTHER INFORMATION: may be S or A

<400> SEQUENCE: 48

Xaa Xaa Ala Xaa Xaa Asp Xaa Xaa Gln Gln Xaa Ala Phe Tyr Glu Ile
 1               5                  10                  15

Leu His Leu Pro Asn Leu Thr Glu Xaa Gln Arg Asn Ala Phe Ile Gln
            20                  25                  30

Ser Leu Lys Asp Asp Pro Ser Xaa Ser Xaa Xaa Xaa Leu Xaa Glu Ala
        35                  40                  45

Xaa Lys Leu Asn Xaa Xaa Gln Ala Pro Lys
    50                  55

<210> SEQ ID NO 49
```

```
<211> LENGTH: 58
<212> TYPE: PRT
<213> ORGANISM: Artificial Sequence
<220> FEATURE:
<223> OTHER INFORMATION: Artificially synthesized generic sequence for
      e.g. IB9-IB23
<220> FEATURE:
<221> NAME/KEY: misc_feature
<222> LOCATION: (1)..(1)
<223> OTHER INFORMATION: may be P, N, or A
<220> FEATURE:
<221> NAME/KEY: misc_feature
<222> LOCATION: (2)..(2)
<223> OTHER INFORMATION: may be A or D
<220> FEATURE:
<221> NAME/KEY: misc_feature
<222> LOCATION: (3)..(3)
<223> OTHER INFORMATION: may be A, N, or S
<220> FEATURE:
<221> NAME/KEY: misc_feature
<222> LOCATION: (4)..(4)
<223> OTHER INFORMATION: may be K or Q
<220> FEATURE:
<221> NAME/KEY: misc_feature
<222> LOCATION: (5)..(5)
<223> OTHER INFORMATION: may be H or F
<220> FEATURE:
<221> NAME/KEY: misc_feature
<222> LOCATION: (6)..(6)
<223> OTHER INFORMATION: may be D, S, or A
<220> FEATURE:
<221> NAME/KEY: misc_feature
<222> LOCATION: (7)..(7)
<223> OTHER INFORMATION: may be K or E
<220> FEATURE:
<221> NAME/KEY: misc_feature
<222> LOCATION: (8)..(8)
<223> OTHER INFORMATION: may be D, A, or E
<220> FEATURE:
<221> NAME/KEY: misc_feature
<222> LOCATION: (11)..(11)
<223> OTHER INFORMATION: may be S or N
<220> FEATURE:
<221> NAME/KEY: misc_feature
<222> LOCATION: (21)..(21)
<223> OTHER INFORMATION: may be N, S, or D
<220> FEATURE:
<221> NAME/KEY: misc_feature
<222> LOCATION: (28)..(28)
<223> OTHER INFORMATION: may be S or A
<220> FEATURE:
<221> NAME/KEY: misc_feature
<222> LOCATION: (40)..(40)
<223> OTHER INFORMATION: may be V or T
<220> FEATURE:
<221> NAME/KEY: misc_feature
<222> LOCATION: (43)..(43)
<223> OTHER INFORMATION: may be E or S
<220> FEATURE:
<221> NAME/KEY: misc_feature
<222> LOCATION: (44)..(44)
<223> OTHER INFORMATION: may be I or L
<220> FEATURE:
<221> NAME/KEY: misc_feature
<222> LOCATION: (52)..(52)
<223> OTHER INFORMATION: may be N, D, or S

<400> SEQUENCE: 49

Xaa Xaa Xaa Xaa Xaa Xaa Xaa Xaa Gln Gln Xaa Ala Phe Tyr Glu Ile
1               5                   10                  15

Leu His Leu Pro Xaa Leu Thr Glu Asp Gln Arg Xaa Ala Phe Ile Gln
            20                  25                  30
```

```
Ser Leu Lys Asp Asp Pro Ser Xaa Ser Lys Xaa Xaa Leu Gly Glu Ala
            35                  40                  45

Lys Lys Leu Xaa Asp Ala Gln Ala Pro Pro
 50              55
```